(12) United States Patent
Yamada et al.

(10) Patent No.: US 10,001,487 B2
(45) Date of Patent: Jun. 19, 2018

(54) GLUCOSE DERIVATIVE, AND CELL IMAGING METHOD AND IMAGING AGENT USING SAID DERIVATIVE

(71) Applicant: HIROSAKI UNIVERSITY, Hirosaki-shi, Aomori (JP)

(72) Inventors: Katsuya Yamada, Hirosaki (JP); Ayako Sasaki, Hirosaki (JP); Tadashi Teshima, Ibaraki (JP); Toshihiro Yamamoto, Ibaraki (JP); Yuji Otsuka, Ibaraki (JP)

(73) Assignee: HIROSAKI UNIVERSITY, Hirosaki-Shi, Aomori (JP)

( * ) Notice: Subject to any disclaimer, the term of this patent is extended or adjusted under 35 U.S.C. 154(b) by 31 days.

(21) Appl. No.: 15/302,782

(22) PCT Filed: Apr. 6, 2015

(86) PCT No.: PCT/JP2015/060783
§ 371 (c)(1),
(2) Date: Oct. 7, 2016

(87) PCT Pub. No.: WO2015/156264
PCT Pub. Date: Oct. 15, 2015

(65) Prior Publication Data
US 2017/0122955 A1 May 4, 2017

(30) Foreign Application Priority Data

Apr. 8, 2014 (JP) ................................. 2014-079071

(51) Int. Cl.
*C12Q 1/54* (2006.01)
*G01N 33/66* (2006.01)
*C07H 17/075* (2006.01)
*C07H 19/04* (2006.01)
*A61K 49/00* (2006.01)
*C07H 17/02* (2006.01)
*G01N 33/574* (2006.01)
*G01N 33/58* (2006.01)
*A61K 51/04* (2006.01)

(52) U.S. Cl.
CPC ......... *G01N 33/66* (2013.01); *A61K 49/0002* (2013.01); *A61K 49/0021* (2013.01); *A61K 49/0039* (2013.01); *A61K 49/0052* (2013.01); *A61K 51/0491* (2013.01); *C07H 17/02* (2013.01); *C07H 17/075* (2013.01); *C07H 19/04* (2013.01); *G01N 33/574* (2013.01); *G01N 33/582* (2013.01)

(58) Field of Classification Search
None
See application file for complete search history.

(56) References Cited

U.S. PATENT DOCUMENTS

| 6,268,222 B1 | 7/2001 | Chandler et al. |
| 6,989,140 B2 | 1/2006 | Tidmarsh et al. |
| 2007/0190597 A1 | 8/2007 | Agnew et al. |
| 2009/0084510 A1 | 4/2009 | Perry et al. |
| 2011/0189708 A1 | 8/2011 | Yamada et al. |
| 2014/0154717 A1 | 6/2014 | Yamada et al. |

FOREIGN PATENT DOCUMENTS

| EP | 2703495 A1 | 3/2014 |
| JP | 2002-501184 A | 1/2002 |
| JP | 2006-249243 A | 9/2006 |
| JP | 2009-531289 A | 9/2009 |
| JP | 2010-529421 A | 8/2010 |
| WO | WO 2006/102167 A2 | 9/2006 |
| WO | WO 2010/016587 A1 | 2/2010 |
| WO | WO 2012/070024 A1 | 5/2012 |
| WO | WO 2012/133688 A1 | 10/2012 |
| WO | WO 2014/054601 A1 | 4/2014 |

OTHER PUBLICATIONS

O'Neil et al. Molecular Imaging Biol. (2005) 7: 388-392 (Year: 2005).*
van Berkel et al. ChemMedChem (2012) 7: 606-617 (Year: 2012).*
International Search Report (PCT/ISA/210) dated Apr. 28, 2015, by the Japanese Patent Office as the International Searching Authority for International Application No. PCT/JP2015/060783.
Written Opinion (PCT/ISA/237) dated Apr. 28, 2015, by the Japanese Patent Office as the International Searching Authority for International Application No. PCT/JP2015/060783.
Extended Search Report issued by the European Patent Office in corresponding European Patent Application No. 15776849.0 dated Nov. 15, 2017 (6 pages).
Yamada et al., "Measurement of Glucose Uptake and Intracellular Calcium Concentration in Single, Living Pancreatic β-Cells", J. Biol. Chem., Jul. 2000, pp. 22278-22283, vol. 275, No. 29.
Yamada et al., "A real-time method of imaging glucose uptake in single, living mammalian cells", Nat. Protoc., 2007, pp. 753-762, vol. 2, No. 3.
O'Neil et al., "Uptake of a Fluorescent Deoxyglucose Analog (2-NBDG) in Tumor Cells", Mol. Imaging Biol., 2005, pp. 388-392, vol. 7.
Sheth et al., "Evaluation and clinically relevant applications of a fluorescent imaging analog to fluorodeoxyglucose positron emission tomography", J. Biomed. Opt., Nov./Dec. 2009,pp. 064014-1-8, vol. 14, No. 6.

(Continued)

*Primary Examiner* — Susan M Hanley
(74) *Attorney, Agent, or Firm* — Buchanan, Ingersoll & Rooney PC

(57) ABSTRACT

Provided is a glucose derivative, which is taken into cells via a membrane sugar transport system and is represented by formula (1). Also provided are an imaging agent and an imaging method for a cell or intracellular molecule using said glucose derivative. Further provided are a method for detecting cancer cells with good accuracy using said glucose derivative and an imaging agent to be used in said method. More specifically provided are D-glucose derivatives and L-glucose derivatives in which glucose is bound to the 7-position of a fluorescent molecular group with a coumarin backbone or a quinolone backbone. Also provided are a cell imaging agent and imaging method using the derivative. A cancer cell imaging agent and imaging method using the L-glucose derivative is also provided. G is a group selected from formulas (G1)-(G4) below.

11 Claims, 7 Drawing Sheets

(56) References Cited

OTHER PUBLICATIONS

Nitin et al., "Molecular imaging of glucose uptake in oral neoplasia following topical application of fluorescently labeled deoxy-glucose", Int. J. Cancer, 2009, pp. 2634-2642, vol. 124.

Cheng et al., "Near-Infrared Fluorescent Deoxyglucose Analog for Tumor Optical Imaging in Cell Culture and in Living Mice", Bioconjugate Chem., 2006, pp. 662-669, vol. 17, No. 3.

Wagner et al., "Synthese von Glucosiden der Chinolinreihe nach dem Hilbert-Johnson-Verfahren", Archiv der Pharmazie, 1965, pp. 481-491, 298 (8).

Kimmel et al., "Selective formation of glycosidic linkages of N-unsubstituted 4-hydroxyquinolin-2-(1H)-ones", Carbohydr. Res., 2010, pp. 768-779, vol. 345.

\* cited by examiner

GLUCOSE DERIVATIVE, AND CELL IMAGING METHOD AND IMAGING AGENT USING SAID DERIVATIVE

TECHNICAL FIELD

The present invention relates to a novel glucose derivative. The present invention also relates to a cell imaging method and imaging agent using the novel glucose derivative. The present invention further relates to a method for detecting and/or imaging cancer cells using the novel glucose derivative, and an imaging agent therefor.

BACKGROUND ART

Molecular imaging has been actively conducted which performs imaging for visualization of cells, particularly, living cells, or imaging for visualization targeting molecules in living bodies to reveal molecular kinetics, intermolecular interaction, and molecular positional information, leading to the elucidation of the mechanisms of life science or drug discovery screening. Particularly, researches have also been actively made to detect cancer cells or cancer sites by visualizing abnormal cells, for example, cancer cells.

The group of the present inventors have proposed a method using green fluorescence-emitting 2-[N-(7-nitrobenz-2-oxa-1,3-diazol-4-yl)amino]-2-deoxy-D-glucose (2-NBDG) in which a N-(7-nitrobenz-2-oxa-1,3-diazol-4-yl)amino group is bound as a fluorophore to the 2-position of D-deoxyglucose, as a method that can be used in research on the dynamic uptake process of D-glucose by live cells, and have demonstrated the usefulness of the method using various mammalian cells (Non Patent Literature 1).

This method utilizes 2-NBDG's property of being selectively taken into live cells and can quantitatively determine dynamic activity as to the cellular uptake of D-glucose by monitoring change in fluorescence intensity caused by the uptake. Therefore, this method is highly regarded by researchers around the world as a breakthrough for studying how organisms take D-glucose into cells and utilize the D-glucose, and is now accepted as a standard protocol indispensable in this research field (Non Patent Literature 2).

In the history of the previous development of fluorescent D-glucose derivatives, 2-NBDG and 6-NBDG which are D-glucose derivatives bound to a green fluorescent group NBD are the only substances that have been internationally accepted as being transported into cells via a glucose transporter GLUT and subjected to various replication studies. Furthermore, 2-NBDG is the only molecule that has been found to be taken into cells and then phosphorylated like FDG that has been used in the PET examination of cancers. Therefore, since long ago, it has been suggested that 2-NBDG can be utilized not only for the purposes of basic science fields but also for application to tumor cell imaging in clinical medicine (Non Patent Literature 3, Patent Literature 1, etc.). Also, many attempts have been made to apply 2-NBDG to the diagnostic imaging of cancers (Non Patent Literatures 4 and 5).

As another compound than 2-NBDG expected to pass through GLUT, the inventors have developed 2-DBDG (2-[N-7-(N',N'-dimethylaminosulfonyl)benz-2-oxa-1,3-diazol-4-yl)amino]-2-deoxy-D-glucose) which is a molecule in which DBD that is an analog of NBD is bound to D-glucose, and have reported the properties of this compound (Patent Literature 2). Even though 2-DBDG has a fluorescence wavelength slightly shifted to the longer wavelength side as compared with 2-NBDG, it largely overlaps with 2-NBDG in terms of spectra. Thus, when 2-DBDG is used with 2-NBDG at the same time, a problem arises for discriminating them from each other.

In fact, D-glucose derivatives bound to various other fluorescent molecules than NBD have also been proposed so far. Particularly, there have been developed a molecule bound to a more highly tissue-permeable probe having the maximum fluorescence in the near-infrared region, a molecule suitable for excitation using a two-photon microscope, a molecule that emits stronger fluorescence than 2-NBDG, and the like. However, because these D-glucose derivative molecules have a much larger molecular size than 2-NBDG, mechanisms underlying their uptake into cells are presumed to be cellular uptake via pathways other than GLUT, for example, uptake by phagocytosis or by internalization in a protein-bound state (Non Patent Literature 6).

In addition to the molecules having a green, red, or near-infrared fluorescence spectrum, fluorescent glucose derivatives have also been reported which have a D-glucose bound to a coumarin derivative molecule having a blue fluorescence spectrum (Esculin, Fraxin, and compounds described in WO2012/70024 (Patent Literature 3)). However, these derivatives are not taken into cells via GLUT. There has been no report on a molecule that is a sugar derivative having, in its molecule, a blue fluorescent molecular group and passes through GLUT.

As for substances in which a quinoline derivative molecule is bound to glucose, G. Wagner et al. (Non Patent Literature 7) have reported the following substances:

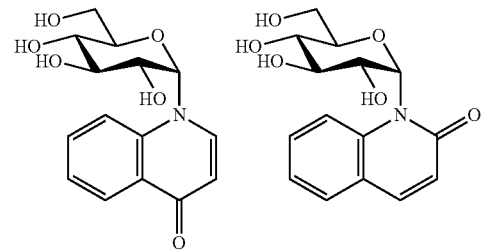

and Roman Kimmel et al. (Non Patent Literature 8) have reported the following substance:

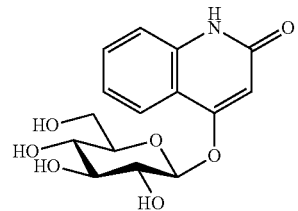

However, all of these substances have a structure where a quinoline derivative is bound to the 1-position of glucose either directly or via an oxygen atom. It has not been reported that any of them are taken into cells via GLUT.

Meanwhile, the present inventors have proposed compounds in which 3-carboxy-6,8-difluoro-7-hydroxycoumarin (Pacific Blue) or 3-carboxymethyl-6,8-difluoro-7-hydroxy-4-methylcoumarin (Marina Blue) is bound to glucose via an amide bond, and have filed a patent application of PCT/JP2013/076629.

Patent Literature 1: U.S. Pat. No. 6,989,140 specification

Patent Literature 2: WO2010/16587

Patent Literature 3: WO2012/70024

Patent Literature 4: WO2012/133688

Non Patent Literature 1: Yamada K. et al., J. Biol. Chem. 275: 22278-22283, 2000

Non Patent Literature 2: Yamada K. et al., Nat. Protoc. 2: 753-762, 2007

Non Patent Literature 3: O'Neil et al., Mol. Imaging Biol. 7: 388-392

Non Patent Literature 4: Sheth et al., J. Biomed. Opt. 14: 064014-1-8, 2009

Non Patent Literature 5: Nitin et al., Int. J. Cancer 2009

Non Patent Literature 6: Cheng Z. et al., Bioconjugate Chem. 17: 662-669, 2006

Non Patent Literature 7: G. Wagner, et al., Archiv der Pharmazie, 298 (8), 481-491 (1965)

Non Patent Literature 8: Roman Kimmel, et al., Carbohydr. Res., 345, 768-779 (2010)

SUMMARY OF INVENTION

A purpose of the present invention is to provide a novel glucose derivative, which is taken into cells via a membrane sugar transport system. Another purpose of the present invention is to provide an imaging method and imaging agent for a cell using such a glucose derivative. Yet another purpose of the present invention is to provide a method for detecting cancer cells with good accuracy by imaging, and an imaging agent for use in the method.

As a result of conducting diligent studies in light of the points described above, the present inventors have completed the present invention by finding that a novel glucose derivative having a particular structure is taken into cells via a membrane sugar transport system. The present inventors have completed the present invention by also finding that cells can be imaged with good accuracy by use of the novel glucose derivative.

The present invention is as follows:

1. A glucose derivative which is selected from a compound represented by the following formula (1):

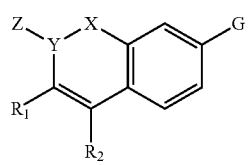

wherein X—Y—Z represents O—C=O, NH—C=O, $NR_3$—C=O, or N=C—$OR_4$, wherein $R_3$ represents $C_1$-$C_5$ alkyl, and $R_4$ represents $C_1$-$C_5$ alkyl; $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl; and G represents a group selected from the following formulas (G1) to (G4):

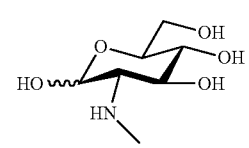

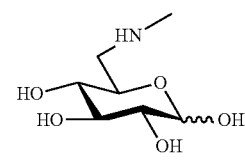

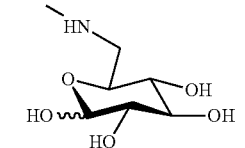

and a salt thereof.

2. The glucose derivative according to the above item 1, which is a compound represented by the following formula (2):

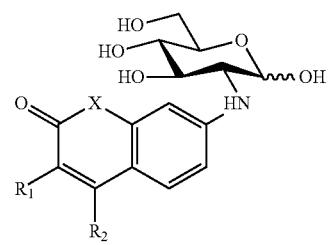

wherein X represents O, NH, or $NR_3$, wherein $R_3$ represents $C_1$-$C_5$ alkyl; and $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl, or a salt thereof.

3. The glucose derivative according to the above item 2, wherein in the formula (2), X is O.

4. The glucose derivative according to the above item 1, which is a compound represented by the following formula (3):

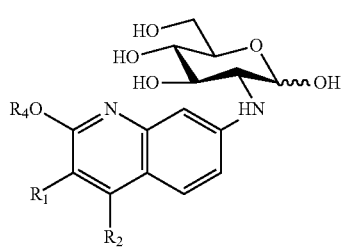

wherein $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl; and $R_4$ represents $C_1$-$C_5$ alkyl, or a salt thereof.

5. The glucose derivative according to the above item 1, which is a compound represented by the following formula (4):

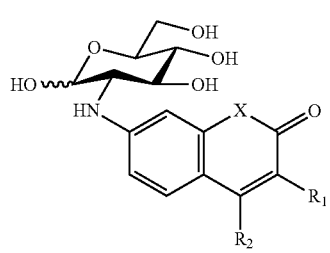

(4)

wherein X represents O, NH, or $NR_3$, wherein $R_3$ represents $C_1$-$C_5$ alkyl; and $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl, or a salt thereof.

6. The glucose derivative according to the above item 5, wherein in the formula (4), X is O.

7. The glucose derivative according to the above item 1, which is a compound represented by the following formula (5):

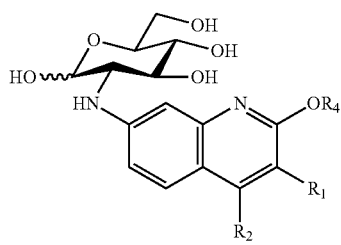

(5)

wherein $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl; and $R_4$ represents $C_1$-$C_5$ alkyl, or a salt thereof.

8. The glucose derivative according to the above item 1, which is selected from the group consisting of the following compounds:

2-deoxy-2-(2-oxo-2H-chromen-7-yl)amino-D-glucose, 2-deoxy-2-(2-oxo-2H-3-methyl-chromen-7-yl)amino-D-glucose, 2-deoxy-2-(2-oxo-2H-3-trifluoromethyl-chromen-7-yl)amino-D-glucose, 2-deoxy-2-(2-oxo-2H-4-methyl-chromen-7-yl)amino-D-glucose, 2-deoxy-2-(2-oxo-2H-4-trifluoromethyl-chromen-7-yl)amino-D-glucose, 2-deoxy-2-(2-oxo-2H-3-phenyl-chromen-7-yl)amino-D-glucose, 2-deoxy-2-(2-oxo-2H-3-(pyridin-2-yl)-chromen-7-yl)amino-D-glucose, 2-deoxy-2-(2-oxo-2H-3-(pyridin-4-yl)-chromen-7-yl)amino-D-glucose, 2-deoxy-2-(2-oxo-2H-3-(thiophen-2-yl)-chromen-7-yl)amino-D-glucose, 2-deoxy-2-(2-oxo-2H-3-(furan-2-yl)-chromen-7-yl)amino-D-glucose, 2-deoxy-2-(2-oxo-2H-3-(pyrrol-2-yl)-chromen-7-yl)amino-D-glucose, 2-deoxy-2-(2-oxo-2H-3-phenyl-4-methyl-chromen-7-yl)amino-D-glucose, 2-deoxy-2-(2-oxo-2H-3-(pyridin-2-yl)-4-methyl-chromen-7-yl)amino-D-glucose, 2-deoxy-2-(2-oxo-2H-3-(pyridin-4-yl)-4-methyl-chromen-7-yl)amino-D-glucose, 2-deoxy-2-(2-oxo-2H-3-(thiophen-2-yl)-4-methyl-chromen-7-yl)amino-D-glucose, 2-deoxy-2-(2-oxo-2H-3-(furan-2-yl)-4-methyl-chromen-7-yl)amino-D-glucose, 2-deoxy-2-(2-oxo-2H-3-(pyrrol-2-yl)-4-methyl-chromen-7-yl)amino-D-glucose, 2-deoxy-2-(2-oxo-2H-3-phenyl-4-trifluoromethyl-chromen-7-yl)amino-D-glucose, 2-deoxy-2-(2-oxo-2H-3-(pyridin-2-yl)-4-trifluoromethyl-chromen-7-yl)amino-D-glucose, 2-deoxy-2-(2-oxo-2H-3-(pyridin-4-yl)-4-trifluoromethyl-chromen-7-yl)amino-D-glucose, 2-deoxy-2-(2-oxo-2H-3-(thiophen-2-yl)-4-trifluoromethyl-chromen-7-yl)amino-D-glucose, 2-deoxy-2-(2-oxo-2H-3-(furan-2-yl)-4-trifluoromethyl-chromen-7-yl)amino-D-glucose, 2-deoxy-2-(2-oxo-2H-3-(pyrrol-2-yl)-4-trifluoromethyl-chromen-7-yl)amino-D-glucose, 2-deoxy-2-(2-oxo-2H-3-iodo-chromen-7-yl)amino-D-glucose, 2-deoxy-2-(2-oxo-2H-4-iodo-chromen-7-yl)amino-D-glucose, 2-deoxy-2-(2-oxo-2H-3-formyl-chromen-7-yl)amino-D-glucose, 2-deoxy-2-(2-oxo-2H-4-formyl-chromen-7-yl)amino-D-glucose, 2-deoxy-2-(2-oxo-2H-3-ethenyl-chromen-7-yl)amino-D-glucose, 2-deoxy-2-(2-oxo-2H-4-ethenyl-chromen-7-yl)amino-D-glucose, 2-deoxy-2-(2-oxo-2H-3-ethynyl-chromen-7-yl)amino-D-glucose, 2-deoxy-2-(2-oxo-2H-4-ethynyl-chromen-7-yl)amino-D-glucose, 2-deoxy-2-(2-oxo-2H-3,4-dimethyl-chromen-7-yl)amino-D-glucose, 2-deoxy-2-(2-oxo-2H-3-acetyl-chromen-7-yl)amino-D-glucose, 2-deoxy-2-(2-oxo-2H-4-acetyl-chromen-7-yl)amino-D-glucose, 2-deoxy-2-(2-oxo-2H-3-cyclopropanyl-chromen-7-yl)amino-D-glucose, 2-deoxy-2-(2-oxo-2H-4-cyclopropanyl-chromen-7-yl)amino-D-glucose, 2-deoxy-2-(2-oxo-2H-3-methyl-4-acetyl-chromen-7-yl)amino-D-glucose, 2-deoxy-2-(2-oxo-2H-3-acetyl-4-methyl-chromen-7-yl)amino-D-glucose, 2-deoxy-2-(2-oxo-2H-3-propenyl-chromen-7-yl)amino-D-glucose, 2-deoxy-2-(2-oxo-2H-4-propenyl-chromen-7-yl)amino-D-glucose, 2-deoxy-2-(2-oxo-1,2-dihydro-quinolin-7-yl)amino-D-glucose, 2-deoxy-2-(2-oxo-1,2-dihydro-3-methyl-quinolin-7-yl)amino-D-glucose, 2-deoxy-2-(2-oxo-1,2-dihydro-3-trifluoromethyl-quinolin-7-yl)amino-D-glucose, 2-deoxy-2-(2-oxo-1,2-dihydro-4-methyl-quinolin-7-yl)amino-D-glucose, 2-deoxy-2-(2-oxo-1,2-dihydro-4-trifluoromethyl-quinolin-7-yl)amino-D-glucose, 2-deoxy-2-(2-oxo-1,2-dihydro-3-phenyl-quinolin-7-yl)amino-D-glucose, 2-deoxy-2-(2-oxo-1,2-dihydro-3-(pyridin-2-yl)-quinolin-7-yl)amino-D-glucose, 2-deoxy-2-(2-oxo-1,2-dihydro-3-(pyridin-4-yl)-quinolin-7-yl)amino-D-glucose, 2-deoxy-2-(2-oxo-1,2-dihydro-3-(thiophen-2-yl)-quinolin-7-yl)amino-D-glucose, 2-deoxy-2-(2-oxo-1,2-dihydro-3-(furan-2-yl)-quinolin-7-yl)amino-D-glucose, 2-deoxy-2-(2-oxo-1,2-dihydro-3-(pyrrol-2-yl)-quinolin-7-yl)amino-D-glucose, 2-deoxy-2-(2-oxo-1,2-dihydro-3-phenyl-4-methyl-quinolin-7-yl)amino-D-glucose, 2-deoxy-2-(2-oxo-1,2-dihydro-3-(pyridin-2-yl)-4-methyl-quinolin-7-yl)amino-D-glucose, 2-deoxy-2-(2-oxo-1,2-dihydro-3-(pyridin-4-yl)-4-methyl-quinolin-7-yl)amino-D-glucose, 2-deoxy-2-(2-oxo-1,2-dihydro-3-(thiophen-2-yl)-4-methyl-quinolin-7-yl)amino-D-glucose, 2-deoxy-2-(2-oxo-1,2-dihydro-3-(furan-2-yl)-4-methyl-quinolin-7- yl)amino-D-glucose, 2-deoxy-2-(2-oxo-1,2-dihydro-3-(pyrrol-2-yl)-4-methyl-quinolin-7-yl)amino-D-glucose, 2-deoxy-2-(2-oxo-1,2-dihydro-3-phenyl-4-trifluoromethyl-quinolin-7-yl)amino-D-glucose, 2-deoxy-2-(2-oxo-1,2-dihydro-3-(pyridin-2-yl)-4-trifluoromethyl-quinolin-7-yl)amino-D-glucose, 2-deoxy-2-(2-oxo-1,2-dihydro-3-(pyridin-4-yl)-4-trifluoromethyl-quinolin-7-yl)amino-D-glucose, 2-deoxy-2-(2-oxo-1,2-dihydro-3-(thiophen-2-yl)-4-trifluoromethyl-quinolin-7-yl)amino-D-glucose, 2-deoxy-2-(2-oxo-1,2-dihydro-3-(furan-2-yl)-4-trifluoromethyl-quinolin-7-yl)amino-D-glucose, 2-deoxy-2-(2-oxo-1,2-dihydro-3-(pyrrol-2-yl)-4-trifluoromethyl-quinolin-7-yl)amino-D-glucose, 2-deoxy-2-(2-oxo-1,2-dihydro-3-iodo-quinolin-7-yl)amino-D-glucose, 2-deoxy-2-(2-oxo-1,2-dihydro-4-iodo-quinolin-7-yl)amino-D-glucose, 2-deoxy-2-(2-oxo-1,2-dihydro-3-formyl-quinolin-7-yl)amino-D-glucose, 2-deoxy-2-(2-oxo-1,2-dihydro-4-formyl-quinolin-7-yl)amino-D-glucose, 2-deoxy-2-(2-oxo-1,2-dihydro-3-ethenyl-quinolin-7-yl)amino-D-glucose, 2-deoxy-2-(2-oxo-1,2-dihydro-4-ethenyl-quinolin-7-yl)amino-D-glucose, 2-deoxy-2-(2-oxo-1,2-dihydro-3-ethynyl-quinolin-7-yl)amino-D-glucose, 2-deoxy-2-(2-oxo-1,2-dihydro-4-ethynyl-quinolin-7-yl)amino-D-glucose, 2-deoxy-2-(2-oxo-1,2-dihydro-3,4-dimethyl-quinolin-7-yl)amino-D-glucose, 2-deoxy-2-(2-oxo-1,2-dihydro-3-acetyl-quinolin-7-yl)amino-D-glucose, 2-deoxy-2-(2-oxo-1,2-dihydro-4-acetyl-quinolin-7-yl)amino-D-glucose, 2-deoxy-2-(2-oxo-1,2-dihydro-3-cyclopropanyl-quinolin-7-yl)amino-D-glucose, 2-deoxy-2-(2-oxo-1,2-dihydro-4-cyclopropanyl-quinolin-7-yl)amino-D-glucose, 2-deoxy-2-(2-oxo-1,2-dihydro-3-acetyl-4-methyl-quinolin-7-yl)amino-D-glucose, 2-deoxy-2-(2-oxo-1,2-dihydro-3-methyl-4-acetyl-quinolin-7-yl)amino-D-glucose, 2-deoxy-2-(2-oxo-1,2-dihydro-3-propenyl-quinolin-7-yl)amino-D-glucose, 2-deoxy-2-(2-oxo-1,2-dihydro-4-propenyl-quinolin-7-yl)amino-D-glucose, 2-deoxy-2-(1-methyl-2-oxo-1,2-dihydro-quinolin-7-yl)amino-D-glucose, 2-deoxy-2-(2-methoxyquinolin-7-yl)amino-D-glucose, 2-deoxy-2-(2-oxo-2H-chromen-7-yl)amino-L-glucose, 2-deoxy-2-(2-oxo-2H-3-methyl-chromen-7-yl)amino-L-glucose, 2-deoxy-2-(2-oxo-2H-3-trifluoromethyl-chromen-7-yl)amino-L-glucose, 2-deoxy-2-(2-oxo-2H-4-methyl-chromen-7-yl)amino-L-glucose, 2-deoxy-2-(2-oxo-2H-4-trifluoromethyl-chromen-7-yl)amino-L-glucose, 2-deoxy-2-(2-oxo-2H-3-phenyl-chromen-7-yl)amino-L-glucose, 2-deoxy-2-(2-oxo-2H-3-(pyridin-2-yl)-chromen-7-yl)amino-L-glucose, 2-deoxy-2-(2-oxo-2H-3-(pyridin-4-yl)-chromen-7-yl)amino-L-glucose, 2-deoxy-2-(2-oxo-2H-3-(thiophen-2-yl)-chromen-7-yl)amino-L-glucose, 2-deoxy-2-(2-oxo-2H-3-(furan-2-yl)-chromen-7-yl)amino-L-glucose, 2-deoxy-2-(2-oxo-2H-3-(pyrrol-2-yl)-chromen-7-yl)amino-L-glucose, 2-deoxy-2-(2-oxo-2H-3-phenyl-4-methyl-chromen-7-yl)amino-L-glucose, 2-deoxy-2-(2-oxo-2H-3-(pyridin-2-yl)-4-methyl-chromen-7-yl)amino-L-glucose, 2-deoxy-2-(2-oxo-2H-3-(pyridin-4-yl)-4-methyl-chromen-7-yl)amino-L-glucose, 2-deoxy-2-(2-oxo-2H-3-(thiophen-2-yl)-4-methyl-chromen-7-yl)amino-L-glucose, 2-deoxy-2-(2-oxo-2H-3-(furan-2-yl)-4-methyl-chromen-7-yl)amino-L-glucose, 2-deoxy-2-(2-oxo-2H-3-(pyrrol-2-yl)-4-methyl-chromen-7-yl)amino-L-glucose, 2-deoxy-2-(2-oxo-2H-3-phenyl-4-trifluoromethyl-chromen-7-yl)amino-L-glucose, 2-deoxy-2-(2-oxo-2H-3-(pyridin-2-yl)-4-trifluoromethyl-chromen-7-yl)amino-L-glucose, 2-deoxy-2-(2-oxo-2H-3-(pyridin-4-yl)-4-trifluoromethyl-chromen-7-yl)amino-L-glucose, 2-deoxy-2-(2-oxo-2H-3-(thiophen-2-yl)-4-trifluoromethyl-chromen-7-yl)amino-L-glucose, 2-deoxy-2-(2-oxo-2H-3-(furan-2-yl)-4-trifluoromethyl-chromen-7-yl)amino-L-glucose, 2-deoxy-2-(2-oxo-2H-3-(pyrrol-2-yl)-4-trifluoromethyl-chromen-7-yl)amino-L-glucose, 2-deoxy-2-(2-oxo-2H-3-iodo-chromen-7-yl)amino-L-glucose, 2-deoxy-2-(2-oxo-2H-4-iodo-chromen-7-yl)amino-L-glucose, 2-deoxy-2-(2-oxo-2H-3-formyl-chromen-7-yl)amino-L-glucose, 2-deoxy-2-(2-oxo-2H-4-formyl-chromen-7-yl)amino-L-glucose, 2-deoxy-2-(2-oxo-2H-3-ethenyl-chromen-7-yl)amino-L-glucose, 2-deoxy-2-(2-oxo-2H-4-ethenyl-chromen-7-yl)amino-L-glucose, 2-deoxy-2-(2-oxo-2H-3-ethynyl-chromen-7-yl)amino-L-glucose, 2-deoxy-2-(2-oxo-2H-4-ethynyl-chromen-7-yl)amino-L-glucose, 2-deoxy-2-(2-oxo-2H-3,4-dimethyl-chromen-7-yl)amino-L-glucose, 2-deoxy-2-(2-oxo-2H-3-acetyl-chromen-7-yl)amino-L-glucose, 2-deoxy-2-(2-oxo-2H-4-acetyl-chromen-7-yl)amino-L-glucose, 2-deoxy-2-(2-oxo-2H-3-cyclopropanyl-chromen-7-yl)amino-L-glucose, 2-deoxy-2-(2-oxo-2H-4-cyclopropanyl-chromen-7-yl)amino-L-glucose, 2-deoxy-2-(2-oxo-2H-3-methyl-4-acetyl-chromen-7-yl)amino-L-glucose, 2-deoxy-2-(2-oxo-2H-3-acetyl-4-methyl-chromen-7-yl)amino-L-glucose, 2-deoxy-2-(2-oxo-2H-3-propenyl-chromen-7-yl)amino-L-glucose, 2-deoxy-2-(2-oxo-2H-4-propenyl-chromen-7-yl)amino-L-glucose, 2-deoxy-2-(2-oxo-1,2-dihydro-quinolin-7-yl)amino-L-glucose, 2-deoxy-2-(2-oxo-1,2-dihydro-3-methyl-quinolin-7-yl)amino-L-glucose, 2-deoxy-2-(2-oxo-1,2-dihydro-3-trifluoromethyl-quinolin-7-yl)amino-L-glucose, 2-deoxy-2-(2-oxo-1,2-dihydro-4-methyl-quinolin-7-yl)amino-L-glucose, 2-deoxy-2-(2-oxo-1,2-dihydro-4-trifluoromethyl-quinolin-7-yl)amino-L-glucose, 2-deoxy-2-(2-oxo-1,2-dihydro-3-phenyl-quinolin-7-yl)amino-L-glucose, 2-deoxy-2-(2-oxo-1,2-dihydro-3-(pyridin-2-yl)-quinolin-7-yl)amino-L-glucose, 2-deoxy-2-(2-oxo-1,2-dihydro-3-(pyridin-4-yl)-quinolin-7-yl)amino-L-glucose, 2-deoxy-2-(2-oxo-1,2-dihydro-3-(thiophen-2-yl)-quinolin-7-yl)amino-L-glucose, 2-deoxy-2-(2-oxo-1,2-dihydro-3-(furan-2-yl)-quinolin-7-yl)amino-L-glucose, 2-deoxy-2-(2-oxo-1,2-dihydro-3-(pyrrol-2-yl)-quinolin-7-yl)amino-L-glucose, 2-deoxy-2-(2-oxo-1,2-dihydro-3-phenyl-4-methyl-quinolin-7-yl)amino-L-glucose, 2-deoxy-2-(2-oxo-1,2-dihydro-3-(pyridin-2-yl)-4-methyl-quinolin-7-yl)amino-L-glucose, 2-deoxy-2-(2-oxo-1,2-dihydro-3-(pyridin-4-yl)-4-methyl-quinolin-7-yl)amino-L-glucose, 2-deoxy-2-(2-oxo-1,2-dihydro-3-(thiophen-2-yl)-4-methyl-quinolin-7-yl)amino-L-glucose, 2-deoxy-2-(2-oxo-1,2-dihydro-3-(furan-2-yl)-4-methyl-quinolin-7-yl)amino-L-glucose, 2-deoxy-2-(2-oxo-1,2-dihydro-3-(pyrrol-2-yl)-4-methyl-quinolin-7-yl)amino-L-glucose, 2-deoxy-2-(2-oxo-1,2-dihydro-3-phenyl-4-trifluoromethyl-quinolin-7-yl)amino-L-glucose, 2-deoxy-2-(2-oxo-1,2-dihydro-3-(pyridin-2-yl)-4-trifluoromethyl-quinolin-7-yl)amino-L-glucose, 2-deoxy-2-(2-oxo-1,2-dihydro-3-(pyridin-4-yl)-4-trifluoromethyl-quinolin-7-yl)amino-L-glucose, 2-deoxy-2-(2-oxo-1,2-dihydro-3-(thiophen-2-yl)-4-trifluoromethyl-quinolin-7-yl)amino-L-glucose, 2-deoxy-2-(2-oxo-1,2-dihydro-3-(furan-2-yl)-4-trifluoromethyl-quinolin-7-yl)amino-L-glucose, 2-deoxy-2-(2-oxo-1,2-dihydro-3-(pyrrol-2-yl)-4-trifluoromethyl-quinolin-7-yl)amino-L-glucose, 2-deoxy-2-(2-oxo-1,2-dihydro-3-iodo-quinolin-7-yl)amino-L-glucose, 2-deoxy-2-(2-oxo-1,2-dihydro-4-iodo-quinolin-7-yl)amino-L-glucose, 2-deoxy-2-(2-oxo-1,2-dihydro-3-formyl-quinolin-7-yl)amino-L-glucose, 2-deoxy-2-(2-oxo-1,2-dihydro-4-formyl-quinolin-7-yl)amino-L-glucose, 2-deoxy-2-(2-oxo-1,2- dihydro-3-ethenyl-quinolin-7-yl)amino-L-glucose, 2-deoxy-2-(2-oxo-1,2-dihydro-4-ethenyl-quinolin-7-yl)amino-L-glucose, 2-deoxy-2-(2-oxo-1,2-dihydro-3-ethynyl-quinolin-7-yl)amino-L-glucose, 2-deoxy-2-(2-oxo-1,2-dihydro-4-ethynyl-quinolin-7-yl)amino-L-glucose, 2-deoxy-2-(2-oxo-1,2-dihydro-3,4-dimethyl-quinolin-7-yl)amino-L-glucose, 2-deoxy-2-(2-oxo-1,2-dihydro-3-acetyl-quinolin-7-yl)amino-L-glucose, 2-deoxy-2-(2-oxo-1,2-dihydro-4-acetyl-quinolin-7-yl)amino-L-glucose, 2-deoxy-2-(2-oxo-1,2-dihydro-3-cyclopropanyl-quinolin-7-yl)amino-L-glucose, 2-deoxy-2-(2-oxo-1,2-dihydro-4-cyclopropanyl-quinolin-7-yl)amino-L-glucose, 2-deoxy-2-(2-oxo-1,2-dihydro-3-acetyl-4-methyl-quinolin-7-yl)amino-L-glucose, 2-deoxy-2-(2-oxo-1,2-dihydro-3-methyl-4-acetyl-quinolin-7-yl)amino-L-glucose, 2-deoxy-2-(2-oxo-1,2-dihydro-3-propenyl-quinolin-7-yl)amino-D-glucose, 2-deoxy-2-(2-oxo-1,2-dihydro-4-propenyl-quinolin-7-yl)amino-L-glucose, 2-deoxy-2-(1-methyl-2-oxo-1,2-dihydro-quinolin-7-yl)amino-L-glucose, and 2-deoxy-2-(2-methoxyquinolin-7-yl)amino-L-glucose.

9. The glucose derivative according to the above item 1, which is selected from the group consisting of the following compounds:
2-deoxy-2-(2-oxo-2H-chromen-7-yl)amino-D-glucose (in the present specification, also referred to as CDG), 2,4-dideoxy-2-(2-oxo-2H-chromen-7-yl)amino-4-fluoro-D-glucose (4-F-CDG), 2,6-dideoxy-2-(2-oxo-2H-chromen-7-yl)amino-6-fluoro-D-glucose (6-F-CDG), 2-deoxy-2-(2-oxo-1,2-dihydroquinolin-7-yl)amino-D-glucose (QDG), 2-deoxy-2-(2-oxo-2H-3-methyl-chromen-7-yl)amino-D-glucose (3-MCDG), 2-deoxy-2-(2-oxo-2H-4-methyl-chromen-7-yl)amino-D-glucose (4-MCDG), 2-deoxy-2-(2-oxo-2H-3-trifluoromethyl-chromen-7-yl)amino-D-glucose (3-TFMCDG), 2-deoxy-2-(2-oxo-2H-4-trifluoromethyl-chromen-7-yl)amino-D-glucose (4-TFMCDG), 2-deoxy-2-(2-oxo-1,2-dihydro-3-methyl-quinolin-7-yl)amino-D-glucose (3-MQDG), 2-deoxy-2-(2-oxo-1,2-dihydro-4-methyl-quinolin-7-yl)amino-D-glucose (4-MQDG), 2-deoxy-2-(2-oxo-1,2-dihydro-3-trifluoromethyl-quinolin-7-yl)amino-D-glucose (3-TFMQDG), 2-deoxy-2-(2-oxo-1,2-dihydro-4-trifluoromethyl-quinolin-7-yl)amino-D-glucose (4-TFMQDG), 2-deoxy-2-(2-oxo-2H-chromen-7-yl)amino-L-glucose (CLG), 2,4-dideoxy-2-(2-oxo-2H-chromen-7-yl)amino-4-fluoro-L-glucose (4-F-CLG), 2,6-dideoxy-2-(2-oxo-2H-chromen-7-yl)amino-6-fluoro-L-glucose (6-F-CLG), 2-deoxy-2-(2-oxo-1,2-dihydroquinolin-7-yl)amino-L-glucose (QLG), 2-deoxy-2-(2-oxo-2H-3-methyl-chromen-7-yl)amino-L-glucose (3-MCLG), 2-deoxy-2-(2-oxo-2H-4-methyl-chromen-7-yl)amino-L-glucose (4-MCLG), 2-deoxy-2-(2-oxo-2H-3-trifluoromethyl-chromen-7-yl)amino-L-glucose (3-TFMCLG), 2-deoxy-2-(2-oxo-2H-4-trifluoromethyl-chromen-7-yl)amino-L-glucose (4-TFMCLG), 2-deoxy-2-(2-oxo-1,2-dihydro-3-methyl-quinolin-7-yl)amino-L-glucose (3-MQLG), 2-deoxy-2-(2-oxo-1,2-dihydro-4-methyl-quinolin-7-yl)amino-L-glucose (4-MQLG), 2-deoxy-2-(2-oxo-1,2-dihydro-3-trifluoromethyl-quinolin-7-yl)amino-L-glucose (3-TFMQLG), and 2-deoxy-2-(2-oxo-1,2-dihydro-4-trifluoromethyl-quinolin-7-yl)amino-L-glucose (4-TFMQLG).

10. The glucose derivative according to the above item 9, which is 2-deoxy-2-(2-oxo-2H-chromen-7-yl)amino-D-glucose (CDG), 2-deoxy-2-(2-oxo-1,2-dihydroquinolin-7-yl)amino-D-glucose (QDG), 2-deoxy-2-(2-oxo-2H-chromen-7-yl)amino-L-glucose (CLG), or 2-deoxy-2-(2-oxo-1,2-dihydroquinolin-7-yl)amino-L-glucose (QLG).

11. A radiolabeled glucose derivative comprising a glucose derivative according to any one of the above items 1 to 10, wherein a hydroxy group or a fluorine group at any one of the 2-, 4-, and 6-positions of the glucose is substituted by $^{18}F$, and which is preferably 2,4-dideoxy-2-(2-oxo-2H-chromen-7-yl)amino-4-[$^{18}F$]fluoro-D-glucose (4-$^{18}F$-CDG), 2,4-dideoxy-2-(2-oxo-2H-chromen-7-yl)amino-4-[$^{18}F$]fluoro-L-glucose (4-$^{18}F$-CLG), 2,6-dideoxy-2-(2-oxo-2H-chromen-7-yl)amino-6-[$^{18}F$]fluoro-D-glucose (6-$^{18}F$-CDG), or 2,6-dideoxy-2-(2-oxo-2H-chromen-7-yl)amino-6-[$^{18}F$]fluoro-L-glucose (6-$^{18}F$-CLG).

12. A radiolabeled glucose derivative comprising a glucose derivative according to any of the above items 1 to 9, wherein $R_1$ or $R_2$ is $^{11}CH_3$ or $CF_2^{18}F$, and which is preferably 2-deoxy-2-(2-oxo-2H-3-[$^{11}C$]methyl-chromen-7-yl)amino-D-glucose (3-[$^{11}C$]MCDG), 2-deoxy-2-(2-oxo-2H-4-[$^{11}C$]methyl-chromen-7-yl)amino-D-glucose (4-[$^{11}C$]MCDG), 2-deoxy-2-(2-oxo-2H-3-[$^{18}F$]fluorodifluoromethyl-chromen-7-yl)amino-D-glucose (3-[$^{18}F$]TFMCDG), 2-deoxy-2-(2-oxo-2H-4-[$^{18}F$]fluorodifluoromethyl-chromen-7-yl)amino-D-glucose (4-[$^{18}F$]TFMCDG), 2-deoxy-2-(2-oxo-1,2-dihydro-3-[$^{11}C$]methyl-quinolin-7-yl)amino-D-glucose (3-[$^{11}C$]MQDG), 2-deoxy-2-(2-oxo-1,2-dihydro-4-[$^{11}C$]methyl-quinolin-7-yl)amino-D-glucose (4-[$^{11}C$]MQDG), 2-deoxy-2-(2-oxo-1,2-dihydro-3-[$^{18}F$]fluorodifluoromethyl-quinolin-7-yl)amino-D-glucose (3-[$^{18}F$]=QDG), 2-deoxy-2-(2-oxo-1,2-dihydro-4-[$^{18}F$]fluorodifluoromethyl-quinolin-7-yl)amino-D-glucose (4-[$^{18}F$]TFMQDG), 2-deoxy-2-(2-oxo-2H-3-[$^{11}C$]methyl-chromen-7-yl)amino-L-glucose (3-[$^{11}C$]MCLG), 2-deoxy-2-(2-oxo-2H-4-[$^{11}C$]methyl-chromen-7-yl)amino-L-glucose (4-[$^{11}C$]MCLG), 2-deoxy-2-(2-oxo-2H-3-[$^{18}F$]fluorodifluoromethyl-chromen-7-yl)amino-L-glucose (3-[$^{18}F$]=CLG), 2-deoxy-2-(2-oxo-2H-4-[$^{18}F$]fluorodifluoromethyl-chromen-7-yl)amino-L-glucose (4-[$^{18}F$]TFMCLG), 2-deoxy-2-(2-oxo-1,2-dihydro-3-[$^{11}C$]methyl-quinolin-7-yl)amino-L-glucose (3-[$^{11}C$]MQLG), 2-deoxy-2-(2-oxo-1,2-dihydro-4-[$^{11}C$]methyl-quinolin-7-yl)amino-L-glucose (4-[$^{11}C$]MQLG), 2-deoxy-2-(2-oxo-1,2-dihydro-3-[$^{18}F$]fluorodifluoromethyl-quinolin-7-yl)amino-L-glucose (3-[$^{18}F$]TFMQLG), or 2-deoxy-2-(2-oxo-1,2-dihydro-4-[$^{18}F$]fluorodifluoromethyl-quinolin-7-yl)amino-L-glucose (4-[$^{18}F$]TFMQLG).

13. A composition for imaging a target cell, comprising a glucose derivative according to any one of the above items 1 to 12.

14. A composition for imaging a target cell, comprising a glucose derivative according to the above items 3 or 4.

15. A composition for imaging a target cell, comprising a glucose derivative according to the above items 6 or 7.

16. A composition for imaging a target cell, comprising a glucose derivative according to the above item 9.

17. A composition for imaging a target cell, comprising a glucose derivative according to the above item 10.

18. The composition according to the above item 17, wherein the glucose derivative is 2-deoxy-2-(2-oxo-2H-chromen-7-yl)amino-D-glucose (CDG) or 2-deoxy-2-(2-oxo-2H-chromen-7-yl)amino-L-glucose (CLG).

19. The composition according to the above item 17, wherein the glucose derivative is 2-deoxy-2-(2-oxo-1,2-dihydroquinolin-7-yl)amino-D-glucose (QDG) or 2-deoxy-2-(2-oxo-1,2-dihydroquinolin-7-yl)amino-L-glucose (QLG).

20. A composition for imaging a target cell, comprising a radiolabeled glucose derivative according to the above item 11 or 12.

21. A method for imaging a target cell, comprising the following steps:
a. contacting a glucose derivative according to any one of the above items 1 to 12 with the target cell; and
b. detecting fluorescence emitted by the glucose derivative present within the target cell.

22. The imaging method according to the above item 21, wherein the glucose derivative is 2-deoxy-2-(2-oxo-2H-chromen-7-yl)amino-D-glucose (CDG) or 2-deoxy-2-(2-oxo-2H-chromen-7-yl)amino-L-glucose (CLG).

23. The imaging method according to the above item 21, wherein the glucose derivative is 2-deoxy-2-(2-oxo-1,2-dihydroquinolin-7-yl)amino-D-glucose (QDG) or 2-deoxy-2-(2-oxo-1,2-dihydroquinolin-7-yl)amino-L-glucose (QLG).

24. The imaging method according to any one of the above items 21 to 23, wherein the composition in the step a further comprises an additional fluorescently labeled glucose derivative, and the step b is the step of detecting at least one of the glucose derivatives present within the target cell.

25. The imaging method according to the above item 24, wherein the additional fluorescently labeled glucose derivative is at least one glucose derivative selected from the group consisting of 2-[N-(7-nitrobenz-2-oxa-1,3-diazol-4-yl)amino]-2-deoxy-D-glucose (2-NBDG), 2-[N-(7-nitrobenz-2-oxa-1,3-diazol-4-yl)amino]-2-deoxy-L-glucose (2-NBDLG), 2-deoxy-2-[N-7-(N',N'-dimethylaminosulfonyl)benz-2-oxa-1,3-diazol-4-yl)amino]-D-glucose (2-DBDG), 2-deoxy-2-[N-7-(N',N'-dimethylaminosulfonyl)benz-2-oxa-1,3-diazol-4-yl)amino]-L-glucose (2-DBDLG), and 2-amino-2-deoxy-L-glucose having a sulforhodamine (preferably sulforhodamine 101 or sulforhodamine B) bound to the 2-position through a sulfonamide bond.

26. The imaging method according to the above item 25, wherein the combination of the glucose derivatives is a combination of two glucose derivatives that respectively emit two colors selected from blue, green, and red colors as fluorescence.

27. The imaging method according to the above item 25, wherein the combination of the glucose derivatives is a combination of a glucose derivative that emits blue color as fluorescence, a glucose derivative that emits green color as fluorescence, and a glucose derivative that emits red color as fluorescence.

28. A method for detecting a cancer or a cancer cell, comprising the following steps:
a. contacting a composition containing a glucose derivative according to the above item 3 or 4 with a target cell; and
b. detecting the glucose derivative present within the target cell.

29. The detection method according to the above item 28, wherein the glucose derivative is CDG, QDG, 3-TFMCDG, 4-TFMCDG, 3-TFMQDG, or 4-TFMQDG.

30. The detection method according to the above item 29, wherein the glucose derivative is CDG.

31. A method for detecting a cancer or a cancer cell, comprising the following steps:
a. contacting a composition containing a glucose derivative according to the above item 6 or 7 with a target cell; and
b. detecting the glucose derivative present within the target cell.

32. The detection method according to the above item 31, wherein the glucose derivative is CLG, QLG, 3-TFMCLG, 4-TFMCLG, 3-TFMQLG, or 4-TFMQLG.

33. The detection method according to the above item 32, wherein the glucose derivative is CLG.

34. The detection method according to any one of the above items 28 to 33, wherein the detection in the step b is performed by imaging the target cell.

35. The detection method according to any one of the above items 28 to 34, wherein the composition in the step a further comprises an additional fluorescently labeled glucose derivative, and the step b is the step of detecting at least one of the glucose derivatives present within the target cell.

36. The detection method according to the above item 35, wherein the additional fluorescently labeled glucose derivative is at least one glucose derivative selected from the group consisting of 2-[N-(7-nitrobenz-2-oxa-1,3-diazol-4-yl)amino]-2-deoxy-D-glucose (2-NBDG), 2-[N-(7-nitrobenz-2-oxa-1,3-diazol-4-yl)amino]-2-deoxy-L-glucose (2-NBDLG), 2-deoxy-2-[N-7-(N',N'-dimethylaminosulfonyl)benz-2-oxa-1,3-diazol-4-yl)amino]-D-glucose (2-DBDG), 2-deoxy-2-[N-7-(N',N'-dimethylaminosulfonyl)benz-2-oxa-1,3-diazol-4-yl)amino]-L-glucose (2-DBDLG), and 2-amino-2-deoxy-L-glucose having a sulforhodamine (preferably sulforhodamine 101 or sulforhodamine B) bound to the 2-position through a sulfonamide bond.

37. The detection method according to the above item 36, wherein the combination of the glucose derivatives is a combination of two glucose derivatives that respectively emit two colors selected from blue, green, and red colors as fluorescence.

38. The detection method according to the above item 36, wherein the combination of the glucose derivatives is a combination of a glucose derivative that emits blue color as fluorescence, a glucose derivative that emits green color as fluorescence, and a glucose derivative that emits red color as fluorescence.

39. An imaging agent for imaging a target cancer cell, comprising a glucose derivative according to the above item 3 or 4.

40. The imaging agent according to the above item 39, wherein the glucose derivative is CDG, QDG, 4-F-CDG, 6-F-CDG, 4-F-QDG, 6-F-QDG, 3-TFMCDG, 4-TFMCDG, 3-TFMQDG, or 4-TFMQDG.

41. The imaging agent according to the above item 40, wherein the glucose derivative is CDG.

42. An imaging agent for imaging a target cancer cell, comprising a glucose derivative according to the above item 6 or 7.

43. The imaging agent according to the above item 42, wherein the glucose derivative is CLG, QLG, 4-F-CLG, 6-F-CLG, 4-F-QLG, 6-F-QLG, 3-TFMCLG, 4-TFMCLG, 3-TFMQLG, or 4-TFMQLG.

44. The imaging agent according to the above item 43, wherein the glucose derivative is CLG.

45. An imaging agent for PET examination of a cancer, comprising a radiolabeled glucose derivative according to the above item 11 or 12.

The present invention provides a novel glucose derivative, which is taken into cells via a membrane sugar transport system, and further provides an imaging method and an imaging agent capable of identifying cells or intracellular molecules with high contrast. The present invention also provides a method capable of identifying cancer cells with high contrast, and an imaging agent therefor.

BRIEF DESCRIPTION OF DRAWINGS

FIG. 2A shows the results of confirming the uptake of CDG and the influence of an inhibitor cytochalasin B (CB). FIG. 2B shows the results of confirming the uptake of CDG and the influence of an inhibitor phloretin (PHT). FIG. 2C shows the results of confirming the uptake of CDG or CLG and the influence of an inhibitor phloretin (PHT).

FIG. 5A shows the results of confirming the influence of cytochalasin B (CB). FIG. 5B shows the results of confirming the influence of phloretin (PHT).

FIGS. 6A, 6B, and 6C show the uptake into cells of blue fluorescence-emitting CDG, green fluorescence-emitting 2-NBDLG, and red fluorescence-emitting 2-TRLG, respectively. FIG. 6D is a differential interference contrast (DIC) image.

FIGS. 8A, 8B, and 8C show the uptake into cells of blue fluorescence-emitting CLG, green fluorescence-emitting 2-NBDLG, and red fluorescence-emitting 2-TRLG, respectively. FIG. 8D is a differential interference contrast (DIC) image.

FIG. 9A is an autofluorescence image taken before the administration of the mixed solution. The arrows indicate two normal neuronal cells, and * indicates the debris of killed cells. FIG. 9B shows a differential interference contrast (DIC) image superimposed on the image of FIG. 9A in order to facilitate visualizing the positions of the cells. FIG. 9C is a blue fluorescence image taken 8 minutes after the start of washout of the mixed solution. FIG. 9D is a DIC image superimposed on the image of FIG. 9C.

FIG. 10A shows autofluorescence before the administration of the mixed solution. FIG. 10B shows a differential interference contrast (DIC) image superimposed on the image of FIG. 10A in order to facilitate visualizing the positions of cells. FIG. 10C is a red fluorescence image taken 8 minutes after the start of washout of the mixed solution. FIG. 10D is a DIC image superimposed on the image of FIG. 10C. Intense red color at the central portion of each image resulting from the leakage of a portion of irradiation light to the detector side through a fluorescence filter since weak red fluorescence was photographed with sensitivity enhanced.

DESCRIPTION OF EMBODIMENTS

Figure 1:
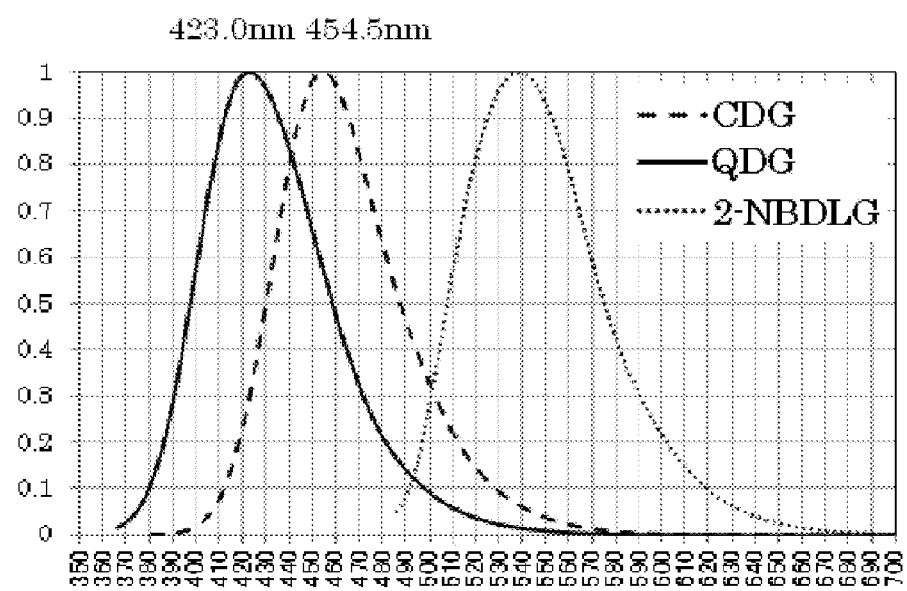
FIG. 1 shows the comparison of the fluorescence spectra of CDG, QDG, and 2-NBDLG.

In the present specification, the "target cell" is used in the meaning including the targeted cell itself and various organs or molecules present within the cell. Thus, the phrase "imaging a (target) cell" described herein is used in the meaning including imaging any one or more of the targeted cell itself and various organs or molecules present within the cell, etc.

Examples of the subject to be imaged can include such targets as cell membranes and/or intracellular regions called cytosol, subcellular small organs (so-called organelles examples of which can include the inside of structures such as nucleus, endoplasmic reticulum, Golgi body, endosome, lysosome, mitochondrion, peroxisome, autophagosome, glycosome, proteasome, vacuole, chloroplast, and glyoxysome, and/or biomembranes surrounding these structures), structures in the inside and/or on the surface of the organelles (examples of which can include nucleolus and ribosome), and molecules within the target cell (e.g., molecules present in the inside of the cell, i.e., within cytoplasm or nucleus, molecules present in the cell membrane of the target cell, and molecules present on the cell membrane of the target cell). The glucose derivative of the present invention can be used for imaging at least one of these subjects. The subject to be imaged is preferably a cell membrane and/or an intracellular region called cytosol, a subcellular small organ, or a structure in the inside and/or on the surface of subcellular organelles, particularly preferably cytosol or nucleus.

(I) Glucose Derivative

The glucose derivative of the present invention is a compound represented by the following formula (1):

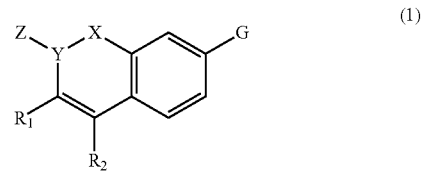

(1)

or a salt thereof.

In the formula (1), X—Y—Z represents O—C=O, NH—C=O, NR$_3$—C=O, or N=C—OR$_4$, wherein R$_3$ represents C$_1$-C$_5$ alkyl, and R$_4$ represents C$_1$-C$_5$ alkyl.

$R_1$ and $R_2$ are each independently selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl.

By virtue of the above a structure, the glucose derivative of the present invention has a fluorophore within its molecule.

In the formula (1), G represents D-amino-glucose or L-amino-glucose. The glucose derivative of the present invention has a fluorophore via an amino group at the 2- or 6-position of glucose and preferably has a fluorophore via the amino group at the 2-position. Specifically, G is any of the structures of the following formulas (G1) to (G4):

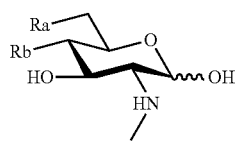

G1

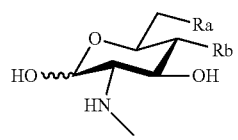

G2

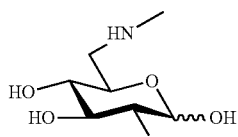

G3

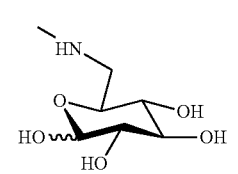

G4

In these formulas, Ra and Rb each represent hydroxy or fluorine. When one of Ra and Rb is fluorine, the other group is hydroxy. Preferably, both of Ra and Rb are hydroxy.

In the formula (1) which represents the glucose derivative of the present invention, X—Y—Z is O—C=O, NH—C=O, NR$_3$—C=O, or N=C—OR$_4$ (wherein R$_3$ is $C_1$-$C_5$ alkyl, and R$_4$ is $C_1$-$C_5$ alkyl), preferably O—C=O, NH—C=O, or N(CH$_3$)—C=O, particularly preferably O—C=O or NH—C=O.

In the formula (1) which represents the glucose derivative of the present invention, $R_1$ and $R_2$ are each independently selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl, and, preferably, $R_1$ and $R_2$ are each independently hydrogen, halogen, $C_1$-$C_5$ alkyl, $C_2$-$C_5$ alkenyl, $C_2$-$C_5$ alkynyl, or $C_1$-$C_5$ haloalkyl, more preferably, $R_1$ and $R_2$ are each independently hydrogen, $C_1$-$C_5$ alkyl, or $C_1$-$C_5$ haloalkyl, further preferably, $R_1$ and $R_2$ are each independently hydrogen, methyl, or fluoromethyl, and particularly preferably, $R_1$ and $R_2$ are hydrogen.

A feature of the glucose derivative of the present invention is that the fluorophore is directly bound to the 2- or 6-position of glucose via NH. As a result, the glucose derivative of the present invention is taken into cells via a membrane sugar transport system such as GLUT.

A preferred form of the glucose derivative of the present invention is any of the following compounds:

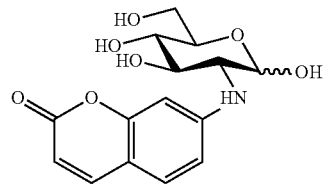

CDG

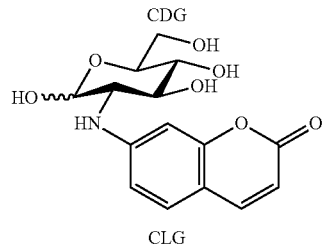

CLG

2-Deoxy-2-(2-oxo-2H-chromen-7-yl)amino-D-glucose (referred to as CDG) (D-glucose derivative) and 2-deoxy-2-(2-oxo-2H-chromen-7-yl)amino-L-glucose (referred to as CLG) (L-glucose derivative) are in the relationship of enantiomers. Their maximum excitation wavelength (Ex max) and maximum fluorescence wavelength (Em max) are 366.5 nm (Ex max) and 454.5 nm (Em max).

Another preferred form of the glucose derivative of the present invention is any of the following compounds:

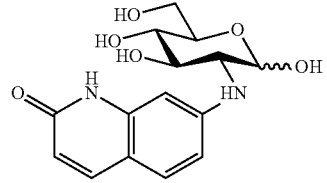

QDG

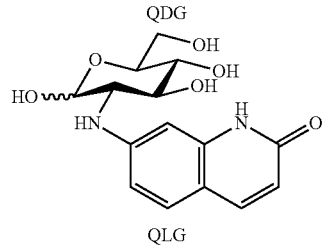

QLG

2-Deoxy-2-(2-oxo-1,2-dihydroquinolin-7-yl)amino-D-glucose (referred to as QDG) (D-glucose derivative) and 2-deoxy-2-(2-oxo-1,2-dihydroquinolin-7-yl)amino-L-glucose (referred to as QLG) (L-glucose derivative) are in the relationship of enantiomers. Their maximum excitation wavelength (Ex max) and maximum fluorescence wavelength (Em max) are 353.5 nm (Ex max) and 423.0 nm (Em max).

Further examples of the preferred form of the glucose derivative of the present invention can include compounds having a substituent at the 3- or 4-position of the coumarin backbone or quinoline backbone in CDG, CLG, QDG, or QLG described above. Examples of the substituent can include halogen, acetyl, formyl, allyl, ethynyl, propenyl, methyl, fluoromethyl, cycloalkyl, phenyl, pyridyl, thiophenyl, pyrrolyl, and furanyl. The substituent is particularly preferably methyl or fluoromethyl.

Examples of the preferred form of the glucose derivative of the present invention can include the following compounds.

TABLE 1

| Compound No. | Structure |
| --- | --- |
| Compound 101 CDG | 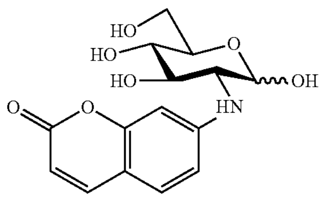 |
| Compound 102 | 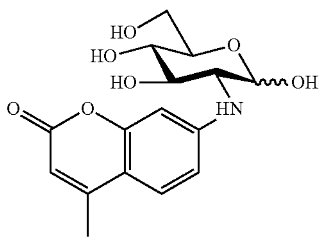 |
| Compound 103 | 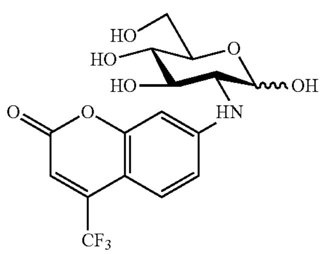 |
| Compound 104 | 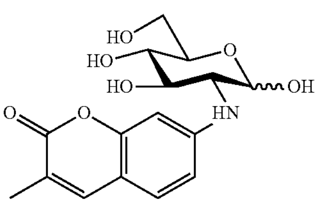 |
| Compound 105 | 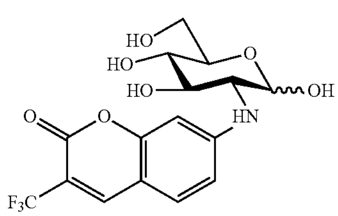 |
| Compound 106 | 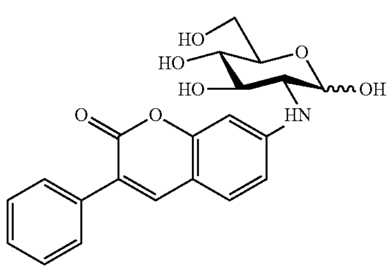 |

TABLE 1-continued

| Compound No. | Structure |
| --- | --- |
| Compound 107 | 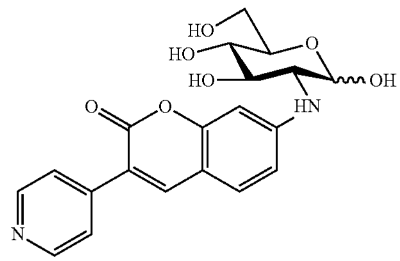 |
| Compound 108 | 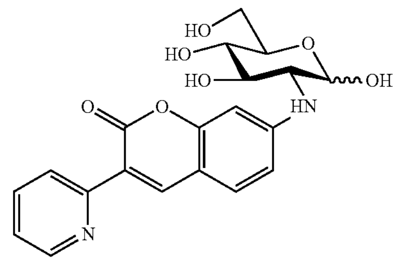 |
| Compound 201 CLG | 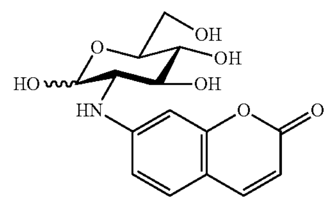 |
| Compound 202 | 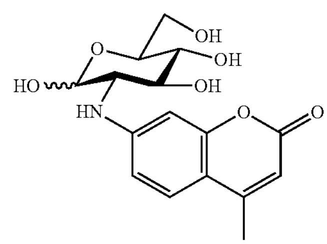 |
| Compound 203 | 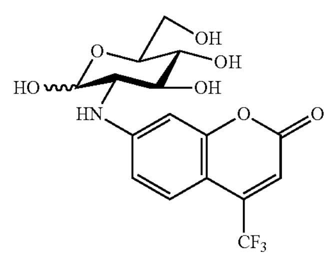 |
| Compound 204 | 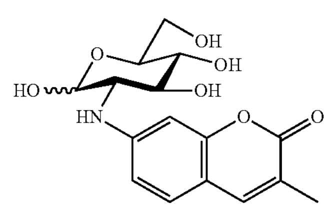 |

TABLE 1-continued

| Compound No. | Structure |
| --- | --- |
| Compound 205 | (glycosylamino-coumarin with 3-CF₃ substituent) |
| Compound 206 | (glycosylamino-coumarin with 3-phenyl substituent) |
| Compound 207 | (glycosylamino-coumarin with 3-(pyridin-4-yl) substituent) |
| Compound 208 | (glycosylamino-coumarin with 3-(pyridin-2-yl) substituent) |

TABLE 2

| Compound No. | Structure |
| --- | --- |
| Compound 109 | (7-glycosylamino-3-(thiophen-2-yl)-coumarin) |
| Compound 110 | (7-glycosylamino-3-(furan-2-yl)-coumarin) |
| Compound 111 | (7-glycosylamino-3-(1H-pyrrol-2-yl)-coumarin) |
| Compound 112 | (7-glycosylamino-4-methyl-3-phenyl-coumarin) |
| Compound 113 | (7-glycosylamino-4-methyl-3-(pyridin-4-yl)-coumarin) |
| Compound 114 | (7-glycosylamino-4-methyl-3-(thiophen-2-yl)-coumarin) |
| Compound 115 | (7-glycosylamino-4-methyl-3-(furan-2-yl)-coumarin) |
| Compound 209 | (glycosylamino-coumarin with 3-(thiophen-2-yl) substituent) |

TABLE 2-continued
Compound 210
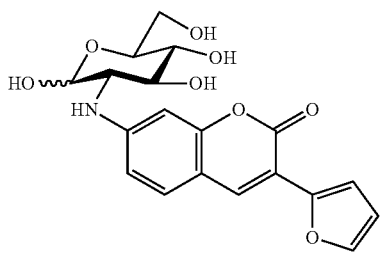
Compound 211
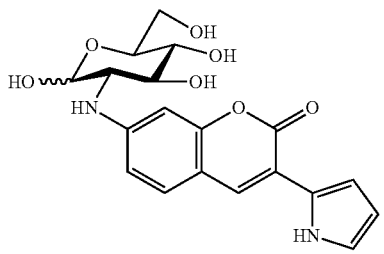
Compound 212
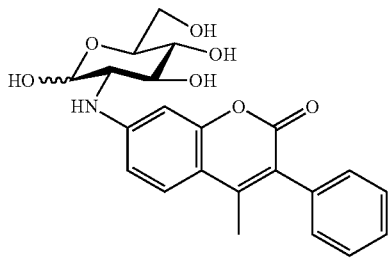
Compound 213
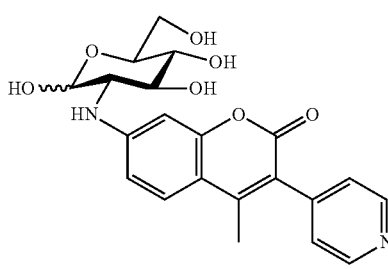
Compound 214
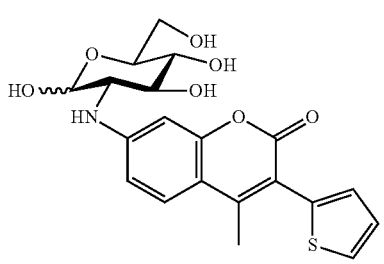
Compound 215
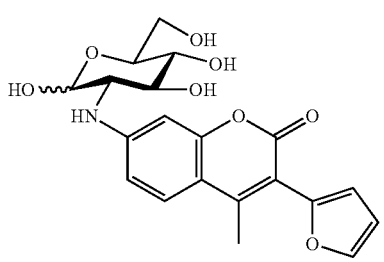
TABLE 3
Compound 116
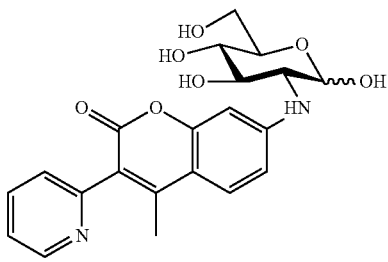
Compound 117
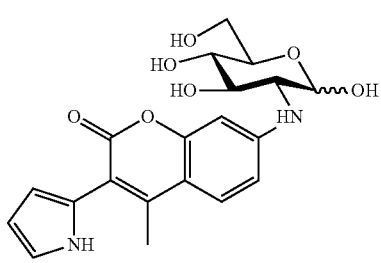
Compound 118
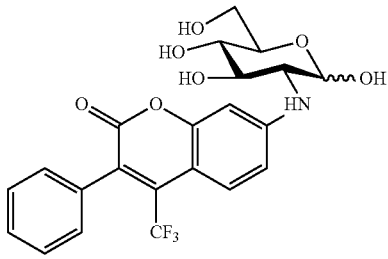
Compound 119
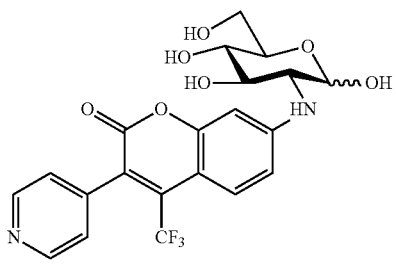
Compound 120
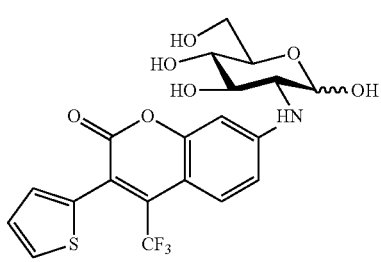
Compound 121
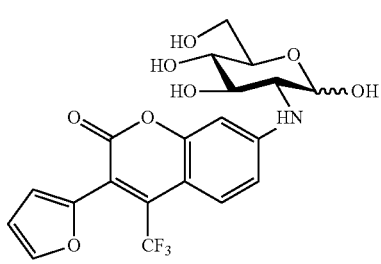

TABLE 3-continued
Compound 122
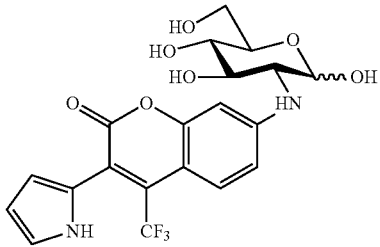
Compound 216
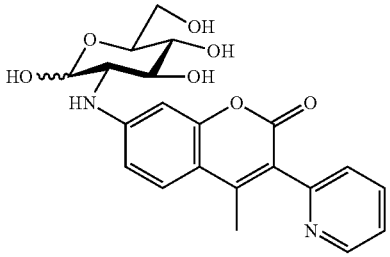
Compound 217
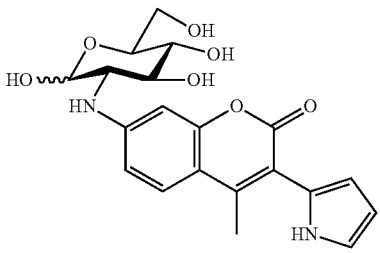
Compound 218
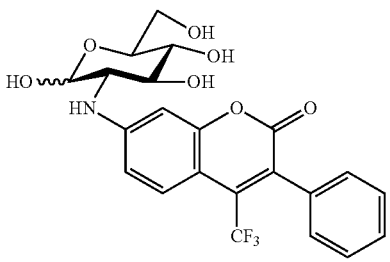
Compound 219
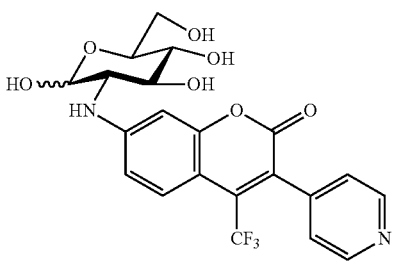
Compound 220
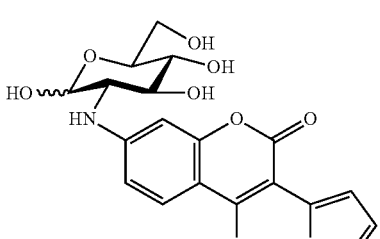
TABLE 3-continued
Compound 221
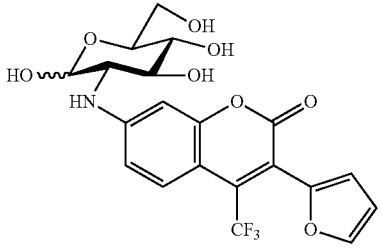
Compound 222
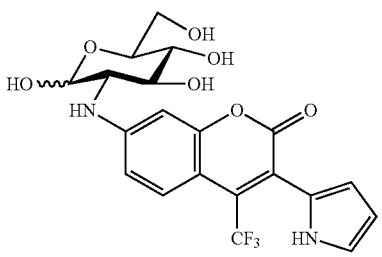
TABLE 4
Compound 123
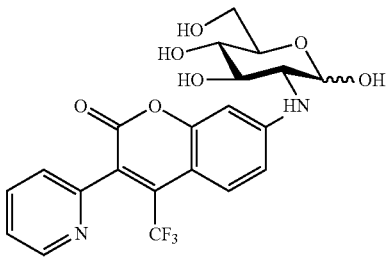
Compound 124
QDG
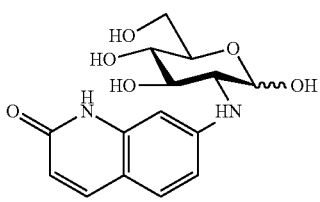
Compound 125
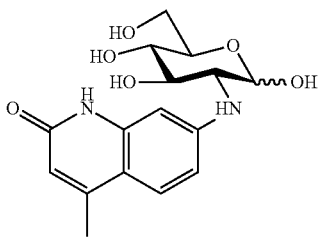
Compound 126
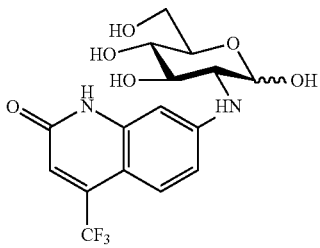

TABLE 4-continued
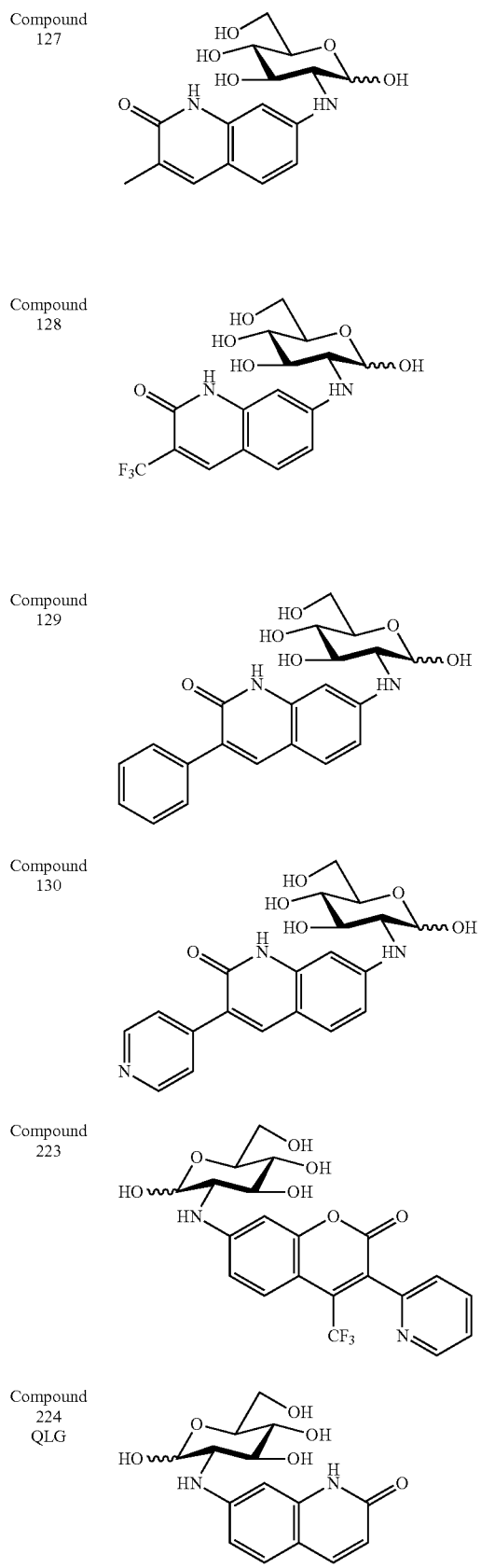
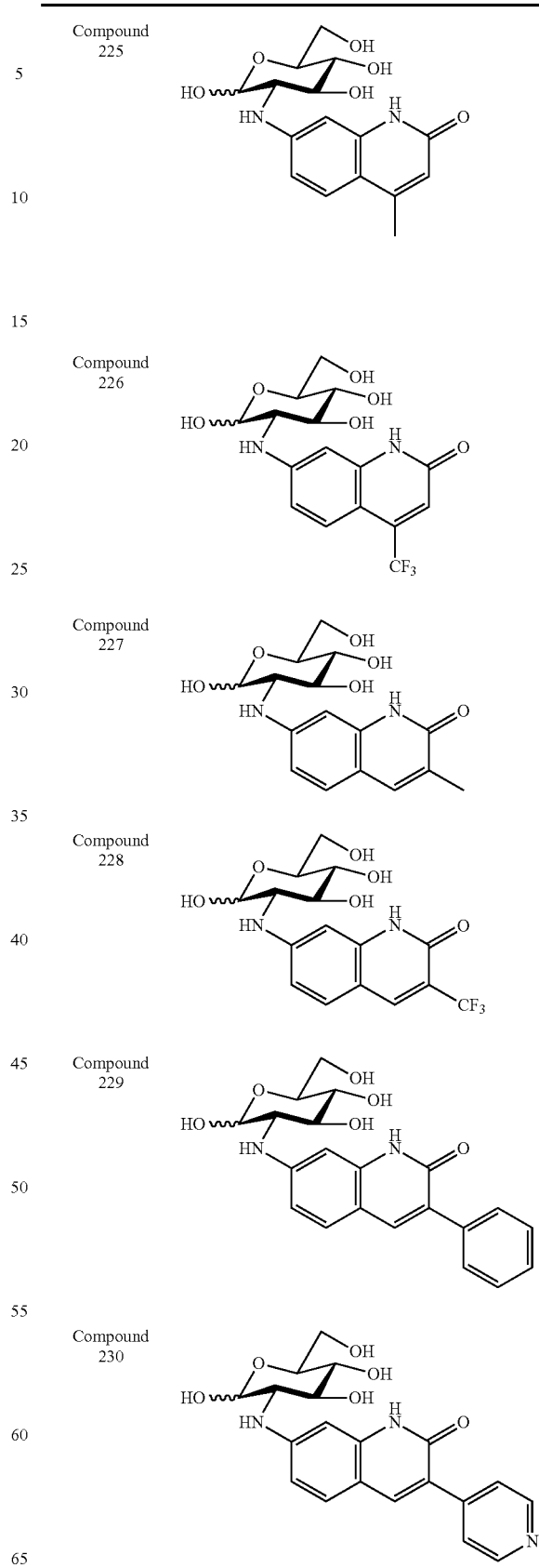

TABLE 5
| Compound 131 | 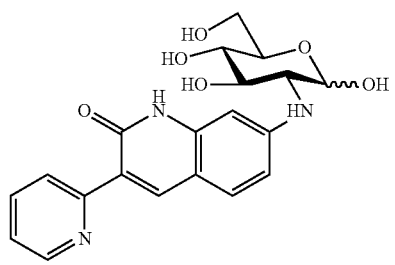 |
| --- | --- |
| Compound 132 | 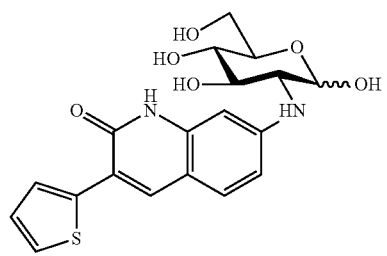 |
| Compound 133 | 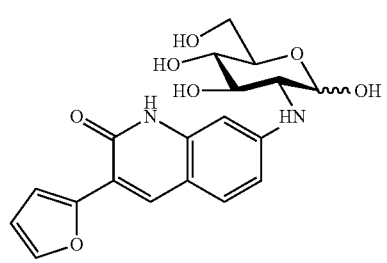 |
| Compound 134 | 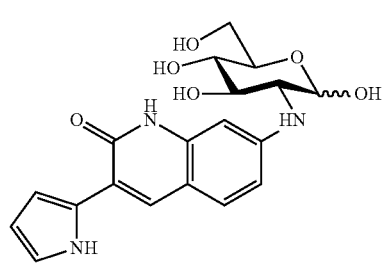 |
| Compound 135 | 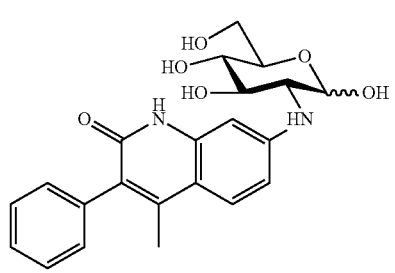 |
| Compound 136 | 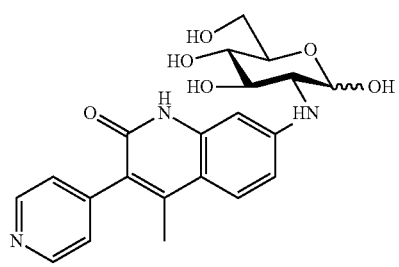 |
TABLE 5-continued
| Compound 137 | 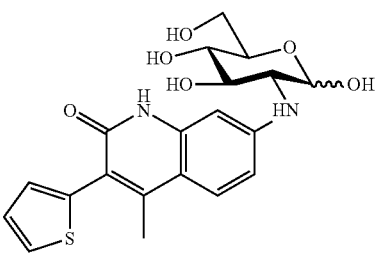 |
| --- | --- |
| Compound 231 | 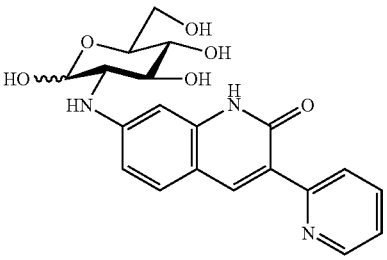 |
| Compound 232 | 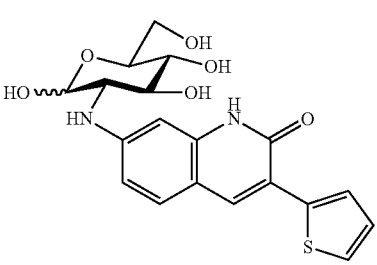 |
| Compound 233 | 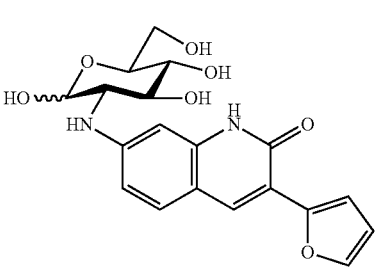 |
| Compound 234 | 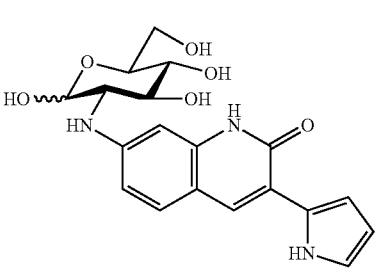 |
| Compound 235 | 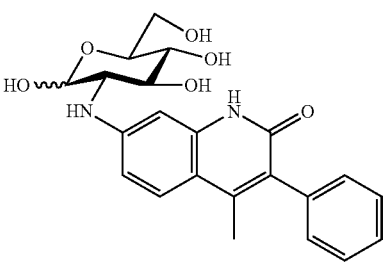 |

TABLE 5-continued
Compound 236
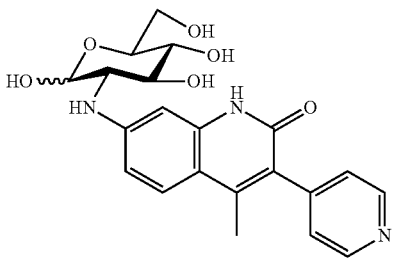
Compound 237
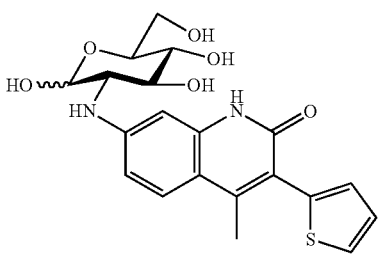
TABLE 6
Compound 138
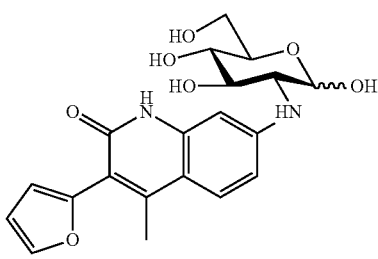
Compound 139
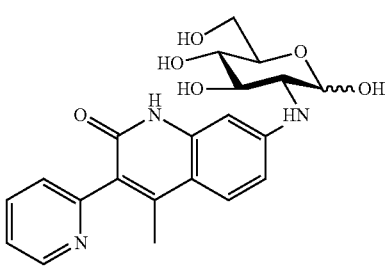
Compound 140
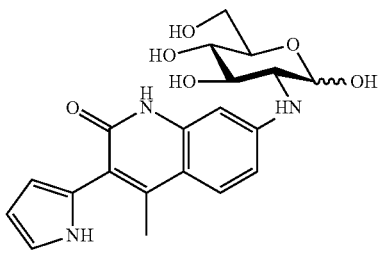
TABLE 6-continued
Compound 141
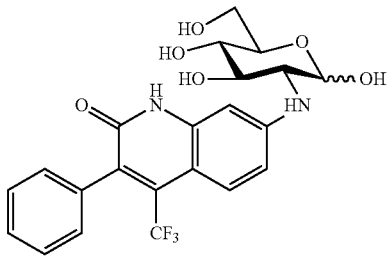
Compound 142
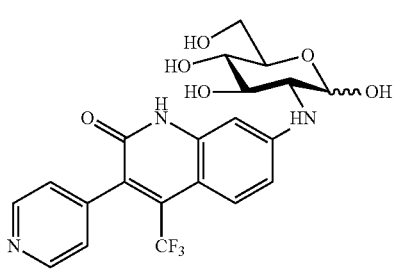
Compound 143
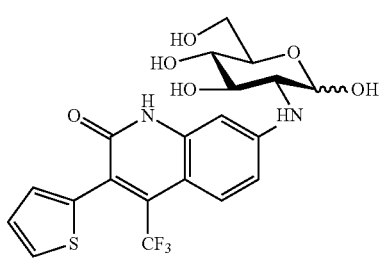
Compound 144
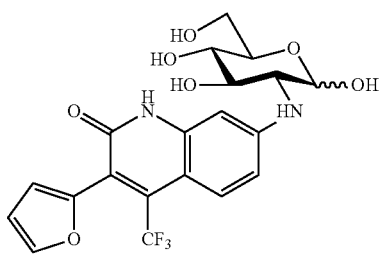
Compound 238
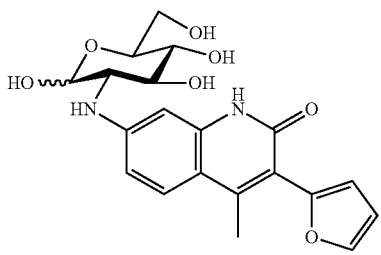
Compound 239
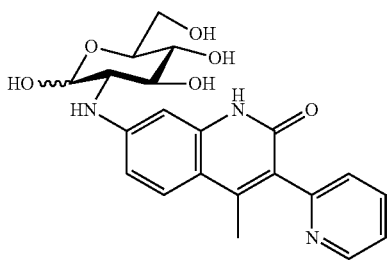

TABLE 6-continued
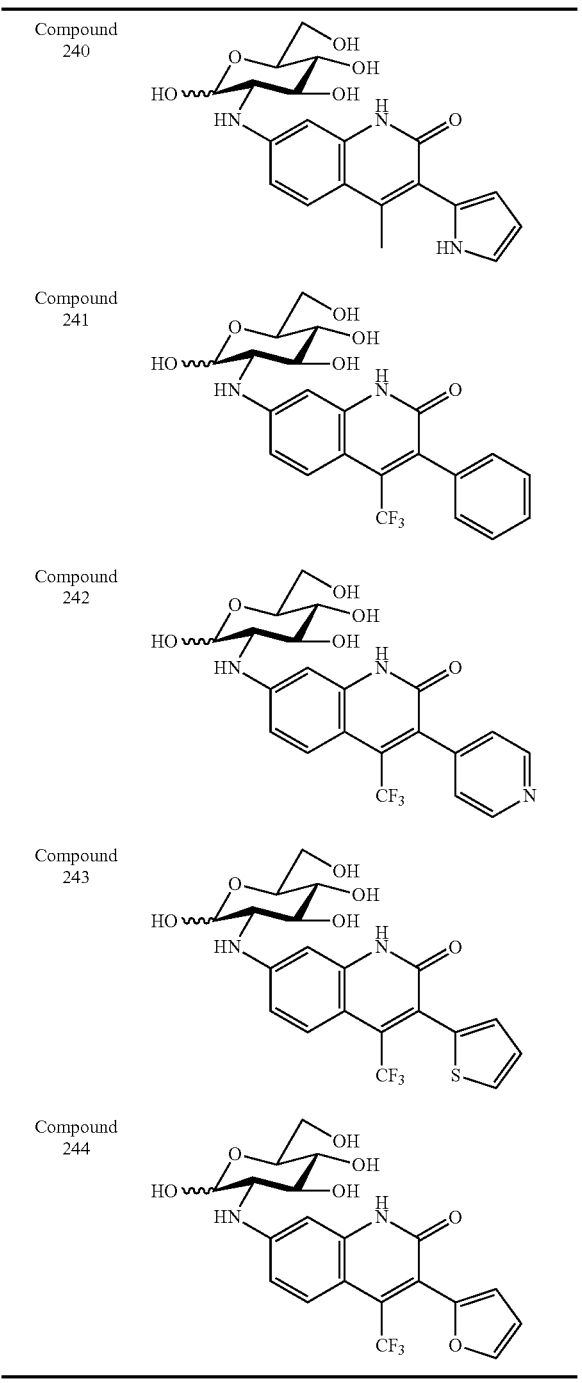
TABLE 7
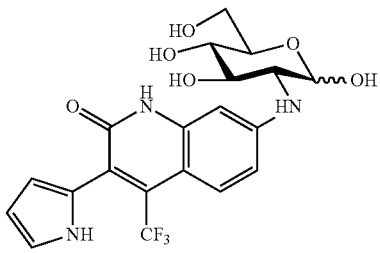
TABLE 7-continued
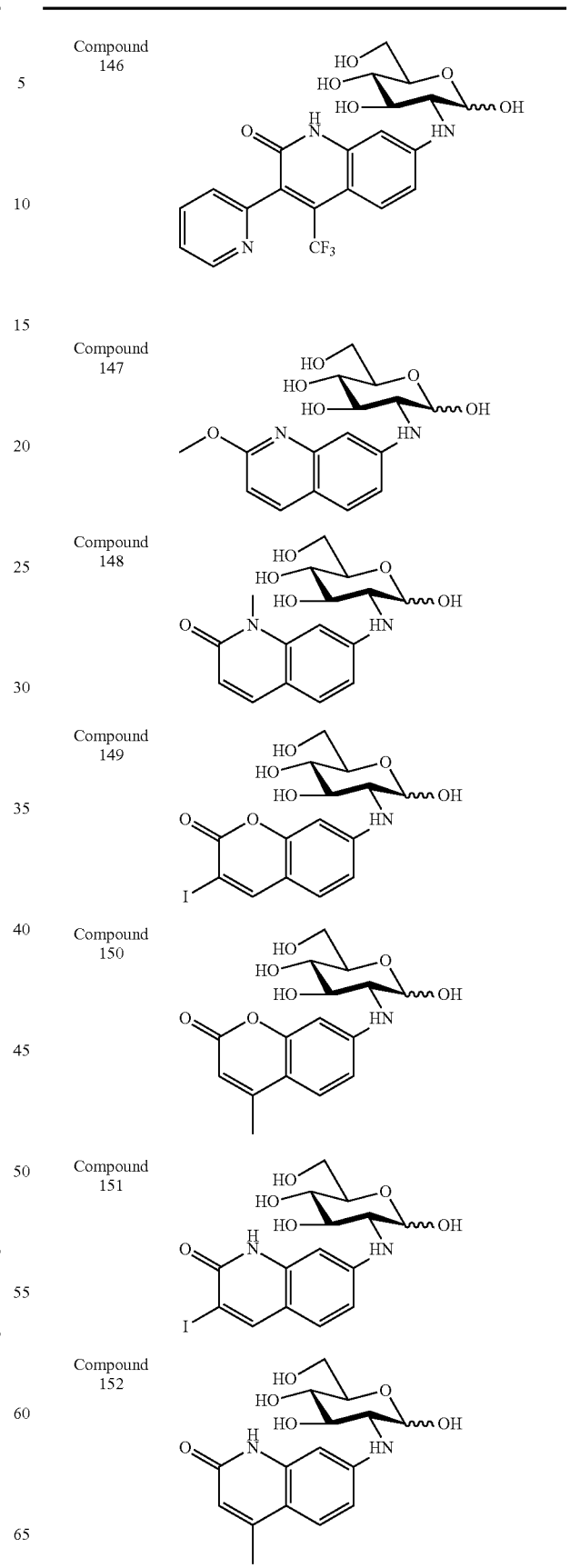

TABLE 7-continued
Compound 245
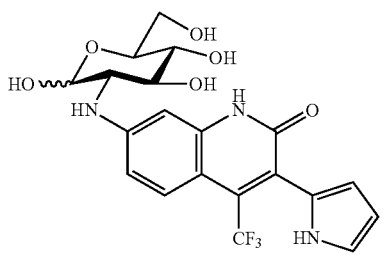
Compound 246
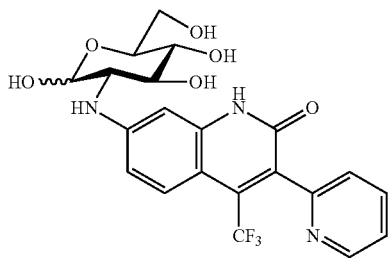
Compound 247
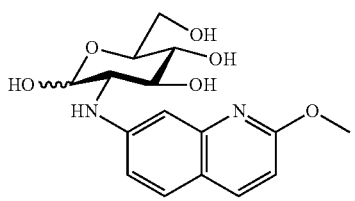
Compound 248
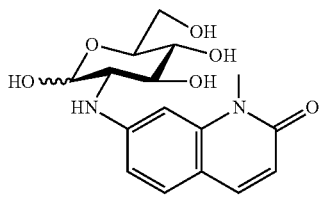
Compound 249
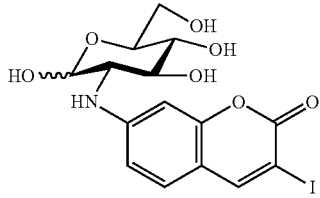
Compound 250
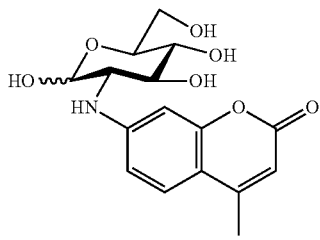
Compound 251
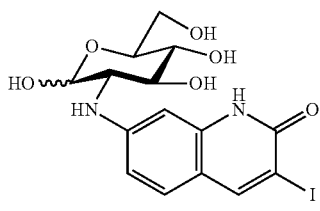
TABLE 7-continued
Compound 252
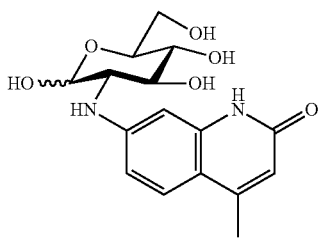
TABLE 8
Compound 153
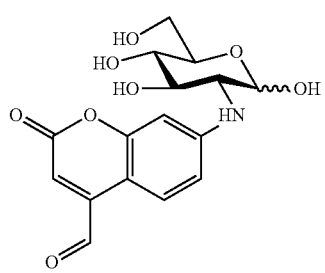
Compound 154
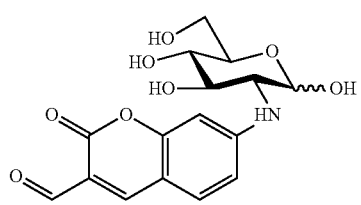
Compound 155
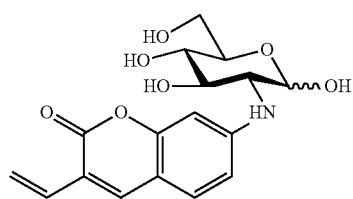
Compound 156
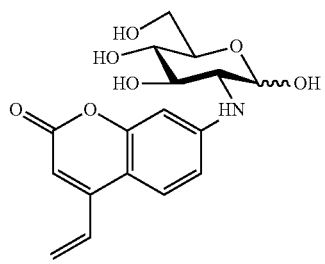
Compound 157
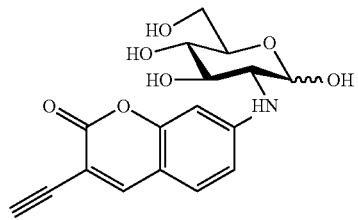

TABLE 8-continued
Compound 158
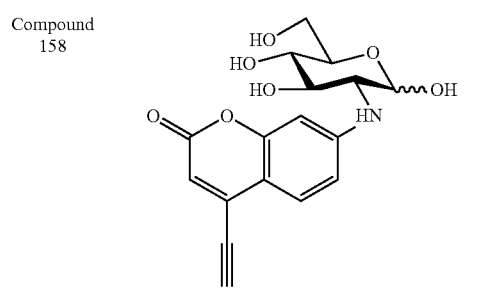
Compound 159
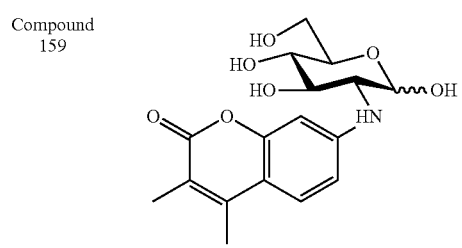
Compound 160
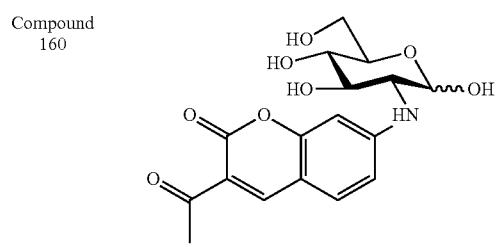
Compound 253
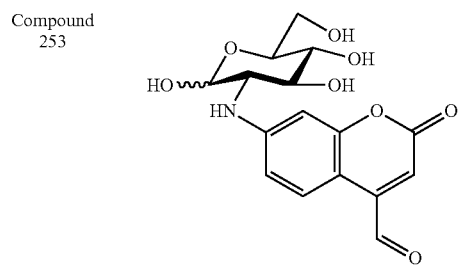
Compound 254
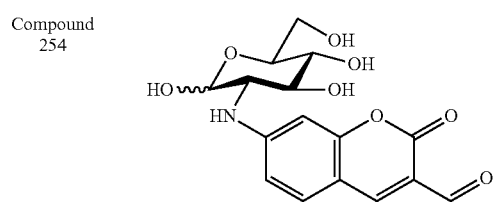
Compound 255
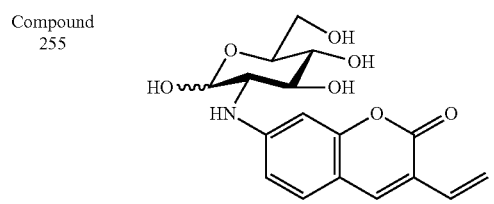
TABLE 8-continued
Compound 256
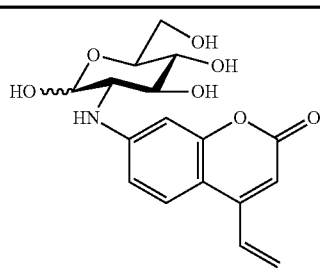
Compound 257
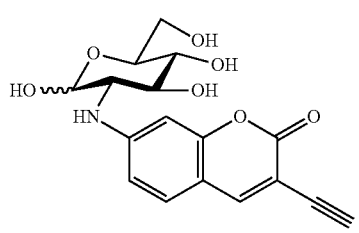
Compound 258
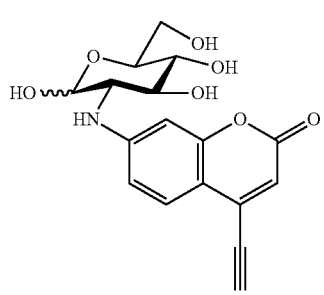
Compound 259
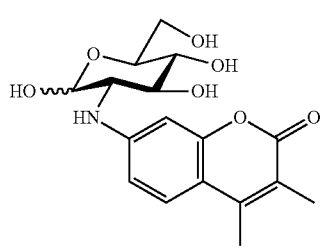
Compound 260
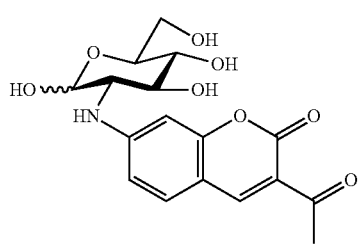
TABLE 9
Compound 161
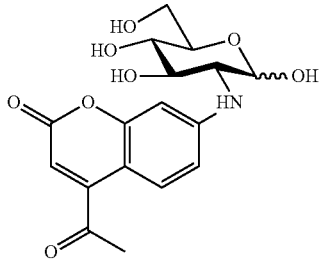

TABLE 9-continued
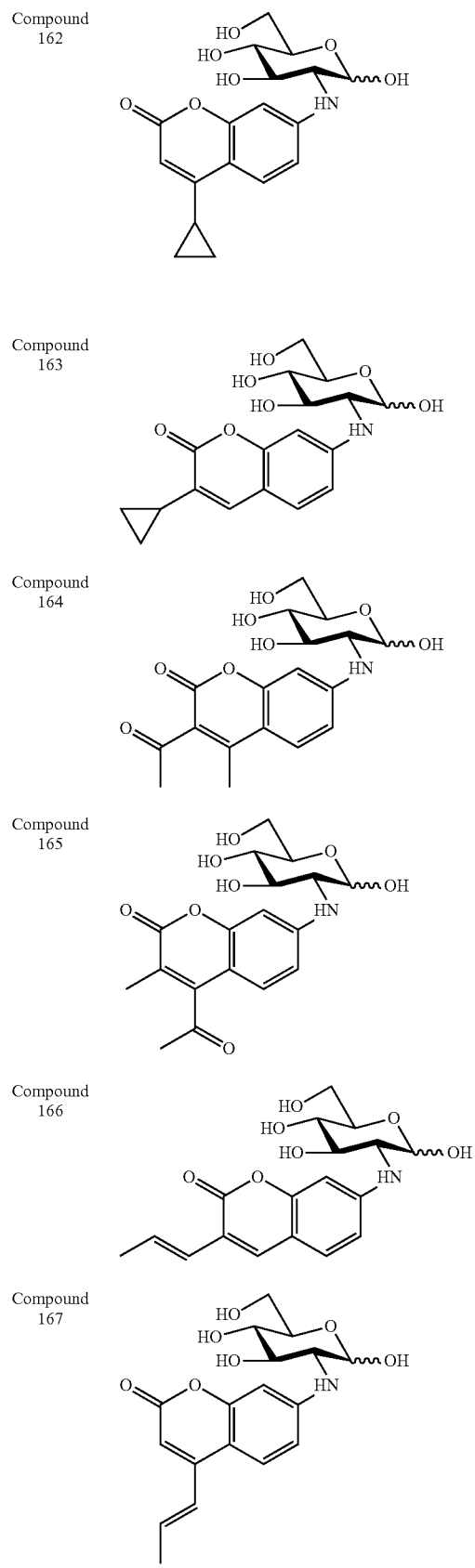
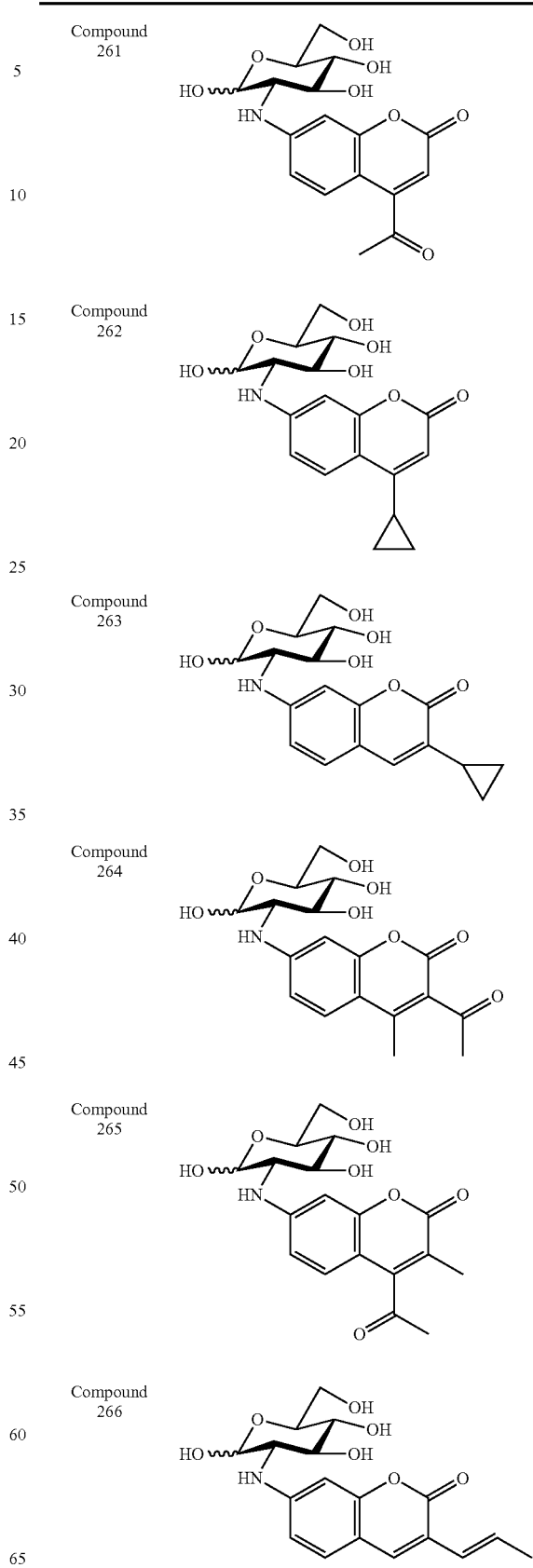

TABLE 9-continued
Compound 267
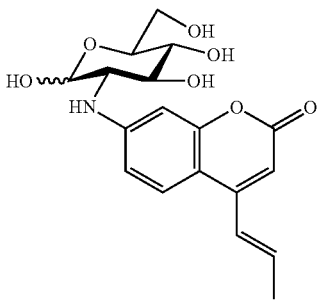
TABLE 10
Compound 168
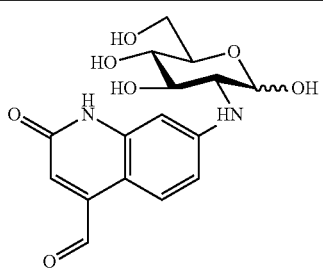
Compound 169
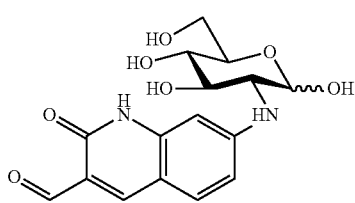
Compound 170
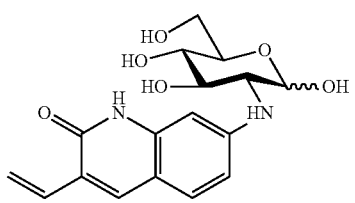
Compound 171
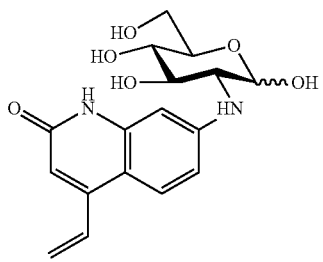
Compound 172
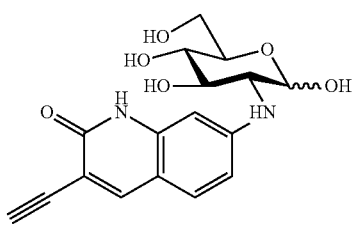
TABLE 10-continued
Compound 173
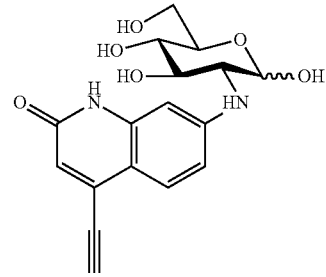
Compound 174
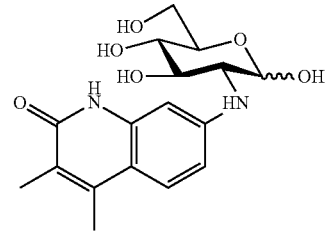
Compound 175
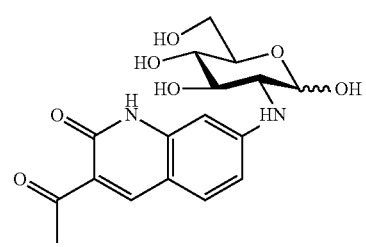
Compound 268
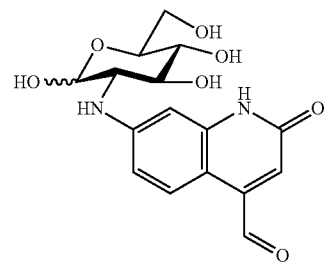
Compound 269
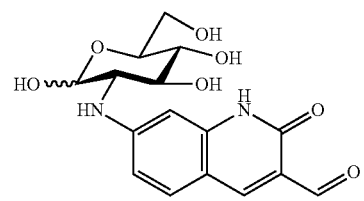
Compound 270
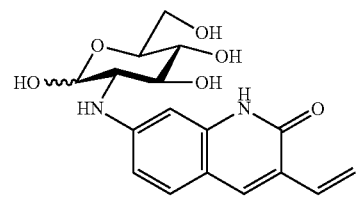

TABLE 10-continued
Compound 271 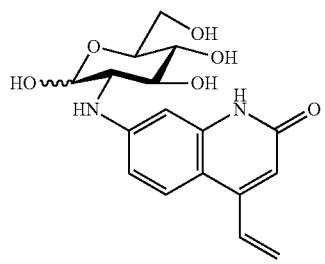
Compound 272 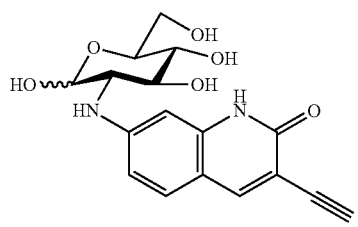
Compound 273 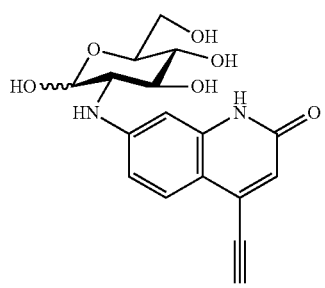
Compound 274 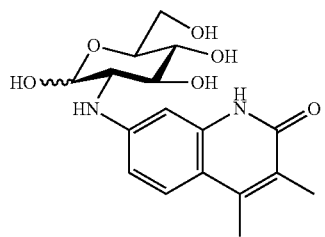
Compound 275 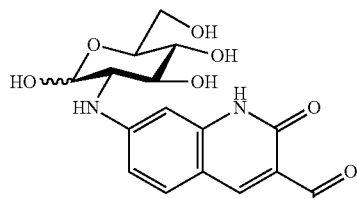
TABLE 11
Compound 176 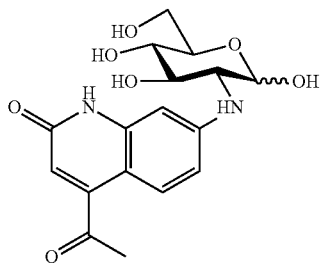
TABLE 11-continued
Compound 177 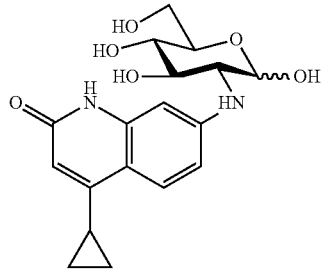
Compound 178 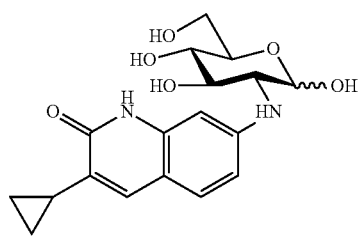
Compound 179 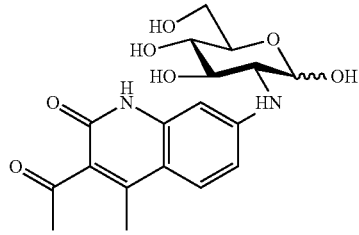
Compound 180 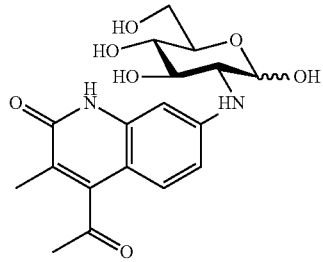
Compound 181 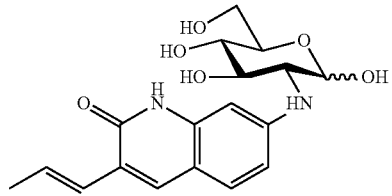
Compound 182 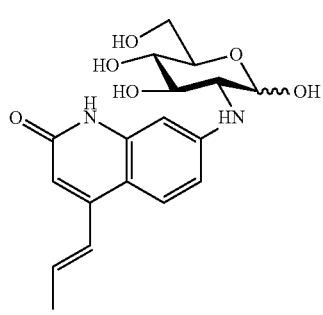

TABLE 11-continued

| Compound 276 | 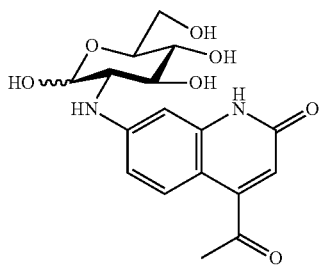 |
| Compound 277 | 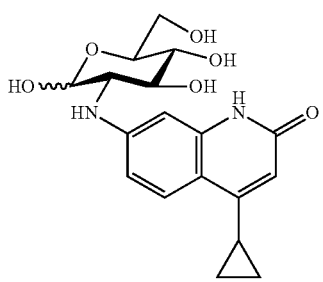 |
| Compound 278 | 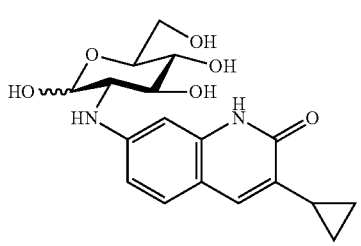 |
| Compound 279 | 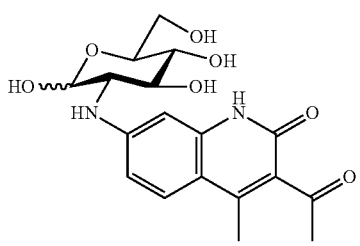 |
| Compound 280 | 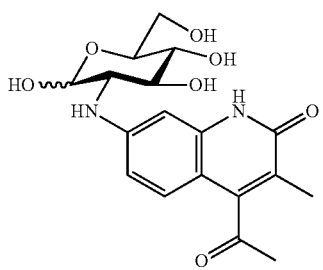 |
| Compound 281 | 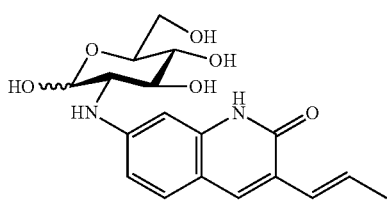 |

TABLE 11-continued

| Compound 282 | 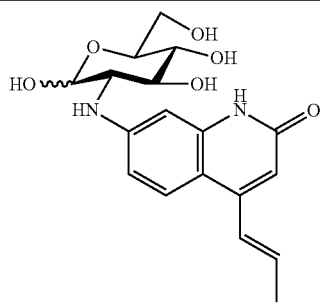 |

The glucose derivative of the present invention is particularly preferably selected from CDG, CLG, QDG, and QLG.

The glucose derivative of the present invention can be used after being dissolved in an arbitrary solution, for example, a solvent such as water or aqueous dimethyl sulfoxide. Also, the glucose derivative of the present invention is stable even in a solvent or solution used for the imaging of cells or intracellular molecules, particularly, in a buffer solution, and as such, is suitable as an imaging agent.

Hereinafter, a method for synthesizing the D-glucose derivative of the present invention will be mainly described. The L-glucose derivative of the present invention can be synthesized by using an L-form of sugar as a starting material.

The binding position of the fluorescent molecular group having a coumarin backbone or a quinoline backbone to glucose is either the 2- or 6-position of glucose, preferably the 2-position. The 2-substituted derivative can be synthesized using glucosamine, and the 6-substituted derivative can be synthesized using a 6-deoxy-6-amino-glucose derivative.

D-Glucosamine or L-glucosamine can be used as the glucosamine. Synthesized D-glucosamine or commercially available D-glucosamine can be used as the D-glucosamine. The L-glucosamine can be synthesized by a method described in WO2010/16587 (Patent Literature 2) or a method described in WO2012/133688 (Patent Literature 4) (the description of these bulletins or publications of the applications are incorporated herein by reference). The method for synthesizing L-glucosamine described in WO2012/133688 is as follows:

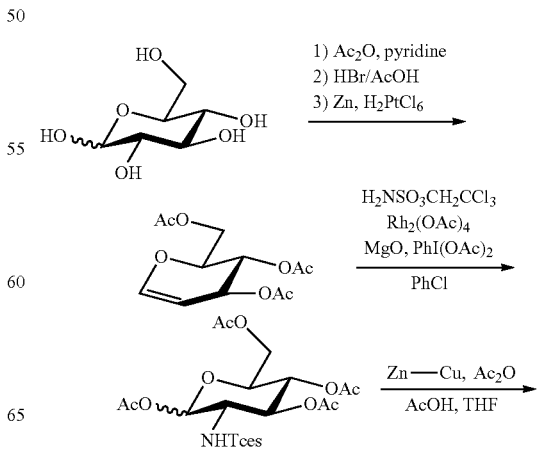

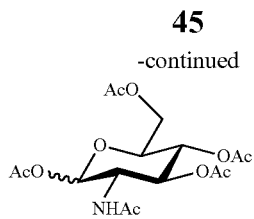

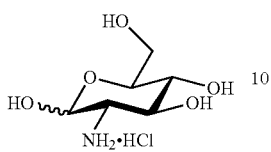

The 6-deoxy-6-amino-glucose derivative can be synthesized, for example, through 7 stages from glucose as follows, though the synthesis method is not limited thereto. The 6-deoxy-6-amino-glucose derivative can be synthesized by converting the hydroxy group at the 1-position of glucose to methyl glycoside, protecting the 4- and 6-positions with benzylidene groups and the 2- and 3-positions with isopropylidene groups, deprotecting the benzylidene groups, converting the 6-position to a toluenesulfonyl group and then to an azide group, and reducing the azide group to an amino group. Commercially available D-glucose or commercially available L-glucose can be used as the glucose.

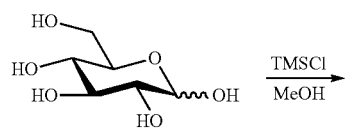

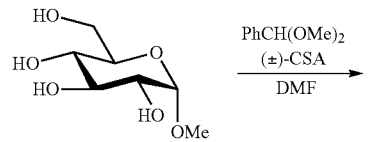

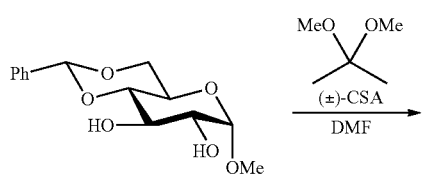

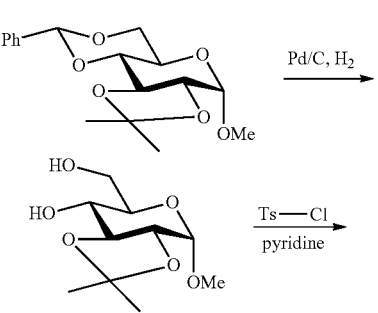

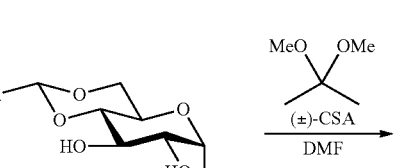

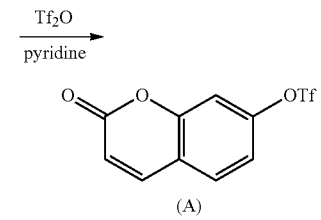

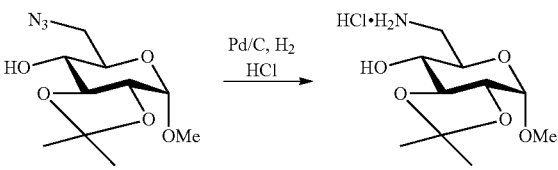

The D-glucose derivative of the present invention can be synthesized, for example, as follows, though the synthesis method is not limited thereto.

Compound (A) is synthesized which is a compound having, as a fluorophore, a coumarin backbone substituted at the 7-position with an active group. The compound (A) is synthesized by binding a trifluoromethanesulfonyl group to the hydroxy group at the 7-position.

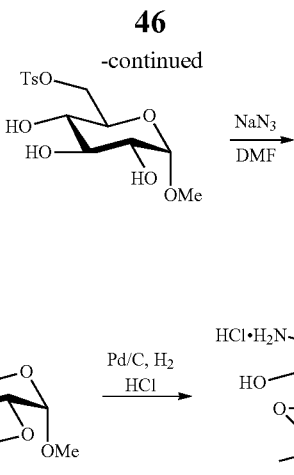

(A)

Compound (B) is synthesized which is a compound having, a fluorophore, a quinolinone backbone substituted at the 7-position with an active group. This compound is synthesized through 2 stages from an aniline derivative substituted at the 3-position with iodine.

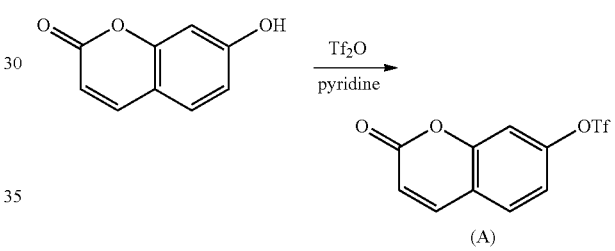

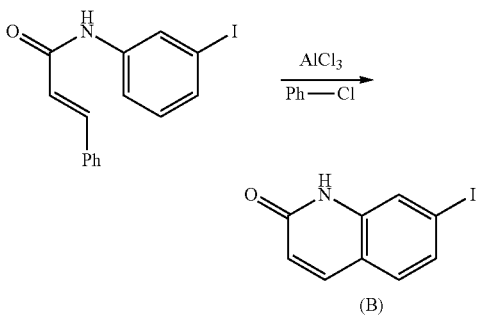

(B)

Aside therefrom, D-glucosamine having protected OH at the 1-, 4-, and 6-positions is synthesized, for example, as follows:

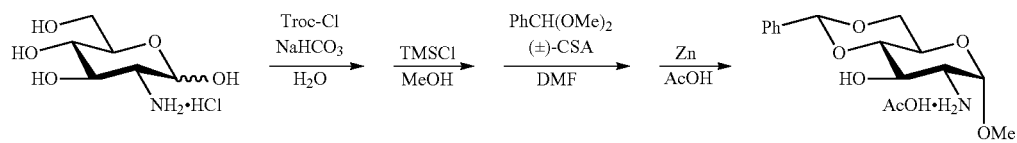

Subsequently, a synthesis can be performed by condensing the compound A and the D-glucosamine having protected OH at the 1- and 6-positions, for example, by C—N cross-coupling reaction using palladium, so as to bond the compound A to D-glucose via —NH—

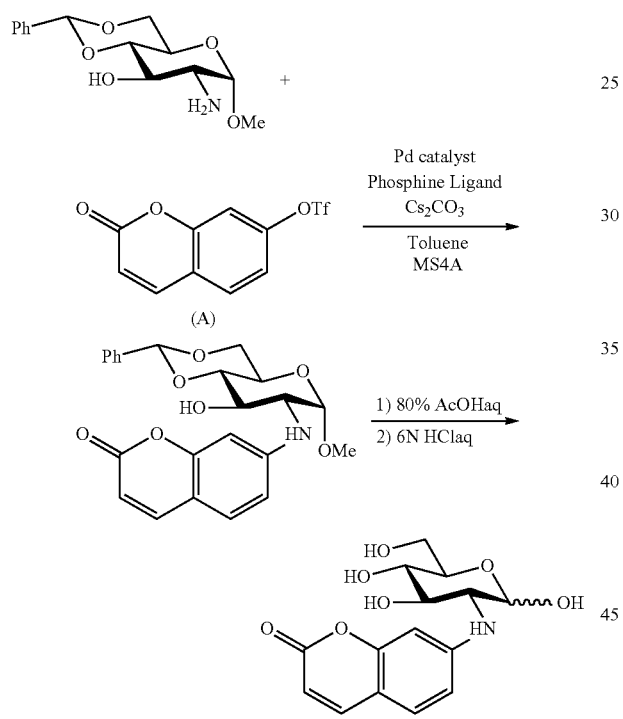

The D-glucose derivative of the present invention having a coumarin backbone or quinoline backbone at the 6-position of glucose can be synthesized by condensing the compound A and the 6-deoxy-6-amino-D-glucose derivative having protected OH at the 1-, 2-, and 3-positions, for example, by C—N cross-coupling reaction using palladium, so as to bond the compound A to D-glucose via —NH—.

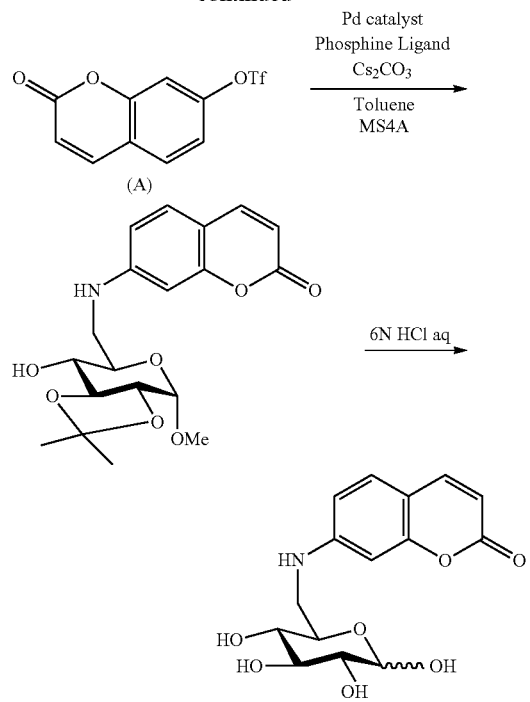

The L-glucose derivative of the present invention can be synthesized in the same way as above by using L-glucosamine instead of D-glucosamine.

The glucose derivative having a coumarin backbone or quinoline backbone having a substituent at the 3- or 4-position can be synthesized, for example, by a Suzuki coupling method using CDG, CLG, QDG, or QLG synthesized according to a method disclosed herein, or by synthesizing a compound (A) having a coumarin backbone or quinoline backbone having a substituent at the 3- or 4-position and then reacting the compound (A) with glucosamine by use of a direct introduction method by C—H activation, though the synthesis method is not limited thereto.

Hereinafter, a method for synthesizing a D-glucose derivative which has a coumarin with an aromatic group bound at the 3-position thereof will be illustrated.

(i) Suzuki Coupling Method:

-continued

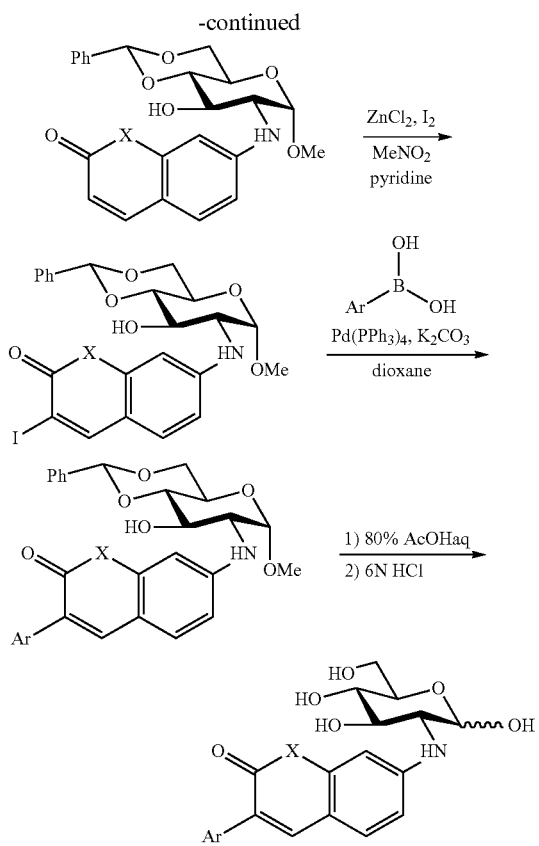

Ar = phenyl, pyridyl, thiophenyl, pyrrolyl, furanyl
X = O or NH (ii) Direct Introduction Method by C—H Activation:

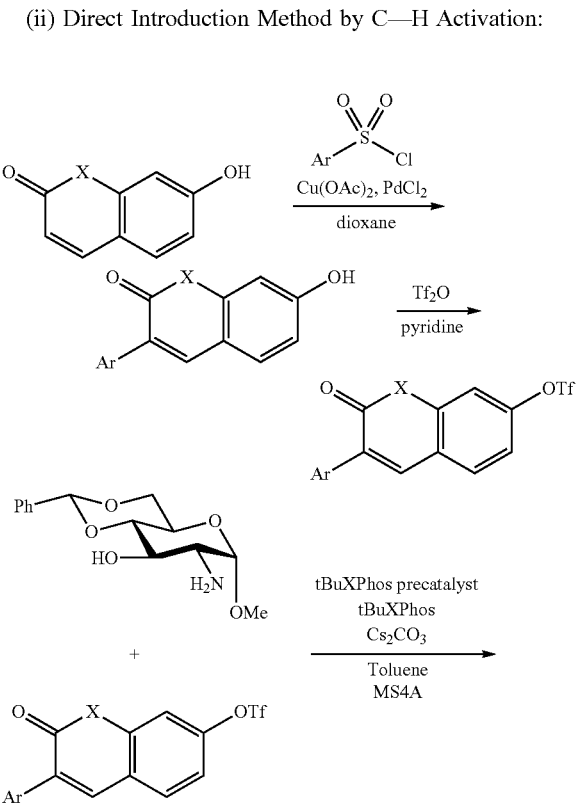

-continued

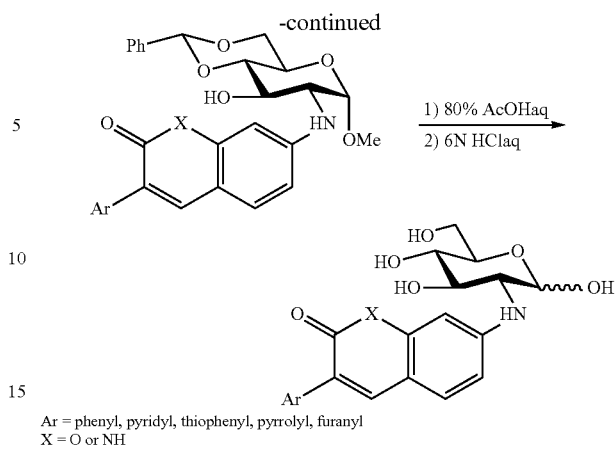

Ar = phenyl, pyridyl, thiophenyl, pyrrolyl, furanyl
X = O or NH

A radiolabel can also be added to the glucose derivative of the present invention. As a result, imaging based on radioactivity, for example, PET imaging, can also be achieved. In addition, such a compound also permits imaging in a dual mode using fluorescence and radiation.

Examples of the method for adding a radiolabel to the glucose derivative of the present invention can include a method of substituting a hydroxy group of glucose by $^{18}$F, and a method of radiolabeling a substituent in the coumarin backbone or quinoline backbone.

In the former case, the position of the hydroxy group to be substituted by $^{18}$F is the 4- or 6-position when the coumarin backbone or quinoline backbone resides at the 2-position of glucose, or is the 2- or 4-position when the coumarin backbone or quinoline backbone resides at the 6-position of glucose. Examples of the resulting glucose derivative can include 4-$^{18}$F-CDG, 4-$^{18}$F-CLG, 6-$^{18}$F-CDG, 6-$^{18}$F-CLG, 4-$^{18}$F-QDG, 4-$^{18}$F-QLG, 6-$^{18}$F-QDG, and 6-$^{18}$F-QLG.

In the latter case, examples of the radiolabeled glucose derivative can include a compound in which the carbon atom of the methyl group bound to the 3- or 4-position of the coumarin backbone or quinoline backbone is substituted by $^{11}$C, and a compound in which one of the fluorine atoms of the trifluoromethyl group bound to the 3- or 4-position of the coumarin backbone or quinoline backbone is substituted by $^{18}$F. Examples thereof can include 3-[$^{11}$C]MCDG, 4-[$^{11}$C]MCDG, 3-[$^{18}$F]TFMCDG, 4-[$^{18}$F]TFMCDG, 3-[$^{11}$C]MQDG, 4-[$^{11}$C]MQDG, 3-[$^{18}$F]TFMQDG, 4-[$^{18}$F]TFMQDG, 3-[$^{11}$C]MCLG, 4-[$^{11}$C]MCLG, 3-[$^{18}$F]TFMCLG, 4-[$^{18}$F]TFMCLG, 3-[$^{11}$C]MQLG, 4-[$^{11}$C]MQLG, 3-[$^{18}$F]TFMQLG, and 4-[$^{18}$F]TFMQLG.

Such a radiolabeled glucose derivative can be synthesized, for example, as follows, though the synthesis method is not limited thereto.

(i) Method for Synthesizing a Compound Containing a Radioisotope $^{18}$F at 6-Position of Glucose For example, the following compound (6-$^{18}$F-CLG) can be synthesized, for example, by steps given below.

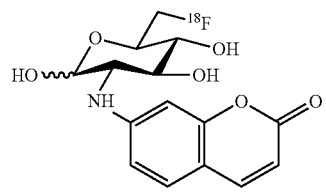

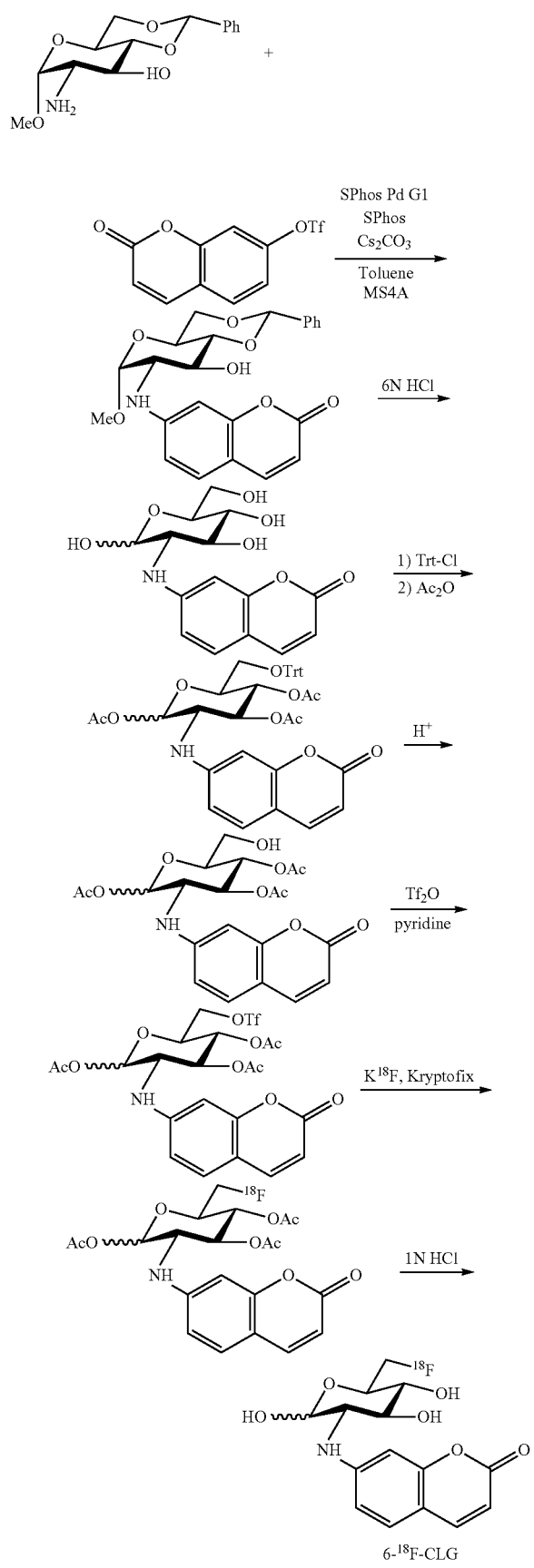
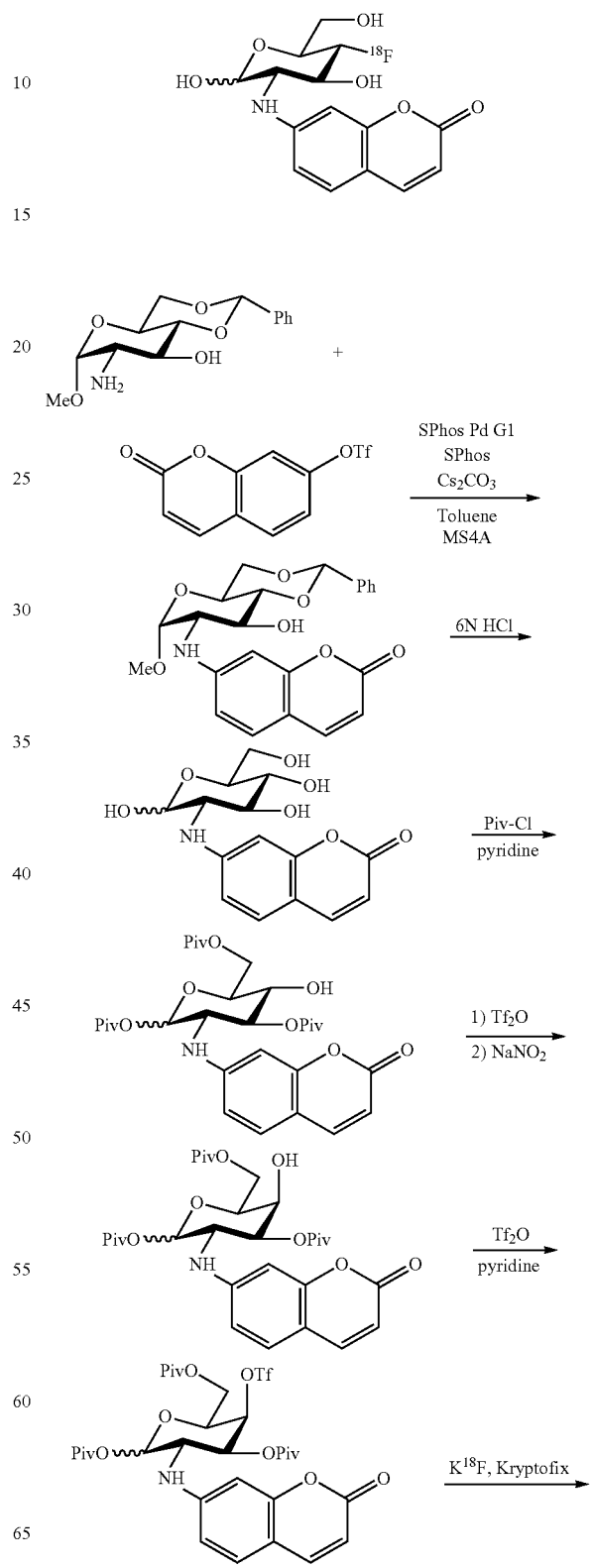
(ii) Method for Synthesizing a Compound Containing a Radioisotope $^{18}$F at 4-Position of Glucose
For example, the following compound (4-$^{18}$F-CLG) can be synthesized, for example, by steps given below.

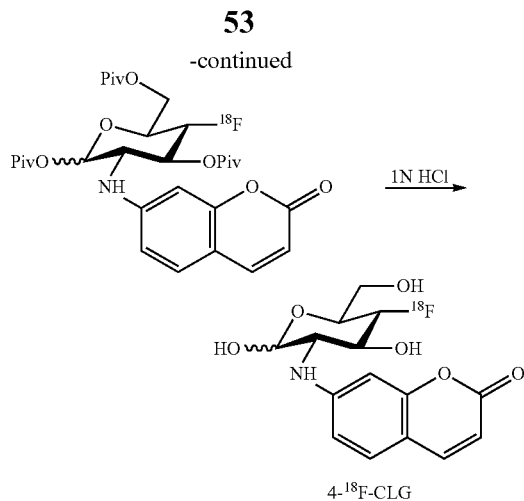

4-$^{18}$F-CLG

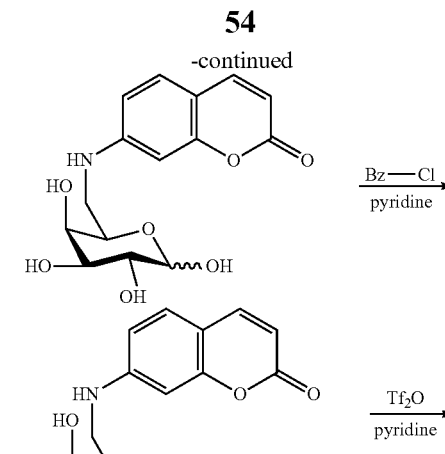

(iii) Method for Synthesizing a Compound Containing a Radioisotope $^{18}$F at 4-Position of Glucose For example, the following compound (4-[18]F-6-CDG) can be synthesized, for example, by steps given below.

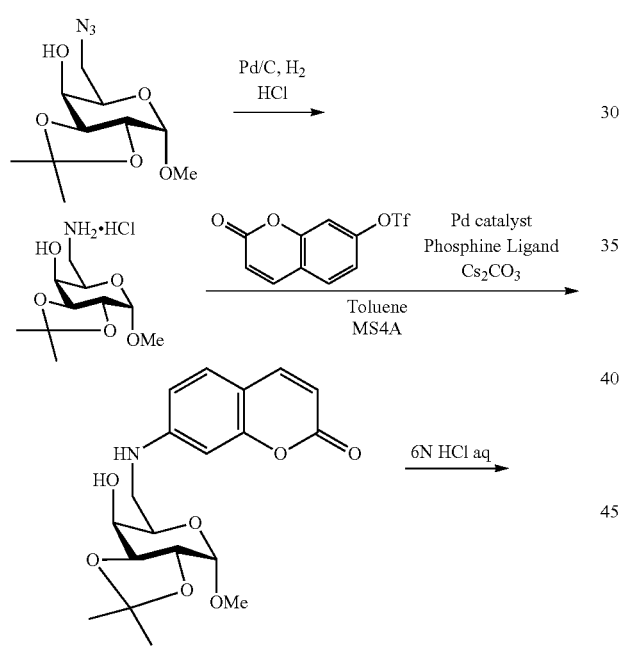

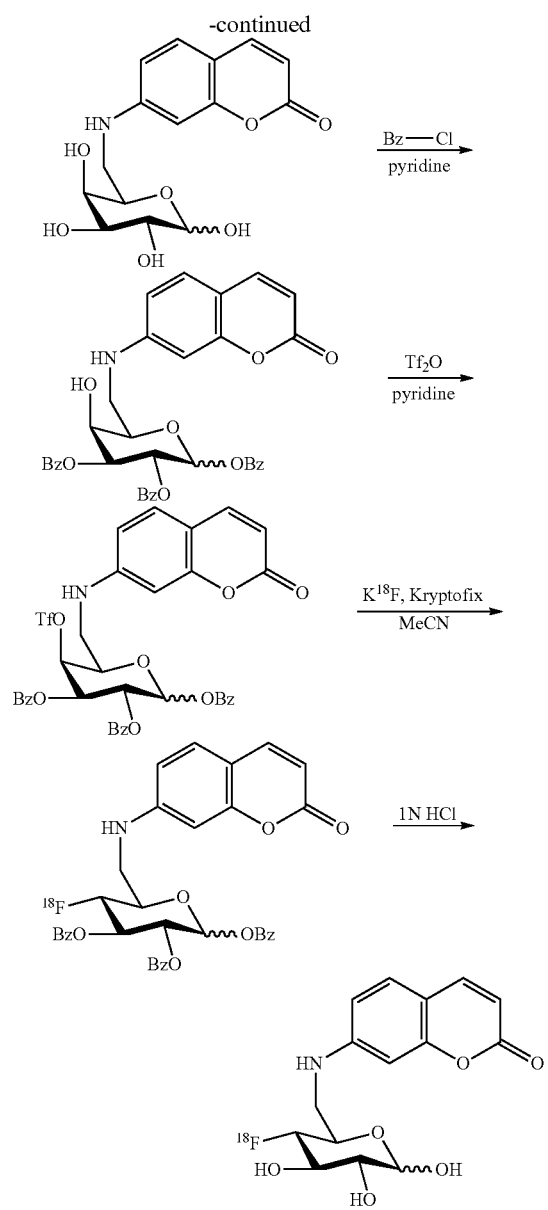

(iv) Method for Synthesizing a Compound Containing a Radioisotope $^{18}$F at 2-Position of Glucose For example, the following compound (2-[18]F-6-CDG) can be synthesized, for example, by steps given below.

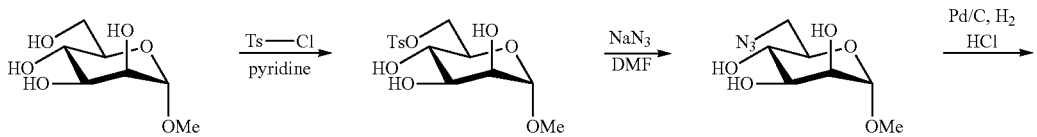

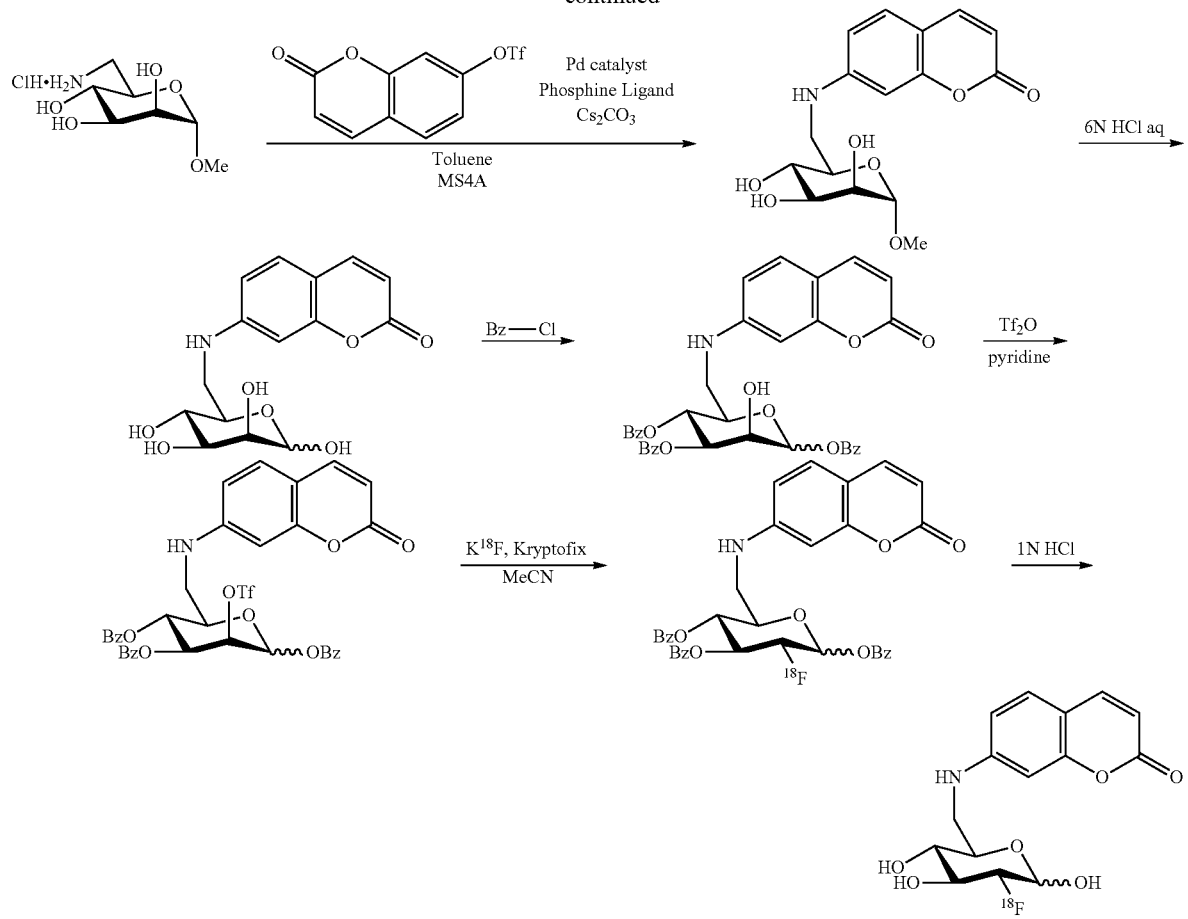

(v) Method for Synthesizing a Derivative Containing a Radioisotope $^{18}$F in a Coumarin Backbone—(1)

For example, the following compound ($^{18}$F-3-[$^{18}$F]TFM-CDG) can be synthesized, for example, by steps given below.

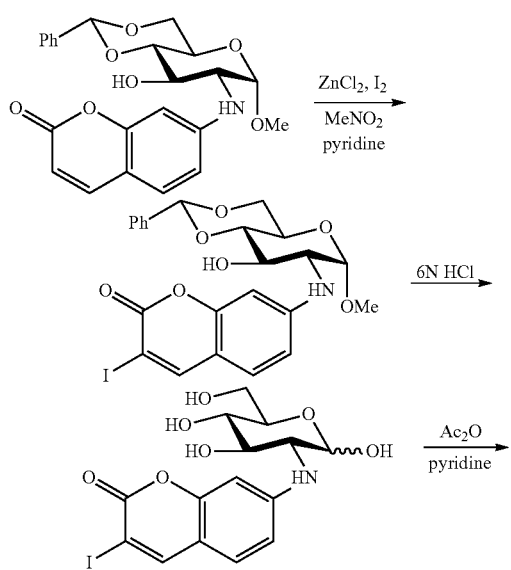

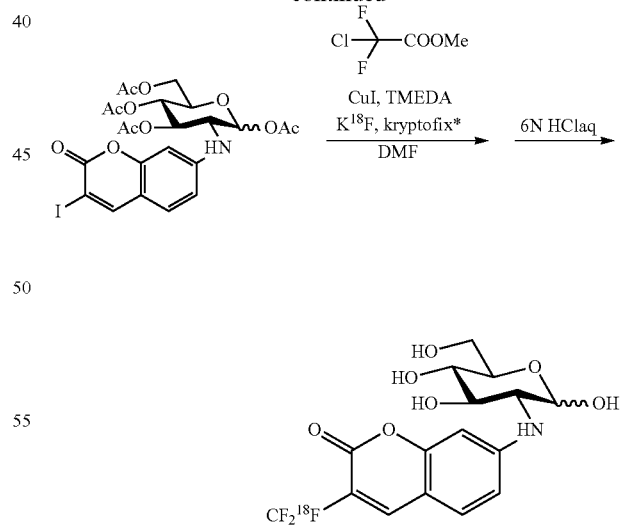

A derivative containing a radioisotope $^{18}$F in a quinoline backbone can be synthesized in the same way as above.

(vi) Method for Synthesizing a Derivative Containing a Radioisotope $^{18}$F in a Coumarin Backbone—(2)

For example, the following compound ($^{18}$F-4-[$^{18}$F]TFM-CDG) can be synthesized, for example, by steps given below.

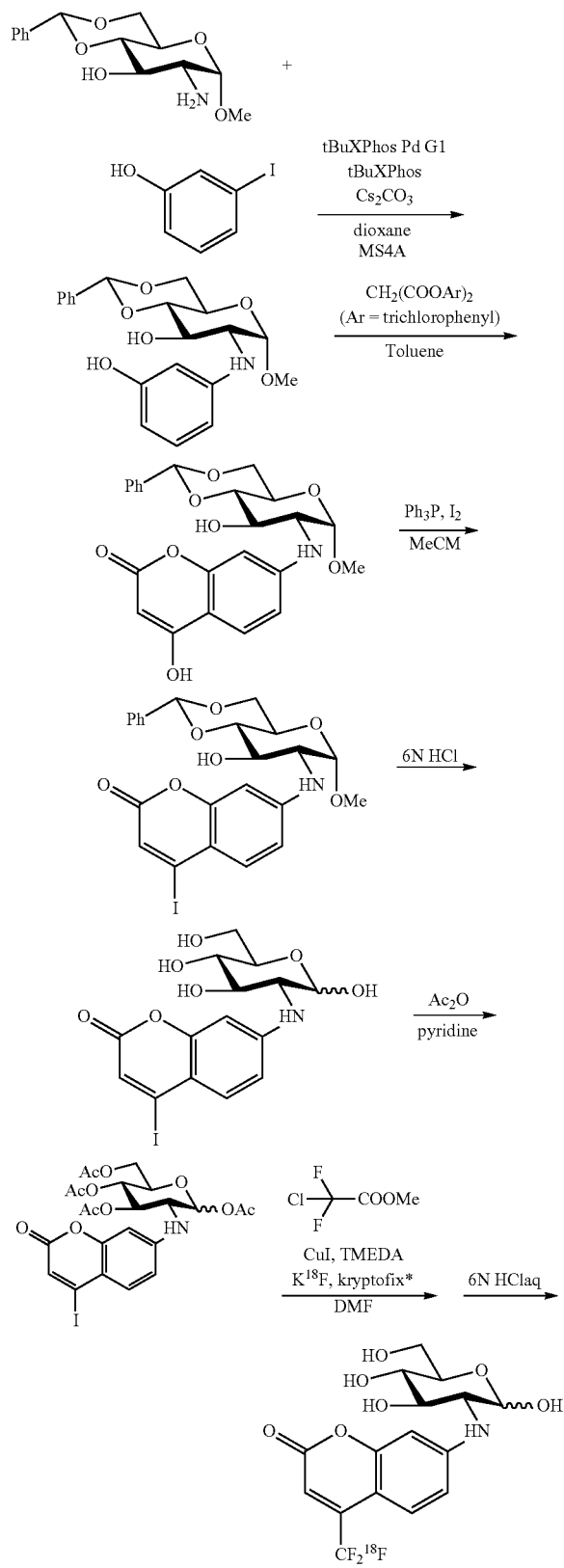

A derivative containing a radioisotope $^{18}$F in a quinoline backbone can be synthesized in the same way as above.

(vii) Method (1) for Synthesizing a Derivative Containing a Radioisotope $^{11}$C in a Coumarin Backbone For example, the following compound ($^{11}$C-3-[$^{11}$C] MCDG) can be synthesized, for example, by steps given below.

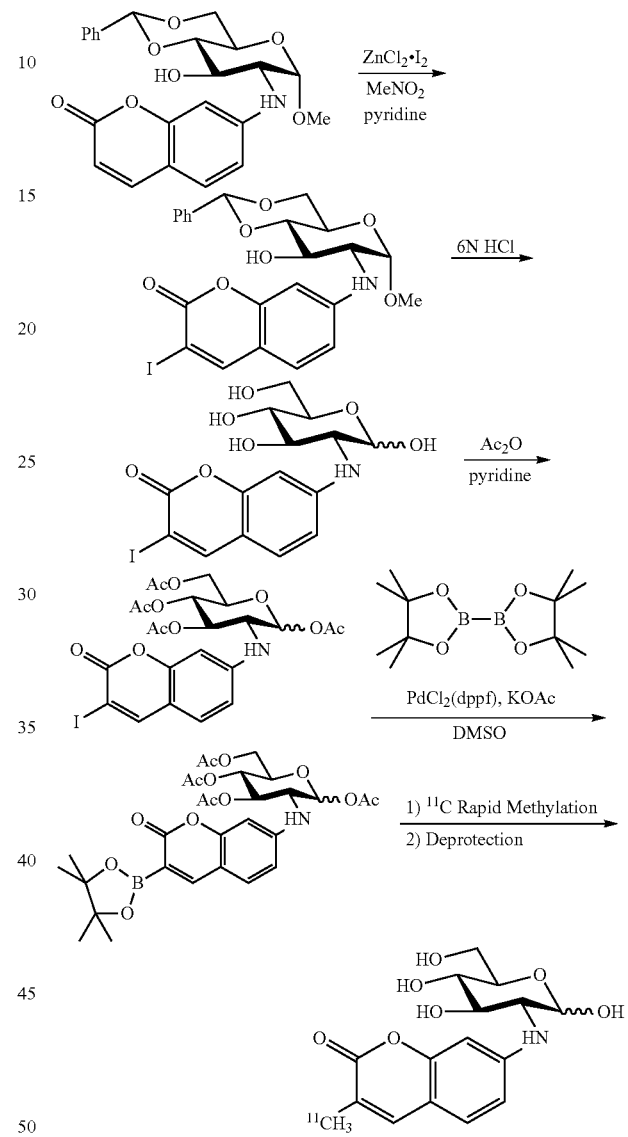

A derivative containing a radioisotope $^{11}$C in a quinoline backbone can be synthesized in the same way as above.

(viii) Method (2) for Synthesizing a Derivative Containing a Radioisotope $^{11}$C in a Coumarin Backbone For example, the following compound ($^{11}$C-4-[$^{11}$C] MCDG) can be synthesized, for example, by steps given below.

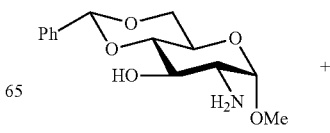

-continued

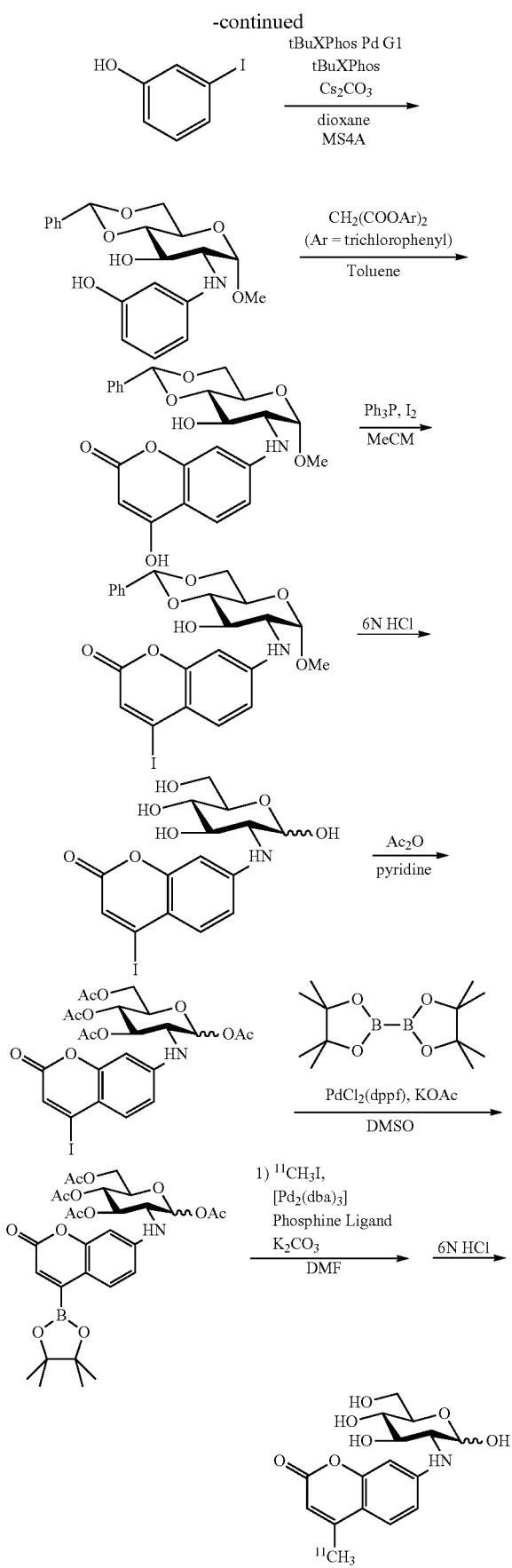

A derivative containing a radioisotope $^{11}C$ in a quinoline backbone can be synthesized in the same way as above.

The fluorophore contained in the glucose derivative of the present invention is a fluorophore having a coumarin backbone or quinoline backbone, that is, a fluorophore that emits blue fluorescence. Therefore, this fluorophore generally has a smaller molecular size than a molecule having a fluorescence maximum in the green, red, or near-infrared region and as such, is considered to have a fluorescent group smaller in steric hindrance against the passage through a membrane sugar transport system such as GLUT. In addition, the glucose derivative of the present invention is featured in that the coumarin backbone or quinoline backbone constituting the fluorophore is directly bound to the glucose backbone via NH. This is considered to provide an advantage that steric hindrance against the passage through a membrane sugar transport system such as GLUT is reduced.

As a result of conducting pharmacological tests applied to cells, the present inventors have confirmed that the aforementioned blue fluorescent D-glucose derivatives designated as CDG and QDG are taken into cancer cells via GLUT. The present inventors have further developed blue fluorescent L-glucose derivative molecules CLG and QLG, which are enantiomers of CDG and QDG, as control compounds. These four compounds, CDG, CLG, QDG, and QLG, are the first group of blue glucose derivatives that have been quantitatively shown to have a stereoselectivity between D/L-glucose for cellular uptake so as to allow the D form to be taken into cells via GLUT.

The D-glucose derivative (e.g., CDG or QDG) serving as the glucose derivative of the present invention can emit blue fluorescence as its control compound L-glucose derivative (e.g., CLG or QLG) does. Therefore, the glucose derivative of the present invention is useful equivalently to or more than the green D-glucose derivative 2-NBDG and the green L-glucose derivative 2-NBDLG previously reported by the present inventors (Patent Literature 2) for elucidating the glucose uptake mechanism of cells, and can also be used in combination therewith.

Specifically, for example, CDG or QDG can be used in combination with 2-NBDLG, or CLG or QLG can be used in combination with 2-NBDG, for the elucidation of the stereoselective transport mechanism of glucose in such a way that the occurrence of GLUT-mediated D-glucose-like cellular uptake and GLUT-free cellular uptake can be compared at the same time in the same cell selected from various cells, while such combined use can also offer valuable information for understanding the influence of the fluorescent group on the transport mechanism, though how to use the glucose derivative of the present invention is not limited thereto.

Further, when the blue D-glucose derivative CDG or QDG and the blue L-glucose derivative CLG or QLG of the present invention are examined for uptake into cancer cells, D form-dominant uptake was shown, which is similar to the relationship between the green D-glucose derivative 2-NBDG and the green L-glucose derivative 2-NBDLG. Furthermore, the blue L-glucose derivative CLG of the present invention was not taken into normal cells. Specifically, cancer cells can also be detected using the blue L-glucose derivative of the present invention, for example, CLG or QLG, like the detection of cancer cells using 2-NBDLG previously reported by the present inventors (Patent Literature 4).

One aspect of the present invention is a method for imaging a cell or an intracellular molecule using the glucose derivative of the present invention.

Another aspect of the present invention is an imaging agent for imaging a cell or an intracellular molecule, comprising the glucose derivative of the present invention.

The glucose derivative of the present invention is taken into cells via the membrane sugar transport system of the cells and therefore, can not only image the cells but can image intracellular molecules and organs, for example, cytoplasm and nucleus.

Yet another aspect of the present invention is an imaging agent for detecting a cancer cell using the glucose derivative of the present invention, preferably the L-glucose derivative, particularly preferably CLG or QLG.

An alternative aspect of the present invention is a method for detecting a cancer cell using a composition comprising the glucose derivative of the present invention, preferably the L-glucose derivative, particularly preferably CLG or QLG.

A further alternative aspect of the present invention is a PET imaging agent for detecting a cancer cell using a radiolabeled glucose derivative, which is one form of the glucose derivative of the present invention, preferably a radiolabeled L-glucose derivative, particularly preferably radiolabeled 4-F-CLG, 6-F-CLG, TFMCLG, or TFMQLG.

According to the present invention, a target cell can be imaged at an individual cell level by contacting a composition comprising the glucose derivative of the present invention (hereinafter, also referred to as the "composition of the present invention" or the "imaging agent of the present invention") as a reagent with the target cell. According to the present invention, a cell in a tissue can also be imaged at an individual cell level by contacting the composition of the present invention with the tissue containing the target cell for imaging.

The glucose derivative of the present invention includes both D-glucose derivatives and L-glucose derivatives. By using the D and L forms, the target can be imaged at a cell level depending upon the DL configuration of glucose, thereby making it possible to not only elucidate the functions of the target but discriminate between normal cells and abnormal cells.

As for microbes having properties different from mammalian cells in terms of the recognition, transport, and metabolism of glucose associated with the configurations of D and L forms, their functions can also be elucidated by imaging at a cell level using the D- or L-glucose derivative of the present invention.

According to the present invention, whether or not a target cell is a cancer cell can be further determined by contacting a composition comprising the glucose derivative of the present invention, preferably the L-glucose derivative (hereinafter, also referred to as the "composition of the present invention" or the "imaging agent of the present invention") as a reagent with the target cell.

According to the present invention, a cancer cell in a tissue can be detected by contacting the composition of the present invention with the tissue containing the target cell for imaging.

According to the present invention, cancer cells or a tissue containing these cells can be detected by administering the composition of the present invention to a living body for imaging. This method is useful as a method for detecting a cancer.

Cancer imaging can be achieved by PET using a composition comprising the radiolabeled glucose derivative of the present invention, preferably the radiolabeled L-glucose derivative of the present invention. Examples of the radiolabeled glucose derivative of the present invention can include 4-F-CLG, 6-F-CLG, 4-F-QLG, 6-F-QLG, TFMCDG, TMFCLG, TMFQDG, and TMFQLG and can preferably include 4-F-CLG, 4-F-QLG, TMFCLG, and TMFQLG.

The composition of the present invention includes compositions, comprising the glucose derivative of the present invention, in any form applicable to cells, and may be in any form of a solution, a gel and others without particular limitations as long as the composition is applicable to cells. The composition can contain any component without particular limitations as long as the component is suitable for application to cells. For example, the glucose derivative of the present invention may be dissolved in a buffer solution or a medium for cell culture for application to cells.

(II) Imaging of a Cell or Intracellular Molecule Using a Glucose Derivative

The target cell to be imaged using the glucose derivative of the present invention is not particularly limited, but can be mammal-derived cells, cells of a microbe such as *E. coli* or yeast, plant cells, fertilized eggs, or the like. These cells may be in any form including cells isolated from a living body, cells present in a tissue isolated from a living body, cells present in a tissue of a living body, primary cultured cells after isolation from a living body, and established cell lines. The cell to be imaged may be a normal cell or may be an abnormal cell (e.g., a cancer cell).

In the imaging method for a cell according to the present invention, the detection of the glucose derivative of the present invention taken into the cell can be performed by a commonly-used method for detecting fluorescence. For example, this method can be performed as follows: the detection of the glucose derivative present within the cell in the method of the present invention can be performed by measuring the fluorescence of the target cell in advance, subsequently contacting the glucose derivative with the target cell for a given time, washing out the resultant after the given time, measuring again the fluorescence of the target cell, and evaluating an increase in fluorescence intensity relative to the fluorescence intensity of the target cell before the contact. Alternatively, the cell may be imaged during the contact with the glucose derivative using an appropriate apparatus, such as a confocal microscope, which is capable of discriminating among the interior of the cell, the cell membrane, and the exterior of the cell. By recognizing the fluorescence intensity as an image, the cell intracellularly containing the glucose derivative of the present invention can be imaged, thereby making it possible to detect the cell. The evaluation may be conducted by means of total fluorescence intensity or fluorescence intensity distribution exhibited by a large number of cells using a fluorescence plate reader, flow cytometry, or the like.

Use of the glucose derivative of the present invention permits cell detection and/or imaging based on fluorescence (e.g., blue color). The glucose derivative of the present invention can be used at the same time with a glucose derivative having a different fluorophore, for example, green fluorescence-emitting 2-[N-(7-nitrobenz-2-oxa-1,3-diazol-4-yl)amino]-2-deoxy-D-glucose (2-NBDG) or 2-[N-(7-nitrobenz-2-oxa-1,3-diazol-4-yl)amino]-2-deoxy-L-glucose (2-NBDLG), and/or red fluorescence-emitting 2-Texas Red-2-amino-2-deoxy-L-glucose (2-TRLG). 2-NBDG, 2-NBDLG, and 2-TRLG are described in WO2010/16587 (Patent Literature 2) (the disclosure of which is incorporated herein by reference). As a result, two-color or three-color evaluation can be achieved.

For example, 2-NBDLG has the property of being specifically taken into a cancer and can be used for the detection of the cancer. The D-glucose derivative of the present invention (e.g., CDG or QDG) can be used at the same time with 2-NBDLG or 2-TRLG. As a result, the status evaluation of cancer cells or whole tumor cell masses containing cancer cells can also be conducted.

Specifically, for the imaging of cancer cells, etc., the concurrent use of the green fluorescent L-glucose derivative 2-NBDLG, which is specifically taken into the cancer cells, with the cell membrane-impermeable red fluorescent 2-TRLG is effective for examining nonspecific uptake ascribable to membrane injury, inflammation, or the like (see WO2012/133688 (Patent Literature 4) filed by the present inventors). In addition, if there is a method capable of visualizing normal cells present in the neighborhood of a cancer, or non-cancer cells that are not yet malignant but in a premalignant state, more accurate and highly reliable information on the nature of the cancer is obtained. A candidate compound therefor is a D-glucose derivative that emits blue fluorescence and is taken into cells via GLUT, to which the D-glucose derivative of the present invention (e.g., CDG or QDG) belong.

(III) Detection or Imaging of a Cancer Cell Using an L-Glucose Derivative

One embodiment of the L-glucose derivative of the present invention is a compound in which a particular fluorescence-emitting molecule having a coumarin backbone or quinoline backbone is bound to L-glucose having the property of being not taken into normal cells.

The uptake of the blue D-glucose derivative CDG or QDG and the blue L-glucose derivative CLG or QLG of the present invention into cancer cells showed D form-dominant uptake similar to the relationship between the green D-glucose derivative 2-NBDG and the green L-glucose derivative 2-NBDLG. An experiment using the blue L-glucose derivative of the present invention, for example, CLG confirmed a specific uptake into cancer cells. Thus, the L-glucose derivative of the present invention can also be used for specific detection of cancer cells.

In the method of the present invention, types of cancer cells that can be detected are not particularly limited, but include, for example, cancer cells of cancer of the ophthalmologic field such as eyelids and lacrimal glands, cancer of ears such as external ears and middle ears, cancers of nose such as nasal cavities and paranasal cavities, lung cancer, oral cancer, larynx cancer, throat cancer, esophageal cancer, stomach cancer, cancer of digestive organs such as small intestine and large intestine, cancer of the gynecological field including breast cancer, uterine cancer, ovary cancer, and fallopian tube cancer, cancer of reproductive organs, kidney cancer, bladder cancer, prostate cancer, anus cancer, skin cancer, bone cancer, muscular cancer (sarcoma), blood cancer such as leukemia, malignant lymphoma, peripheral and central nervous cancers, and glial cancer.

In the method for detecting a cancer according to the present invention, the L-glucose derivative of the present invention (e.g., CLG or QLG) can be used at the same time with an additional fluorescently labeled glucose derivative, for example, 2-NBDG, 2-NBDLG, or 2-TRLG, or a combination thereof. As a result, the status evaluation of cancer cells or whole tumor cell masses containing cancer cells can also be conducted.

The method for detecting a cancer according to the present invention and the imaging agent therefor can be used for determination of the presence of tumor cells, the status evaluation thereof, or the discrimination thereof from normal cells with respect to tissues excised at the time of surgery, oral tumors, endoscopically obtained digestive organ tumors, gynecologic tumors such as uterine cervix cancer, or biopsy preparations obtained at the time of biopsy diagnosis, etc., of the lung or various organs. As a result, detailed cell evaluation at a cell level can be conducted rapidly with a convenient apparatus equipped with fluorescence. This is effective, for example, for determining a guideline for the selection of a treatment method, determining the therapeutic effects of drugs or the like, and determining the appropriate extent of surgery after exposure of an affected part.

In the detection method of the present invention, the detection of the L-glucose derivative present within the cancer cell can be performed, for example, by measuring the fluorescence of the target cell in advance, subsequently contacting the fluorescently labeled L-glucose derivative with the target cell for a given time, washing out the resultant after the given time, measuring again the fluorescence of the target cell, and evaluating an increase in fluorescence intensity relative to the fluorescence intensity of the target cell before the contact. By recognizing the fluorescence intensity as an image, the cell intracellularly containing the L-glucose derivative can be imaged, thereby making it possible to detect the cancer cell or the cell at a risk thereof. The evaluation may be conducted by means of total fluorescence intensity or fluorescence intensity distribution exhibited by a large number of cells using a fluorescence plate reader, flow cytometry, or the like.

The L-glucose derivative of the present invention, when administered to a vascular vessel such as the vein, permits systemic imaging. In addition, the L-glucose derivative, when locally administered to a tissue to be observed, permits cell imaging.

In addition, in the case of using the radiolabeled L-glucose derivative of the present invention, a cancer can also be detected by PET.

As is evident from the above description, the glucose derivative of the present invention is useful for detecting cancer cells and also useful as, for example, an active ingredient for an imaging agent for visualizing cancer cells. The L-glucose derivative may be dissolved in a solvent for dissolution thereof (injectable physiological saline, etc.) and provided in the form of a solution, or may be combined with a solvent for dissolution thereof and provided in the form of a kit for preparing a solution by dissolution when used. The concentration of the fluorescent L-glucose derivative in the solution may be adjusted in the range of, for example, 1 nM to 100 mM. The method for detecting a cancer cell using the L-glucose derivative of the present invention may be used in combination with a method known per se in the art to further improve determination accuracy.

EXAMPLES

Hereinafter, the present invention will be described in detail with reference to Examples. However, the present invention is not construed as being limited by the description below.

Synthesis of Glucose Derivative

Example 1: Synthesis of CDG

CDG was synthesized from D-glucosamine hydrochloride as follows:

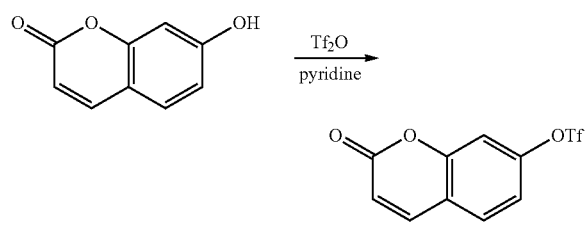

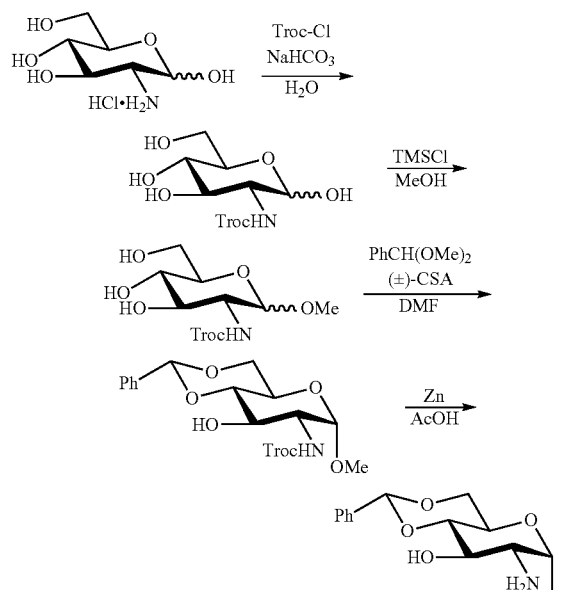

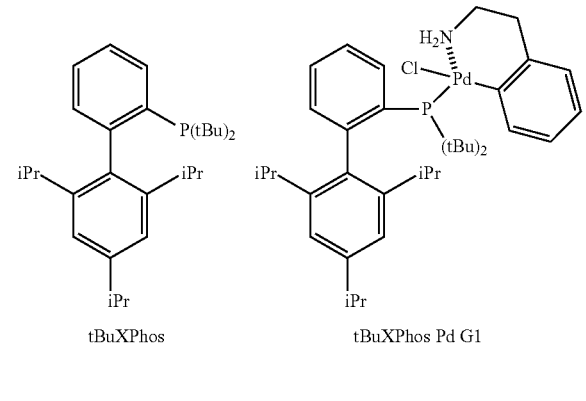

(1-1) Synthesis of 2-oxo-2H-chromen-7-yl trifluoromethanesulfonate Represented by Following Formula

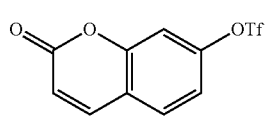 [SMILES: O=c1ccc2ccc(OS(=O)(=O)C(F)(F)F)cc2o1]

In an argon atmosphere, 4-methylumbelliferone (100 mg, 617 μmol) was dissolved in pyridine (6 mL), and the solution was cooled in ice. Trifluoromethanesulfonic anhydride (114 μL, 679 μmol) was added dropwise thereto. Then, the mixture was stirred at room temperature for 5 hours. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column ($SiO_2$, 20 g) to obtain the compound (160 mg, 88%) as a white solid.

(1-2) Synthesis of 2-deoxy-2-(2,2,2-trichloroethoxycarbonylamino)-D-glucose Represented by Following Formula

D-Glucosamine hydrochloride (10 g, 46.4 mmol) was dissolved in water (100 mL). To the solution, $NaHCO_3$ (10 g, 119 mmol) was added at room temperature. Then, 2,2,2-trichloroethyl chloroformate (7.7 mL, 55.7 mmol) was added dropwise thereto at 0° C. The mixture was stirred at 0° C. for 20 minutes, gradually heated to room temperature, and stirred overnight. The deposited crystals were collected by filtration and washed with water and ether. After overnight drying, the obtained white crystals were recrystallized from warm methanol, and the obtained crystals were collected by filtration to obtain the compound (6.0 g, 36%).

(1-3) Synthesis of methyl 4,6-O-benzylidene-2-deoxy-2-(2,2,2-trichloroethoxycarbonylamino)-α-D-glucopyranoside Represented by Following Formula

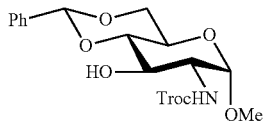

In an argon atmosphere, 2-deoxy-2-(2,2,2-trichloroethoxycarbonylamino)-D-glucose (6.0 g, 16.9 mmol) was suspended in methanol (200 mL). To the suspension, chlorotrimethylsilane (21 mL) was added dropwise at 0° C. After the dropwise addition, the mixture was heated to reflux and stirred for 2 hours. After the completion of the reaction, the reaction mixture was allowed to cool, and the solvent was distilled off under reduced pressure. Dimethylformamide (200 mL) was added to the residue, then benzylidene dimethyl acetal (4.2 mL) and (±)-camphorsulfonic acid (110 mg) were added, and the mixture was stirred overnight at room temperature. After the completion of the reaction, the reaction mixture was neutralized by the addition of a saturated aqueous solution of sodium bicarbonate. Acetonitrile was distilled off under reduced pressure until the solution volume became 0.5 L. Then, the residue was subjected to extraction with ethyl acetate, and the extract was washed with a saturated aqueous solution of sodium bicarbonate and then washed with saturated saline. The organic layer was dried over sodium sulfate, and the solvent was distilled off. The residue was purified using a silica gel column (SiO$_2$, 75 g) to obtain the compound (1.0 g, 12%) as white crystals.

(1-4) Synthesis of methyl 4,6-O-benzylidene-2-deoxy-2-amino-α-D-glucopyranoside Represented by Following Formula

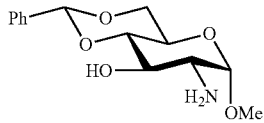

In an argon atmosphere, methyl 4,6-O-benzylidene-2-deoxy-2-(2,2,2-trichloroethoxycarbonylamino)-α-D-glucopyranoside (1.0 g, 2.19 mmol) was dissolved in acetic acid (20 mL). To the solution, zinc (1.0 g) was added, and the mixture was stirred for 3.5 hours. After the completion of the reaction, the reaction mixture was filtered, and the solvent was distilled off. The residue was freeze-dried from dioxane to obtain the compound (600 mg, 98%) as white crystals.

(1-5) Synthesis of methyl 4,6-O-benzylidene-2-deoxy-2-(2-oxo-2H-chromen-7-yl)amino-α-D-glucopyranoside Represented by Following Formula

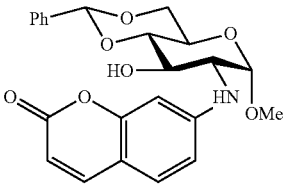

In an argon atmosphere, toluene (3.4 mL) was added to activated molecular sieve 4A (pellet), methyl 4,6-O-benzylidene-2-deoxy-2-amino-α-D-glucopyranoside (116.0 mg, 340 µmol), 2-oxo-2H-chromen-7-yl trifluoromethanesulfonate (100 mg, 340 µmol), tBuXPhos Pd G1 (chloro[2-(di-tert-butylphosphino)-2',4',6'-triisopropyl-1,1'-biphenyl][2-(2-aminoethyl)phenyl)]palladium(II)) (Sigma-Aldrich) (31.1 mg, 34 µmol), tBuXPhos (2-di-tert-butylphosphino-2',4',6'-triisopropylbiphenyl) (Sigma-Aldrich) (39.3 mg, 68 µmol), and Cs$_2$CO$_3$ (276.9 mg, 850 µmol), and the mixture was refluxed for 4 hours. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column (SiO$_2$, 5 g) to obtain the compound (51.2 mg, 35%) as a pale yellow solid.

(1-6) Synthesis of 2-deoxy-2-(2-oxo-2H-chromen-7-yl)amino-D-glucose (CDG) Represented by Following Formula

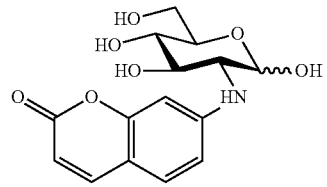

The compound methyl 4,6-O-benzylidene-2-deoxy-2-(2-oxo-2H-chromen-7-yl)amino-α-D-glucopyranoside (40 mg, 94 µmol) was dissolved in an 80% aqueous acetic acid solution (2 mL), and the solution was heated to 50° C. and stirred 2 hours. After the completion of the reaction, the solvent was distilled off. 6 N hydrochloric acid (1.8 mL) was added to the residue, and the mixture was heated to 80° C. and stirred for 4 hours. After the completion of the reaction, the solvent was distilled off. The residue was dissolved in dimethylformamide. The solution was purified by reverse-phase HPLC. A fraction containing the compound of interest was freeze-dried to obtain the compound as a pale yellow solid.

The yield was 9.6 mg, and the percent yield was 47%. Also, results of analyzing the obtained compound are as follows.

$^1$H NMR (D$_2$O, 400 MHz): δ 7.75 (dd, J=1.37 Hz, 9.61 Hz, 1H, Coumarin-4H), δ 7.30 (d, J=8.69 Hz, 0.7H, Coumarin-5Hα) δ 7.29 (d, J=8.69 Hz, 0.3H, Coumarin-5Hβ), δ 6.69-6.65 (m, 1H, Coumarin-6H), δ 6.59 (s, 1H, Coumarin- 8H), δ 6.01 (d, J=9.60 Hz, 0.7H, Coumarin-3Hα), δ 6.01 (d, J=9.61 Hz, 0.3H, Coumarin-3Hβ), δ 5.20 (d, J=3.55 Hz, 0.7H, H-1α), δ 3.78-3.21 (m, 6H, H-2, H-3, H-4, H-5, H-6, H-6'); ESI-MS: $C_{15}H_{18}NO_7$ [M+H]$^+$ calc.: 324.1, found: 324.0. maximum excitation wavelength (Ex max) 366.5 nm, maximum fluorescence wavelength (Em max) 454.5 nm.

Example 2: Synthesis of CLG

CLG was synthesized in the same way as in CDG using L-glucosamine hydrochloride instead of D-glucosamine hydrochloride. The yield was 13.2 mg, and the percent yield was 32%. Also, results of analyzing the obtained compound are as follows.

$^1$H NMR (D$_2$O, 400 MHz): δ 7.75 (dd, J=1.83 Hz, 9.15 Hz, 1H, Coumarin-4H), δ 7.31 (d, J=8.69 Hz, 0.6H, Coumarin-5Hα) δ 7.30 (d, J=8.69 Hz, 0.4H, Coumarin-5Hβ), β 6.69-6.65 (m, 1H, Coumarin-6H), δ 6.60 (s, 1H, Coumarin-8H), δ 6.02 (d, J=9.61 Hz, 0.6H, Coumarin-3Hα), δ 6.01 (d, J=9.15 Hz, 0.4H, Coumarin-3Hβ), δ 5.21 (d, J=3.20 Hz, 0.7H, H-1α), δ 3.82-3.22 (m, 6H, H-2, H-3, H-4, H-5, H-6, H-6'); ESI-MS: $C_{15}H_{18}NO_7$ [M+H]$^+$ calc.: 324.1, found: 324.1.

Example 3: Synthesis of QDG

QDG was synthesized from D-glucosamine hydrochloride as follows:

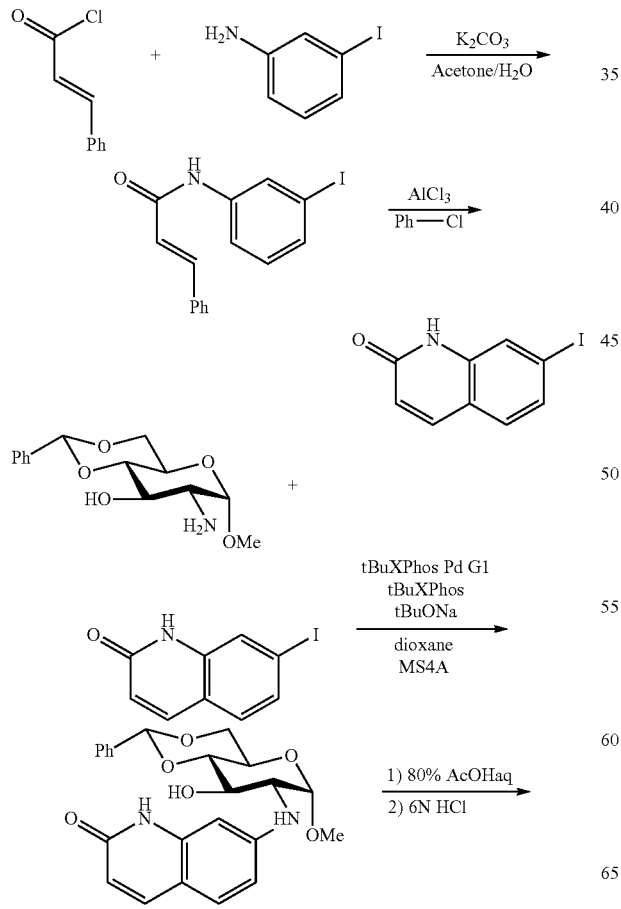

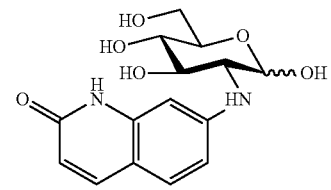

(3-1) Synthesis of N-(3-iodophenyl)cinnamamide Represented by Following Formula

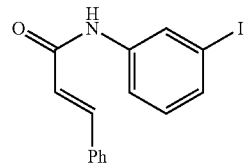 [SMILES: O=C(/C=C/c1ccccc1)Nc1cccc(I)c1]

m-Iodoaniline (10 g, 45.7 mmol) and potassium carbonate (9.47 g, 68.6 mmol) were suspended in acetone/water (1/2, 94 mL). To the suspension, cinnamic chloride (9.3 g, 56.2 mmol) was added dropwise, and the mixture was stirred for 30 minutes. The reaction was terminated by pouring to ice water. The deposited white solid was collected by filtration and washed with water and diethyl ether. The solid was dried overnight using a pump to obtain the compound (17.6 g, quant) as white crystals.

(3-2) Synthesis of 7-iodoquinolin-2(1H)-one Represented by Following Formula

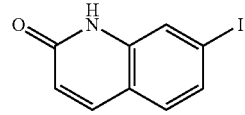 [SMILES: O=c1ccc2ccc(I)cc2[nH]1]

In an argon atmosphere, the compound N-(3-iodophenyl)cinnamamide (1.0 g, 2.86 mmol) was dissolved in chlorobenzene (28.6 mL), and the solution was cooled in ice. Aluminum chloride (1.91 g, 14.3 mmol) was added thereto, and the mixture was heated to 100° C. and stirred for 2 hours. The reaction was terminated by pouring to ice water. The reaction mixture was separated and washed with ethyl acetate (300 mL) and saturated saline (200 mL×3). The organic layer was dried over anhydrous sodium sulfate, and the solvent was distilled off. The residue was purified using a silica gel column (SiO$_2$, 30 g) to obtain the compound (300 mg, 39%) as a pink solid.

(3-3) Synthesis of methyl 4,6-O-benzylidene-2-deoxy-2-(2-oxo-1,2-dihydroquinoline-7-yl)amino-α-D-glucopyranoside Represented by Following Formula

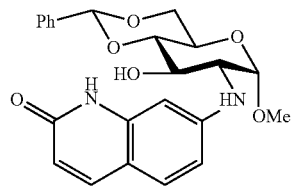

In an argon atmosphere, dioxane (1.05 mL) was added to activated molecular sieve 4A (pellet), methyl 4,6-O-benzylidene-2-deoxy-2-(2-oxo-2H-chromen-7-yl)amino-α-D-glucopyranoside (30.3 mg, 76.7 μmol), 7-iodoquinolin-2(1H)-one (4.6 mg, 51.2 μmol), tBuXPhos Pd G1 (chloro[2-(di-tert-butylphosphino)-2',4',6'-triisopropyl-1,1'-biphenyl][2-(2-aminoethyl)phenyl)]palladium(II)) (3.6 mg, 5.12 μmol) (Sigma-Aldrich), tBuXPhos (2-di-tert-butylphosphino-2',4',6'-triisopropylbiphenyl) (4.2 mg, 10.23 μmol) (Sigma-Aldrich), and tBuONa (49.2 mg, 512 μmol), and the mixture was refluxed for 1 hour. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column ($SiO_2$, 5 g) to obtain the compound (18.3 mg, 84%) as a pale yellow solid.

(3-4) Synthesis of 2-deoxy-2-(2-oxo-1,2-dihydroquinolin-7-yl)amino-D-glucose (QDG) Represented by Following Formula

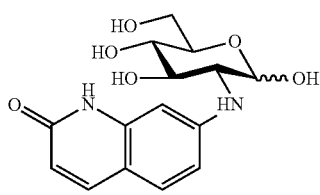

The compound methyl 4,6-O-benzylidene-2-deoxy-2-(2-oxo-1,2-dihydroquinolin-7-yl)amino-α-D-glucopyranoside (46 mg, 108 μmol) was dissolved in an 80% aqueous acetic acid solution (2 mL), and the solution was heated to 50° C. and stirred for 2 hours. After the completion of the reaction, the solvent was distilled off. 6 N hydrochloric acid (1.8 mL) was added to the residue, and the mixture was heated to 80° C. and stirred for 4 hours. After the completion of the reaction, the solvent was distilled off. The residue was dissolved in water. The solution was purified by reverse-phase HPLC. A fraction containing the compound of interest was freeze-dried to obtain the compound (18.9 mg, 53%) as a pale yellow solid. The yield was 18.9 mg, and the percent yield was 53%. Also, results of analyzing the obtained compound are as follows.

$^1$H NMR ($D_2O$, 400 MHz): δ 7.78 (d, J=9.15 Hz, 0.6H, Quinolinone-4Hα), δ 7.77 (d, J=9.61 Hz, 0.4H, Quinolinone-4Hβ), δ 7.38 (t, J=8.69 Hz, 1H, Quinolinone-5H), δ 6.72-6.67 (td, J=2.29 Hz, J=10.1 Hz, 1H, Quinolinone-6H), δ 6.51 (d, J=2.29 Hz, 0.4H, Quinolinone-8Hβ), δ 6.49 (d, J=1.83 Hz, 0.6H, Quinolinone-8Hα), δ 6.24 (d, J=9.15 Hz, 0.6H, Quinolinone-3Hα), δ 6.22 (d, J=9.15 Hz, 0.4H, Quinolinone-3Hβ), δ 5.21 (d, J=3.20 Hz, 0.6H, H-1α), δ 3.82-3.29 (m, 6H, H-2, H-3, H-4, H-5, H-6, H-6'); ESI-MS: $C_{15}H_{18}N_2O_6$ $[M+H]^+$ calc.: 323.1, found: 323.1. maximum excitation wavelength (Ex max) 353.5 nm, maximum fluorescence wavelength (Em max) 423.0 nm.

Example 4: Synthesis of QLG

QLG was synthesized in the same way as in QDG using L-glucosamine hydrochloride instead of D-glucosamine hydrochloride. The yield was 23.2 mg, and the percent yield was 33%. Also, results of analyzing the obtained compound are as follows.

$^1$H NMR ($D_2O$, 400 MHz): δ 7.77 (d, J=9.15 Hz, 0.5H, Quinolinone-4Hα), δ 7.76 (d, J=9.61 Hz, 0.5H, Quinolinone-4Hβ), δ 7.40-7.35 (m, 1H, Quinolinone-5H), δ 6.71-6.67 (td, J=2.29 Hz, J=7.78 Hz, 1H, Quinolinone-6H), δ 6.51-6.48 (m, 1H, Quinolinone-8H), δ 6.25-6.20 (m, 1H, Quinolinone-3H), δ 5.22 (d, J=3.66 Hz, 0.5H, H-1α), δ 3.83-3.29 (m, 6H, H-2, H-3, H-4, H-5, H-6, H-6'); ESI-MS: $C_{15}H_{18}N_2O_6$ $[M+H]^+$ calc.: 323.1, found: 323.1.

Example 5: Synthesis of 4-MCDG

4-MCDG was synthesized as follows:

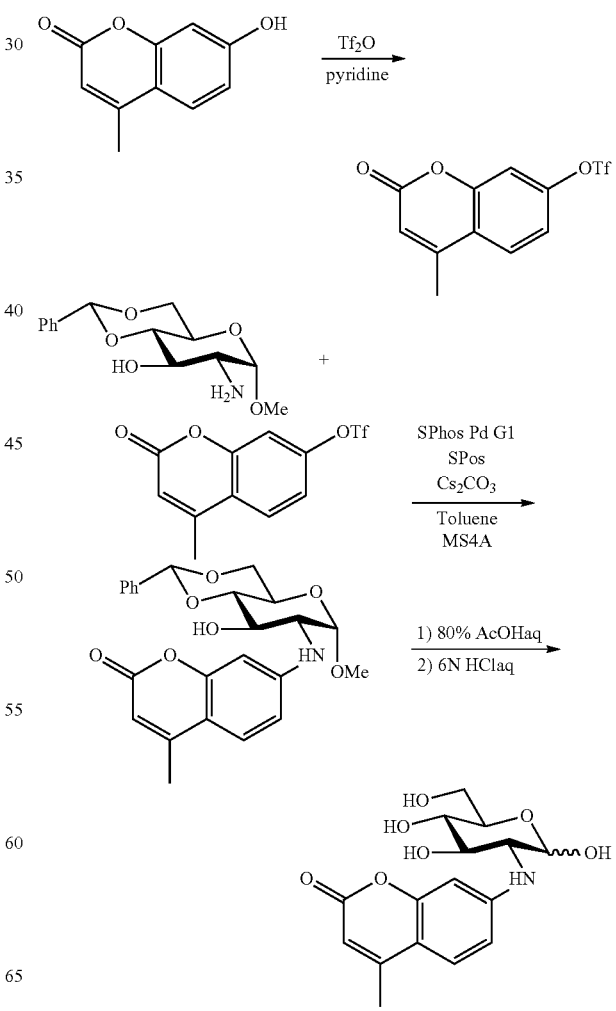

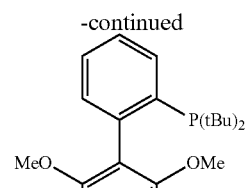

SPhos

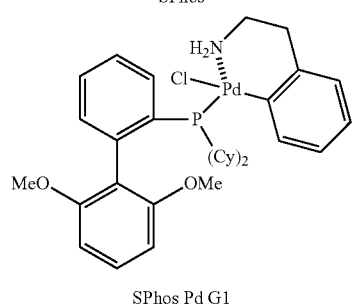

SPhos Pd G1

(5-1) Synthesis of 2-oxo-4-methyl-2H-chromen-7-yl trifluoromethanesulfonate Represented by Following Formula

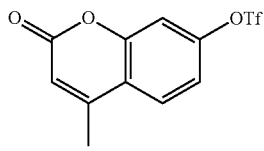 [SMILES: Cc1cc(=O)oc2cc(OS(=O)(=O)C(F)(F)F)ccc12]

In an argon atmosphere, 4-methylumbelliferone (1 g, 5.68 mmol) was dissolved in pyridine (30 mL), and the solution was cooled in ice. Trifluoromethanesulfonic anhydride (1.0 μL, 6.24 mmol) was added dropwise thereto. Then, the mixture was stirred at room temperature for 1 hour. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column ($SiO_2$, 30 g) to obtain the compound (1.7 g, 97%) as a white solid.

(5-2) Synthesis of methyl 4,6-O-benzylidene-2-deoxy-2-(2-oxo-4-Methyl-2H-chromen-7-yl)amino-α-D-glucopyranoside Represented by Following Formula

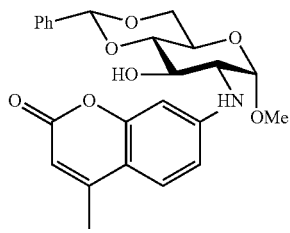

In an argon atmosphere, toluene (6.5 mL) was added to activated molecular sieve 4A (pellet), methyl 4,6-O-benzylidene-2-deoxy-2-amino-α-D-glucopyranoside (166 mg, 0.487 mmol), 2-oxo-4-methyl-2H-chromen-7-yl trifluoromethanesulfonate (100 mg, 0.324 mmol), SPhos Pd G1 (chloro(2-dicyclohexylphosphino-2',6'-dimethoxy-1,1'-biphenyl)[2-(2-aminoethylphenyl)]palladium(II)) (73.9 mg, 97.2 μmol) (Sigma-Aldrich), SPhos (2-dicyclohexylphosphino-2',6'-dimethoxybiphenyl) (39.9 mg, 97.2 μmol) (Sigma-Aldrich), and $Cs_2CO_3$ (264 mg, 810 μmol), and the mixture was refluxed for 6 hours. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column ($SiO_2$, 40 g) to obtain the compound (47 mg, 33%) as a pale yellow solid.

(5-3) Synthesis of 2-deoxy-2-(2-oxo-4-methyl-2H-chromen-7-yl)amino-D-glucose (MCDG) Represented by Following Formula

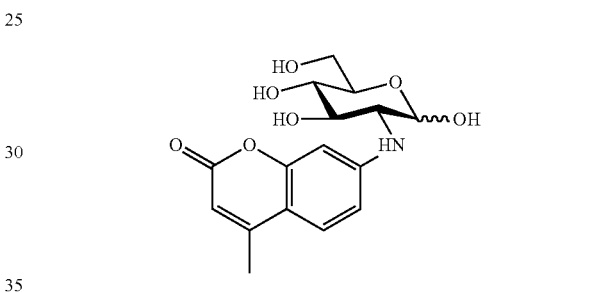

The compound methyl 4,6-O-benzylidene-2-deoxy-2-(2-oxo-4-methyl-2H-chromen-7-yl)amino-α-D-glucopyranoside (65 mg, 148 μmol) was dissolved in an 80% aqueous acetic acid solution (2 mL), and the solution was heated to 50° C. and stirred for 2 hours. After the completion of the reaction, the solvent was distilled off. 6 N hydrochloric acid (2 mL) was added to the residue, and the mixture was heated to 80° C. and stirred for 12 hours. After the completion of the reaction, the solvent was distilled off. The residue was dissolved in water. The solution was purified by reverse-phase HPLC. A fraction containing the compound of interest was freeze-dried to obtain the compound as a pale yellow solid. The yield was 26 mg, and the percent yield was 52%. Also, results of analyzing the obtained compound are as follows.

$^1$H NMR (CD$_3$OD, 400 MHz): δ 7.46 (d, J=8.69 Hz, 0.7H, Coumarin-5Hα), δ 7.46 (d, J=9.61 Hz, 0.3H, Coumarin-5Hβ), δ 6.77-6.74 (m, 1H, Coumarin-6H), δ 6.66 (d, J=2.29 Hz, 0.3H, Coumarin-8Hβ), δ 6.61 (d, J=2.29 Hz, 0.7H, Coumarin-8Hα), δ 5.92 (d, J=1.37 Hz, 0.7H, Coumarin-3Hα), δ 5.91 (d, J=0.92 Hz, 0.3H, Coumarin-3Hβ), δ 5.18 (d, J=3.20 Hz, 0.7H, H-1α), δ 4.56 (d, J=7.78 Hz, 0.3H, H-1β), δ 3.90-3.33 (m, 6H, H-2, H-3, H-4, H-5, H-6, H-6') δ 2.37 (s, 3H, Me); ESI-MS: $C_{16}H_{19}NO_7$ [M+H]$^+$ calc.: 338.1, found: 338.1. maximum excitation wavelength (Ex max) 362.0 nm, maximum fluorescence wavelength (Em max) 446.0 nm.

4-MCLG can be synthesized in the same way as in 4-MCDG using L-glucosamine.

Example 6: Synthesis of 3-MCDG

3-MCDG was synthesized as follows:

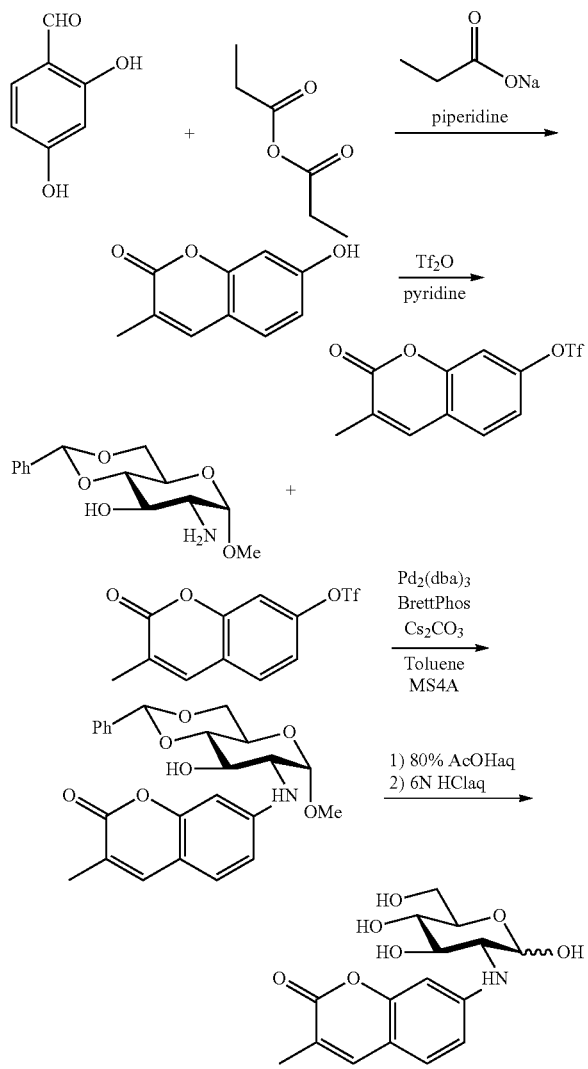

(6-1) Synthesis of 2-oxo-3-methyl-2H-chromen-7-yl trifluoromethanesulfonate Represented by Following Formula

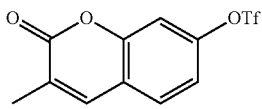 [SMILES: Cc1cc2ccc(OS(=O)(=O)C(F)(F)F)cc2oc1=O]

2,4-Dihydrobenzaldehyde (1 g, 7.24 mmol), propionic anhydride (2.5 mL, 19.2 mmol), sodium propionate (1.5 g, 15.6 mmol), and piperidine (0.7 mL, 9.54 mmol) were added to a reaction vessel and reacted at 160° C. for 1.5 hours. Purified oil was dissolved in methanol, and water was added to the solution. The deposited solid was collected by filtration. The compound of interest was recovered from the filtrate. The compound was purified using a silica gel column (SiO$_2$, 55 g). In an argon atmosphere, the obtained crude product (110 mg, 624 μmol) was dissolved in pyridine (6.24 mL), and the solution was cooled in ice. Trifluoromethanesulfonic anhydride (115 μL, 687 μmol) was added dropwise thereto. Then, the mixture was stirred at room temperature for 1 hour. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column (SiO$_2$, 20 g) to obtain the compound (120 mg, 62%) as a white solid.

(6-1) Synthesis of methyl 4,6-O-benzylidene-2-deoxy-2-(2-oxo-3-methyl-2H-chromen-7-yl)amino-α-D-glucopyranoside Represented by Following Formula

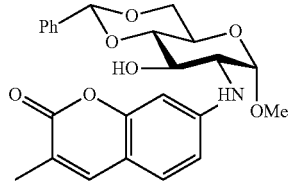

In an argon atmosphere, toluene (0.81 mL) was added to activated molecular sieve 4A (pellet), methyl 4,6-O-benzylidene-2-deoxy-2-amino-α-D-glucopyranoside (33.2 mg, 97.3 μmol), 2-oxo-3-methyl-2H-chromen-7-yl trifluoromethanesulfonate (25 mg, 81.1 μmol), Pd$_2$(dba)$_3$ (tris (dibenzylideneacetone)dipalladium(0)) (7.4 mg, 8.11 μmol), BrettPhos (2-(dicyclohexylphosphino)-3,6-dimethoxy-2',4', 6'-triisopropyl-1,1'-biphenyl) (Sigma-Aldrich) (8.7 mg, 16.2 μmol), and Cs$_2$CO$_3$ (26.4 mg, 81.1 μmol), and the mixture was refluxed for 1 hour. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column (SiO$_2$, 16 g) to obtain the compound (31.2 mg, 88%) as a pale yellow solid.

(6-3) Synthesis of 2-deoxy-2-(2-oxo-3-methyl-2H-chromen-7-yl)amino-D-glucose (3-MCDG) Represented by Following Formula

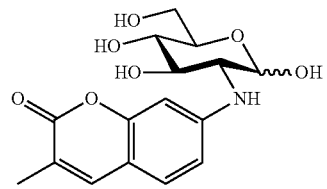

The compound methyl 4,6-O-benzylidene-2-deoxy-2-(2-oxo-3-methyl-2H-chromen-7-yl)amino-α-D-glucopyranoside (139 mg, 31.6 μmol) was dissolved in an 80% aqueous acetic acid solution (3 mL), and the solution was heated to 50° C. and stirred for 4 hours. After the completion of the reaction, the solvent was distilled off. 6 N hydrochloric acid (3 mL) was added to the residue, and the mixture was heated to 80° C. and stirred for 21 hours. After the completion of the reaction, the solvent was distilled off. The residue was dissolved in dimethylformamide. The solution was purified by reverse-phase HPLC. A fraction containing the compound of interest was freeze-dried to obtain the compound as a pale yellow solid.

The yield was 33.2 mg, and the percent yield was 31%. Also, results of analyzing the obtained compound are as follows. $^1$H NMR (CD$_3$OD, 400 MHz): δ 7.55 (s, 1H, Coumarin-4H), δ 7.23 (d, J=8.23 Hz, 0.7H, Coumarin-5Hα), δ 7.20 (d, J=8.70 Hz, 0.3H, Coumarin-5Hβ), β 6.72-6.69 (m, 1H, Coumarin-6H), δ 6.65 (d, J=1.83 Hz, 0.3H, Coumarin-8Hβ), δ 6.60 (d, J=1.83 Hz, 0.7H, Coumarin-8Hα), δ 5.18 (d, J=3.20 Hz, 0.7H, H-1α), δ 4.55 (d, J=8.24 Hz, 0.3H, H-1β), δ 3.90-3.78 (m, 3.7H, H-3α, H-5, H-6, H-6'), δ 3.51-3.33 (m, 2H, H-2α, H-3β, H-4), δ 3.25 (dd, J=1.37 Hz, 8.23 Hz, 0.3H, H-2β), δ 2.06 (s, 3H, Me); ESI-MS: C$_{16}$H$_{20}$NO$_7$ [M+H]$^+$ calc.: 338.1, found: 338.1. maximum excitation wavelength (Ex max) 361.0 nm, maximum fluorescence wavelength (Em max) 460.0 nm.

3-MCLG can be synthesized in the same way as in 3-MCDG using L-glucosamine.

Example 7: Synthesis of 4-TFMCDG

4-TFMCDG was synthesized as follows:

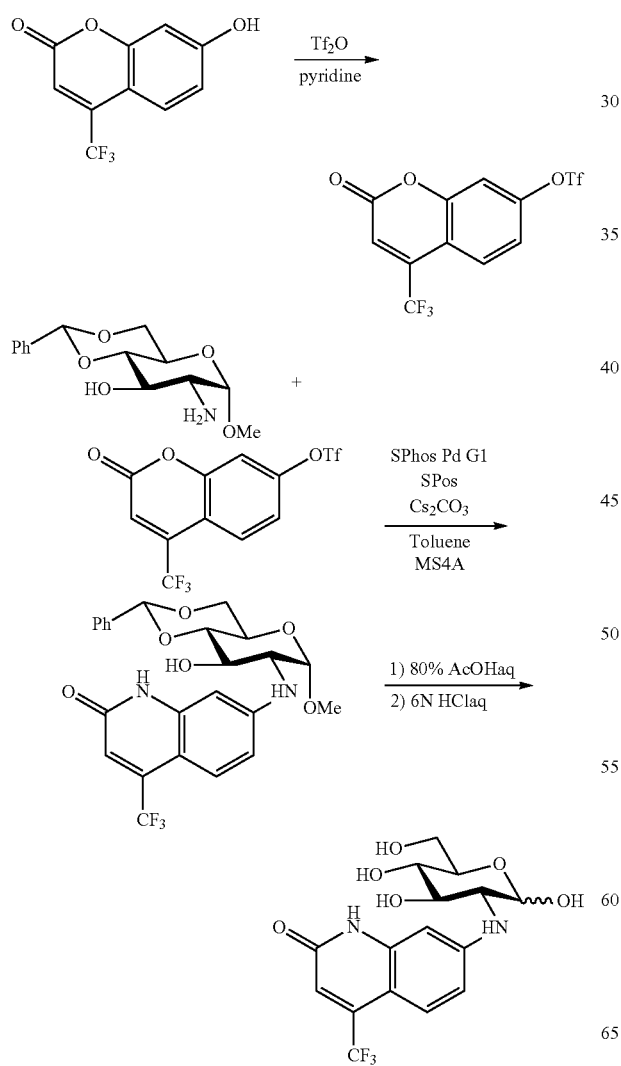

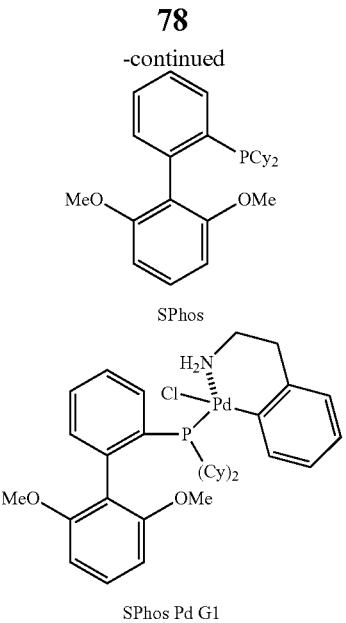

(7-1) Synthesis of 2-oxo-2H-4-trifluoromethyl-chromen-7-yl trifluoromethanesulfonate Represented by Following Formula

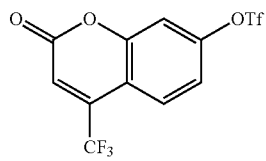 [SMILES: O=c1cc(C(F)(F)F)c2ccc(OS(=O)(=O)C(F)(F)F)cc2o1]

In an argon atmosphere, 4-trifluoromethylumbelliferone (0.2 g, 0.869 mmol) was dissolved in pyridine (4.3 mL), and the solution was cooled in ice. Trifluoromethanesulfonic anhydride (0.16 mL, 0.956 mmol) was added dropwise thereto. Then, the mixture was stirred at room temperature for 2 hours. After the completion of the reaction, the reaction mixture was subjected to extraction with ethyl acetate, and the extract was washed with 1 N hydrochloric acid and saturated saline. The organic layer was dried over anhydrous sodium sulfate, and the solvent was distilled off. The residue was purified using a silica gel column (SiO$_2$, 40 g) to obtain the compound (285 mg, 90%) as a white solid.

(7-2) Synthesis of methyl 4,6-O-benzylidene-2-deoxy-2-(2-oxo-2H-4-trifluoromethyl-chromen-7-yl) amino-α-D-glucopyranoside Represented by Following Formula

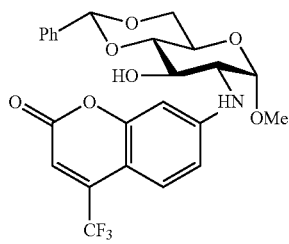

In an argon atmosphere, toluene (5.5 mL) was added to activated molecular sieve 4A (pellet), methyl 4,6-O-benzylidene-2-deoxy-2-amino-α-D-glucopyranoside (141.4 mg, 0.414 mmol), 2-oxo-2H-4-trifluoromethyl-chromen-7-yl trifluoromethanesulfonate (100 mg, 0.276 mmol), SPhos Pd G1 (chloro(2-dicyclohexylphosphino-2',6'-dimethoxy-1,1'-biphenyl)[2-(2-aminoethylphenyl)]palladium(II)) (63 mg, 82.8 μmol) (Sigma-Aldrich), SPhos (2-dicyclohexylphosphino-2',6'-dimethoxybiphenyl) (34 mg, 82.8 μmol) (Sigma-Aldrich), and Cs₂CO₃ (224.8 mg, 690 μmol), and the mixture was refluxed for 2 hours. After the completion of the reaction, the reaction mixture was subjected to extraction with ethyl acetate, and the extract was washed with 1 N hydrochloric acid and saturated saline. The organic layer was dried over anhydrous sodium sulfate, and the solvent was distilled off. The residue was purified using a silica gel column (SiO₂, 40 g) to obtain the compound (42.3 mg, 31%) as a pale yellow solid.

(7-3) Synthesis of 2-deoxy-2-(2-oxo-2H-4-trifluoromethyl-chromen-7-yl)amino-D-glucose (4-TFM-CDG) Represented by Following Formula

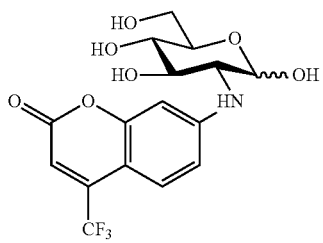

The compound methyl 4,6-O-benzylidene-2-deoxy-2-(2-oxo-2H-4-trifluoromethyl-chromen-7-yl)amino-α-D-glucopyranoside (42 mg, 85.1 μmol) was dissolved in an 80% aqueous acetic acid solution (2 mL), and the solution was heated to 50° C. and stirred for 2 hours. After the completion of the reaction, the solvent was distilled off. 6 N hydrochloric acid (2 mL) was added to the residue, and the mixture was heated to 80° C. and stirred for 3 hours. After the completion of the reaction, the solvent was distilled off. The residue was dissolved in water. The solution was purified by reverse-phase HPLC. A fraction containing the compound of interest was freeze-dried to obtain the compound as a yellow solid. The yield was 18 mg, and the percent yield was 54%. Also, results of analyzing the obtained compound are as follows.

¹H NMR (CD₃OD, 400 MHz): δ 7.43-7.38 (m, 1H, Coumarin-5H), δ 6.79 (dd, J=2.29 Hz, J=9.15 Hz, 0.7H, Coumarin-5Hα), δ 6.78 (dd, J=2.29 Hz, J=8.69 Hz, 0.3H, Coumarin-5Hβ), δ 6.72 (d, J=2.29 Hz, 0.3H, Coumarin-6Hβ), δ 6.69 (d, J=2.29 Hz, 0.7H, Coumarin-6Hα), δ 6.37 (s, 0.7H, Coumarin-8Hα), δ 6.35 (s, 0.3H, Coumarin-8Hβ), δ 5.18 (d, J=3.20 Hz, 0.7H, H-1α), δ 4.57 (d, J=8.24 Hz, 0.3H, H-1β), δ 3.90-3.33 (m, 6H, H-2, H-3, H-4, H-5, H-6, H-6'); ESI-MS: C₁₆H₁₆F₃NO₇ [M+H]⁺ calc.: 392.1, found: 392.1. maximum excitation wavelength (Ex max) 380.0 nm, maximum fluorescence wavelength (Em max) 500.0 nm.

Example 8: Synthesis of 3-TFMCDG

3-TFMCDG was synthesized as follows:

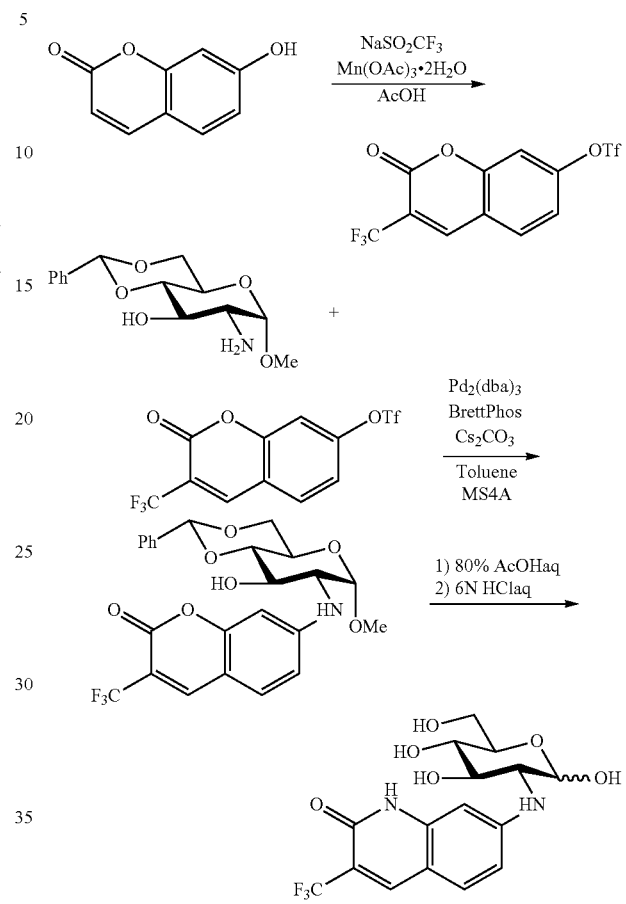

(8-1) Synthesis of 2-oxo-3-trifluoromethyl-2H-chromen-7-yl trifluoromethanesulfonate Represented by Following Formula

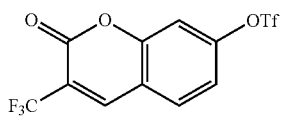

Acetic acid (17.5 mL) was added to 2-oxo-2H-chromen-7-yl trifluoromethanesulfonate (500 mg, 1.71 mmol), sodium trifluoromethanesulfinate (400 mg, 2.56 mmol), and manganese(III) acetate dihydrate (914 mg, 3.41 mmol), and the mixture was stirred at room temperature. After 19 hours, sodium trifluoromethanesulfinate (400 mg, 2.56 mmol) and manganese(III) acetate dihydrate (914 mg, 3.41 mmol) were further added thereto. After another 3 hours, sodium trifluoromethanesulfinate (400 mg, 2.56 mmol) was further added thereto. 26.5 hours after the start of the reaction, the reaction was terminated by the addition of water. The reaction mixture was subjected to extraction with ethyl acetate, and the extract was washed with saturated saline. The organic layer was dried over anhydrous sodium sulfate, and the solvent was distilled off. The residue was purified using a silica gel column (SiO$_2$, 40 g) to obtain the compound (258.5 mg, 42%) as a white solid.

(8-2) Synthesis of methyl 4,6-O-benzylidene-2-deoxy-2-(2-oxo-3-trifluoromethyl-2H-chromen-7-yl)amino-α-D-glucopyranoside Represented by Following Formula

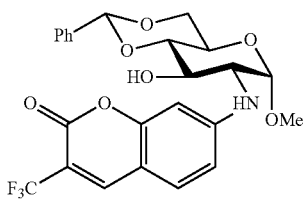

In an argon atmosphere, toluene (0.97 mL) was added to activated molecular sieve 4A (pellet), methyl 4,6-O-benzylidene-2-deoxy-2-amino-α-D-glucopyranoside (39.6 mg, 116 μmol), 2-oxo-3-trifluoromethyl-2H-chromen-7-yl trifluoromethanesulfonate (35 mg, 96.6 μmol), Pd$_2$(dba)$_3$ (tris(dibenzylideneacetone)dipalladium(0)) (8.8 mg, 9.66 μmol), BrettPhos (2-(dicyclohexylphosphino)-3,6-dimethoxy-2',4',6'-triisopropyl-1,1'-biphenyl) (Sigma-Aldrich) (10.4 mg, 19.3 μmol), and Cs$_2$CO$_3$ (31.4 mg, 96.6 μmol), and the mixture was refluxed for 1 hour. After the completion of the reaction, the reaction mixture was subjected to extraction with ethyl acetate, and the extract was washed with saturated saline. The organic layer was dried over anhydrous sodium sulfate, and the solvent was distilled off. The residue was purified using a silica gel column (SiO$_2$, 16 g) to obtain the compound (13.8 mg, 29%) as a pale yellow solid.

(8-3) Synthesis of 2-deoxy-2-(2-oxo-3-trifluoromethyl-2H-chromen-7-yl)amino-D-glucose (3-TFM-CDG) Represented by Following Formula

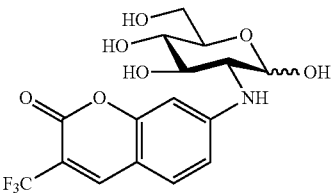

The compound methyl 4,6-O-benzylidene-2-deoxy-2-(2-oxo-3-trifluoromethyl-2H-chromen-7-yl)amino-α-D-glucopyranoside (40 mg, 94 μmol) was dissolved in an 80% aqueous acetic acid solution (3 mL), and the solution was heated to 50° C. and stirred for 6 hours. After the completion of the reaction, the solvent was distilled off. 6 N hydrochloric acid (3 mL) was added to the residue, and the mixture was heated to 80° C. and stirred for 5 hours. After the completion of the reaction, the solvent was distilled off. The residue was dissolved in dimethylformamide. The solution was purified by reverse-phase HPLC. A fraction containing the compound of interest was freeze-dried to obtain the compound as a pale yellow solid.

The yield was 23.2 mg, and the percent yield was 27%. Also, results of analyzing the obtained compound are as follows.

$^1$H NMR (CD$_3$OD, 400 MHz): δ 8.17 (s, 1H, Coumarin-4H), δ 7.41 (d, J=8.69 Hz, 0.7H, Coumarin-5Hα) δ 7.40 (d, J=8.69 Hz, 0.3H, Coumarin-5Hβ), β 6.80-6.76 (m, 1H, Coumarin-6H), δ 6.66 (d, J=1.83 Hz, 0.3H, Coumarin-8Hβ), δ 6.64 (d, J=2.29 Hz, 0.7H, Coumarin-8Hα), δ 5.18 (d, J=3.20 Hz, 0.7H, H-1α), δ 4.58 (d, J=7.78 Hz, 0.3H, H-1β), δ 3.91-3.68 (m, H-3, H-5α, H-6, H-6'), δ 3.58 (dd, J=10.1 Hz, 3.20 Hz, 0.7H, H-2α), δ 3.49-3.34 (m, 2.6H, H-2β, H-4, H-5β); ESI-MS: C$_{16}$H$_{17}$F$_3$NO$_7$ [M+H]$^+$ calc.: 392.1, found: 392.1. maximum excitation wavelength (Ex max) 381.0 nm, maximum fluorescence wavelength (Em max) 455.0 nm.

Example 9: Synthesis of 6-F-CDG

6-F-CDG was synthesized as follows:

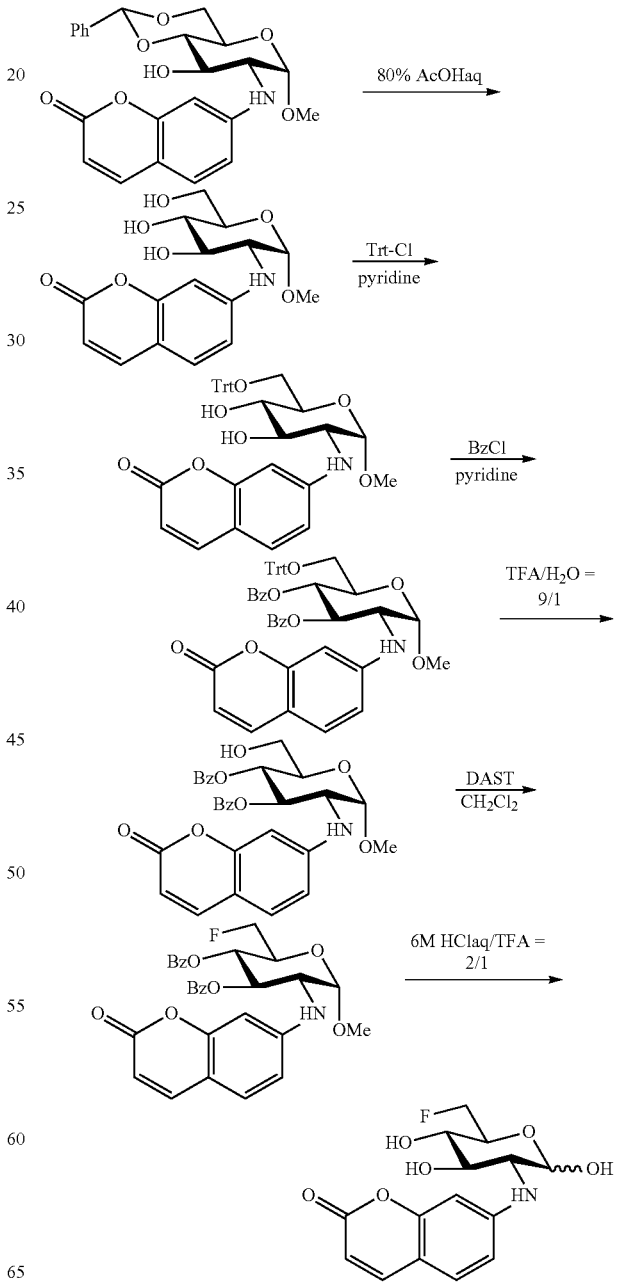

(9-1) Synthesis of methyl 2-deoxy-2-(2-oxo-2H-chromen-7-yl)amino-α-D-glucopyranoside Represented by Following Formula

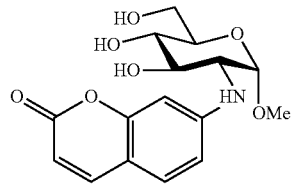

The compound methyl 4,6-O-benzylidene-2-deoxy-2-(2-oxo-2H-chromen-7-yl)amino-α-D-glucopyranoside (200 mg, 470.1 μmol) was dissolved in an 80% aqueous acetic acid solution (5 mL), and the solution was heated to 50° C. and stirred for 2 hours. After the completion of the reaction, the solvent was distilled off. The residue was freeze-dried from 1,4-dioxane to obtain the compound (159 mg, quant.) as a pale yellow solid.

(9-2) Synthesis of methyl 3,4-di-O-benzoyl-2-deoxy-2-(2-oxo-2H-chromen-7-yl)amino-α-D-glucopyranoside Represented by Following Formula

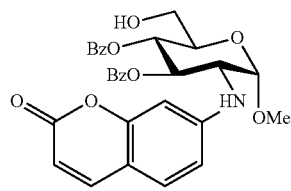

In an argon atmosphere, methyl 2-deoxy-2-(2-oxo-2H-chromen-7-yl)amino-α-D-glucopyranoside (50 mg, 148 μmol) was dissolved by the addition of pyridine (1.5 mL). To the solution, triphenylmethyl chloride (206 mg, 740 μmol) was added, and the mixture was heated to 60° C. After 2 hours, the reaction mixture was allowed to cool, neutralized with a saturated aqueous solution of sodium bicarbonate, and subjected to extraction with ethyl acetate, and the extract was washed with a saturated aqueous solution of sodium bicarbonate and saturated saline. The organic layer was dried over anhydrous sodium sulfate, and the solvent was distilled off. In an argon atmosphere, the obtained residue was dissolved by the addition of pyridine (1.5 mL). To the solution, benzoyl chloride (140 μL, 1.205 mmol) was added, and the mixture was heated to 40° C. After 2 hours, the reaction mixture was subjected to extraction with ethyl acetate, and the extract was washed with a saturated aqueous solution of sodium bicarbonate and saturated saline. The organic layer was dried over anhydrous sodium sulfate, and the solvent was distilled off. An ice-cold 90% aqueous trifluoroacetic acid solution (1.5 mL) was added to the obtained residue. After 30 minutes, the mixture was diluted with chloroform and washed with a saturated aqueous solution of sodium bicarbonate and saturated saline. The organic layer was dried over anhydrous sodium sulfate, and the solvent was distilled off. The residue was purified using a silica gel column (SiO$_2$, 40 g) to obtain the compound (47.7 mg, 59%) as a pale yellow solid.

(9-3) Synthesis of methyl 3,4-di-O-benzoyl-2,6-dideoxy-6-fluoro-2-(2-oxo-2H-chromen-7-yl)amino-α-D-glucopyranoside Represented by Following Formula

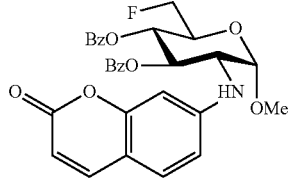

In an argon atmosphere, methyl 2-deoxy-2-(2-oxo-2H-chromen-7-yl)amino-α-D-glucopyranoside (220 mg, 403 μmol) was dissolved in dichloromethane (10 mL), and the solution was cooled to −17° C. N,N-Diethylaminosulfur trifluoride (320 μL, 2.42 mmol) was added dropwise thereto, and the mixture was heated to room temperature. After 2 hours, the mixture was cooled to −17° C. N,N-Diethylaminosulfur trifluoride (320 μL, 2.42 mmol) was further added dropwise thereto, and the mixture was heated to room temperature. 4 hours after the start of the reaction, the reaction mixture was cooled in ice, and the reaction was terminated by the addition of methanol. The reaction mixture was subjected to extraction with ethyl acetate, and the extract was washed with saturated saline. The organic layer was dried over anhydrous sodium sulfate, and the solvent was distilled off. The residue was purified using a silica gel column (SiO$_2$, 40 g) to obtain the compound (104 mg, 47%) as a pale yellow solid.

(9-4) Synthesis of 2,6-dideoxy-6-fluoro-2-(2-oxo-2H-chromen-7-yl)amino-D-glucose (6-F-CDG) Represented by Following Formula

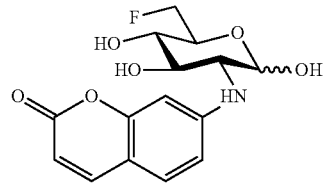

Acetic acid (1 mL) and 6 N hydrochloric acid (20 mL) were added to the compound methyl 3,4-di-O-benzoyl-2,6-dideoxy-6-fluoro-2-(2-oxo-2H-chromen-7-yl)amino-α-D-glucopyranoside (104 mg, 190 μmol), and the mixture was heated to 80° C. and stirred for 4 days. Then, the solvent was distilled off. Trifluoroacetic acid (5 mL) and 6 N hydrochloric acid (10 mL) were added to the residue, and the mixture was heated to 80° C. and stirred for 3 days. After the completion of the reaction, the solvent was distilled off. The residue was dissolved in dimethylformamide. The solution was purified by reverse-phase HPLC. A fraction containing the compound of interest was freeze-dried to obtain the compound as a pale yellow solid.

The yield was 10.2 mg, and the percent yield was 17%. Also, results of analyzing the obtained compound are as follows.

$^1$H NMR (CD$_3$OD, 400 MHz): δ 7.74 (d, J=9.15 Hz, 0.7H, Coumarin-4Hα), δ 7.74 (d, J=9.15 Hz, 0.3H, Coumarin-4Hβ), δ 7.30 (d, J=8.69 Hz, 0.7H, Coumarin-5Hα), δ 7.27 (d, J=8.24 Hz, 0.3H, Coumarin-5Hβ), δ 6.75-6.72 (m, 1H, Coumarin-6H), δ 6.66 (d, J=1.83 Hz, 0.3H, Coumarin-8Hβ), δ 6.62 (d, J=2.29 Hz, 0.7H, Coumarin-8Hα), δ 6.00 (d, J=9.15 Hz, 0.7H, Coumarin-3Hα), δ 5.98 (d, J=9.15 Hz, 0.3H, Coumarin-3Hβ), δ 5.19 (d, J=3.20 Hz, 0.7H, H-1α), δ 4.75-4.51 (m, 2.2H, H-1β, H-3β, H-5β, H-6, H-6'β), δ 3.97 (dddd, J=27.5 Hz, 10.1 Hz, 4.1 Hz, 1.3 Hz, 0.7H, H-6'α), δ 3.78 (t, J=9.61 Hz, 0.7H, H-3α), δ 3.55-3.42 (m, 2.4H, H-2α, H-4, H-5α); ESI-MS: $C_{15}H_{17}FNO_6$ $[M+H]^+$ calc.: 326.1, found: 326.1.

Example 10: Synthesis of 4-F-CDG

4-F-CDG was synthesized as follows:

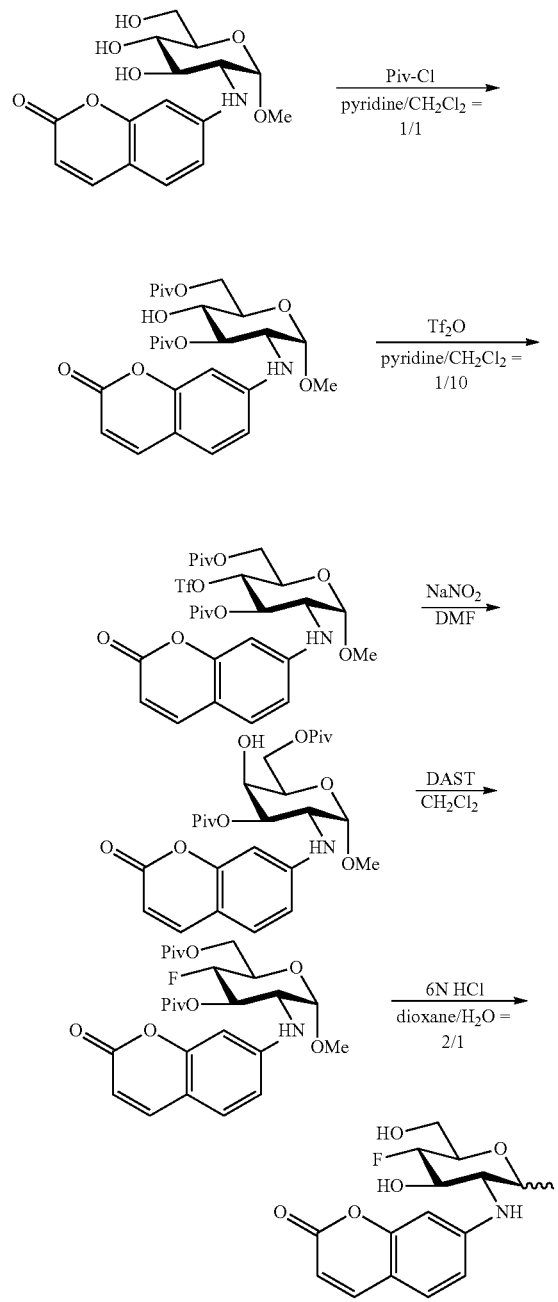

(10-1) Synthesis of methyl 2-deoxy-2-(2-oxo-2H-chromen-7-yl)amino-3,6-di-O-pivaloyl-α-D-glucopyranoside Represented by Following Formula

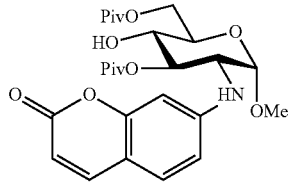

In an argon atmosphere, methyl 2-deoxy-2-(2-oxo-2H-chromen-7-yl)amino-α-D-glucopyranoside (435 mg, 1.29 mmol) was dissolved by the addition of pyridine (6.5 mL) and dichloromethane (6.5 mL), and the solution was cooled in ice. Pivaloyl chloride (565 μL, 4.59 mmol) was added dropwise thereto, and the mixture was heated to room temperature. After 1 hour, the reaction was terminated by the dropwise addition of a saturated aqueous solution of sodium bicarbonate. The reaction mixture was subjected to extraction with ethyl acetate, and the extract was washed with a saturated aqueous solution of sodium bicarbonate and saturated saline. The organic layer was dried over anhydrous sodium sulfate, and the solvent was distilled off. The residue was purified using a silica gel column ($SiO_2$, 40 g) to obtain the compound (431.8 mg, 66%) as a pale yellow solid.

(10-2) Synthesis of methyl 2-deoxy-2-(2-oxo-2H-chromen-7-yl)amino-3,6-di-O-pivaloyl-α-D-galactopyranoside Represented by Following Formula

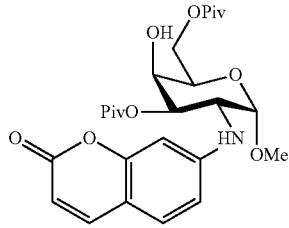

In an argon atmosphere, methyl 2-deoxy-2-(2-oxo-2H-chromen-7-yl)amino-3,6-di-O-pivaloyl-α-D-glucopyranoside (150 mg, 297 μmol) was dissolved in dichloromethane (10 mL) and pyridine (1 mL), and the solution was cooled in ice. Trifluoromethanesulfonic anhydride (74 μL, 445 μmol) was added dropwise thereto, and the mixture was heated to room temperature. After 1.5 hours, the reaction mixture was subjected to extraction with ethyl acetate, and the extract was washed with a saturated aqueous solution of sodium bicarbonate and saturated saline. The organic layer was dried over anhydrous sodium sulfate, and the solvent was distilled off. In an argon atmosphere, the residue was dissolved by the addition of dimethylformamide (3 mL), and the solution was cooled in ice. Sodium nitrite (71.7 mg, 69 μmol) was added thereto. After 1.5 hours, the reaction solution was purified with a silica gel column ($SiO_2$, 16 g). The compound (79.5 mg, 53%) was obtained as a pale yellow solid.

(10-3) Synthesis of methyl 2,4-dideoxy-4-fluoro-2-(2-oxo-2H-chromen-7-yl)amino-3,6-di-O-pivaloyl-α-D-glucopyranoside Represented by Following Formula

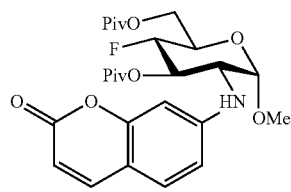

In an argon atmosphere, methyl 2-deoxy-2-(2-oxo-2H-chromen-7-yl)amino-3,6-di-O-pivaloyl-α-D-galactopyranoside (225 mg, 445 µmol) was dissolved in dichloromethane (8.9 mL), and the solution was cooled to −40° C. N,N-Diethylaminosulfur trifluoride (352.8 µL, 2.67 mmol) was added dropwise thereto, and the mixture was heated to room temperature. 4 hours after the start of the reaction, the reaction mixture was cooled to −20° C., and the reaction was terminated by the addition of methanol. After extraction with chloroform, the extract was washed with saturated saline. The organic layer was dried over anhydrous sodium sulfate, and the solvent was distilled off. The residue was purified using a silica gel column ($SiO_2$, 40 g) to obtain the compound (174.7 mg, 77%) as a pale yellow solid.

(10-4) Synthesis of 2,4-dideoxy-4-fluoro-2-(2-oxo-2H-chromen-7-yl)amino-D-glucose (4-F-CDG) Represented by Following Formula

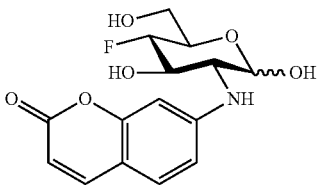

The compound methyl 2,4-dideoxy-4-fluoro-2-(2-oxo-2H-chromen-7-yl)amino-3,6-di-O-pivaloyl-α-D-glucopyranoside (170 mg, 335 µmol) was dissolved in a solution of 4.5 N hydrogen chloride in dioxane (6 mL) and 6 N hydrochloric acid (3 mL), and the solution was heated to 80° C. and stirred for 6 hours. After the completion of the reaction, the solvent was distilled off. The residue was dissolved in dimethylformamide. The solution was purified by reverse-phase HPLC. A fraction containing the compound of interest was freeze-dried to obtain the compound as a pale yellow solid.

The yield was 8.4 mg, and the percent yield was 8%. Also, results of analyzing the obtained compound are as follows.
$^1$H NMR ($CD_3OD$, 400 MHz): δ 7.75 (d, J=9.61 Hz, 1H, Coumarin-4H), δ 7.30 (d, J=8.69 Hz, 1H, Coumarin-5H), δ 6.75 (dd, J=8.24 Hz, 1.83 Hz, 1H, Coumarin-6H), δ 6.67 (d, J=1.83 Hz, 0.3H, Coumarin-8Hβ), δ 6.63 (d, J=2.29 Hz, 0.7H, Coumarin-8Hα), δ 6.01 (d, J=9.15 Hz, 0.7H, Coumarin-3Hα), δ 5.99 (d, J=9.15 Hz, 0.3H, Coumarin-3Hβ), δ 5.18 (t, J=3.20 Hz, 0.7H, H-1α), δ 4.61 (d, J=7.78 Hz, 0.3H, H-1β), δ 4.40 (ddd, J=51.2 Hz, 8.69 Hz, 1.37 Hz, 0.7H, H-4α), δ 4.35 (ddd, J=50.8 Hz, 8.69 Hz, 0.92 Hz, 0.3H, H-4β), δ 4.06-3.98 (m, 1.7H, H-3α, H-6), δ 3.88-3.48 (m, 2.6H, H-2β, H-3β, H-5, H-6'), δ 3.36 (d, J=10.1 Hz, 0.7H, H-2α); ESI-MS: $C_{15}H_{17}FNO_6$ $[M+H]^+$ calc.: 326.1, found: 326.1.

(7) Fluorescence Spectrum

The fluorescence spectra of CDG synthesized in (1) and QDG synthesized in (2) were compared with the fluorescence spectrum of 2-NBDLG (manufactured by Peptide Institute, Inc.). The results are shown in FIG. 1.

The numeric values described above the graph denote the fluorescence maximum of CDG and QDG, respectively. It is evident that the fluorescence maximum was largely shifted to shorter wavelength as compared with the fluorescence maximum of 2-NBDLG present around 550 nm. Thus, even if CDG (or CLG that exhibits the same fluorescence spectrum as CDG) or QDG (or QLG that exhibits the same fluorescence spectrum as QDG) can be used at the same time with 2-NBDLG (or 2-NBDG that exhibits the same fluorescence spectrum as 2-NBDLG), these derivatives can be easily distinguished from each other based on the difference in fluorescence wavelength (the principal spectrum of 2-NBDLG was present at 500 nm or greater, and a small peak and valley on the spectrum seen at 500 nm or smaller were influenced by excitation light).

Example 11: Influence of Cytochalasin B (CB) on Increase in Fluorescence Intensity Caused by Administration of CDG to Mouse Insulinoma Cell (MIN6)

Increase in fluorescence intensity caused by the administration of CDG, and the influence of a glucose transporter (GLUT) inhibitor CB thereon were confirmed by targeting MIN6 cells.

(Experimental Method)
(1) Preparation of Mouse Insulinoma Cell (MIN6)

A 96-well clear-bottom plate having wells of 8 rows (A to H) and 12 columns (1 to 12) (µClear-PLATE, Greiner Bio-One, BLACK) was used in measurement. A culture solution containing MIN6 cells suspended at a density of $60×10^4$ cells/mL was added dropwise at 10 µL/well to the central portion of the well, and then, the plate was left standing for 40 minutes in an incubator for fixation. The cells were cultured by the addition of a culture solution at 200 µL/well (6000 cells/well). For layout, the cells were seeded to wells B to H on the third column and wells A to G on the fifth column. Medium replacement was performed by replacing half the amount with a fresh one once every two days at 0 to 4 DIV (days in vitro) and every day at 5 DIV or later. The cells were subjected to the experiment at culture days 10 to 15 (10 to 15 DIV). Well A on the third column and well H on the fifth column were used as controls for checking whether or not washout was accurately performed without seeding the cells. The wells on the fourth column were used as cell-free blanks using only a Krebs-Ringer buffer solution (KRB, containing 0.1 mM gap junction inhibitor carbenoxolone and 5.6 mM glucose).

(1-1) Culture of MIN6 Cell

The MIN6 cells used were cells kindly provided by professor Junichi Miyazaki (Osaka University) and subcultured 6 to 10 times. Half the amount of the culture solution was replaced with a fresh one once every two days.

(1-2) Composition of Culture Solution Used in Culture of MIN6 Cell 13.4 g of high glucose-containing Dulbecco's modified Eagle's Medium (DMEM-HG) (Sigma-Aldrich, #D5648), 3.4 g of $NaHCO_3$, and 5 µL of 2-mercaptoethanol were dissolved in 1 L of ultrapure water, and the pH of the solution was adjusted to 7.30 to 7.35 in a $CO_2$ incubator of 37° C. The culture solution was supplemented with fetal bovine serum (Hyclone, Cat# SH30070.03) at a final concentration of 10% and penicillin-streptomycin at a final concentration of 0.5%.

(2) Preparation of CDG Solution and Additional Fluorescent Sugar Derivative

Preparation of CDG Solution

The whole amount of the 0.5 mg CDG vial was recovered using 0.73 mL in total of 10% dimethyl sulfoxide (DMSO) and dissolved by addition to 7.0 ml of a KRB solution for image acquisition according to the method described in Non Patent Literature 2. The solution was applied at a final concentration of 100 μM to the cells.

Preparation of 2-NBDG Solution

The whole amount of one 0.5 mg 2-NBDG vial was dissolved in 1.83 mL of a KRB solution for data acquisition. The solution was applied at a final concentration of 200 μM to the cells.

(2-1) KRB Solution for Data Acquisition

Composition of Volume Used in Data Acquisition with Fluorescence Microplate Reader 129.0 mM NaCl, 4.75 mM KCl, 1.19 mM $KH_2PO_4$, 1.19 mM $MgSO_4.7H_2O$, 1.0 mM $CaCl_2.2H_2O$, 5.02 mM $NaHCO_3$, 5.6 mM D-glucose, and 10 mM HEPES (the pH was adjusted to 7.35 with 1 M NaOH). 0.1 mM carbenoxolone (Sigma-Aldrich, #C4790) was added thereto for the purpose of inhibiting the entrance and exit of fluorescently labeled glucose by way of gap junction/hemichannel. This KRB solution for data acquisition was used as a solution for preparing the CDG solution and the additional fluorescent sugar derivative solution.

(3) Fluorescence Measurement

CDG and 2-NBDG were each independently administered to the wells on the third and fifth columns using an 8-channel pipette such that these derivatives were alternately placed on the same plate. Before the administration, the autofluorescence of each well was measured in advance using a fluorescence microplate reader (Flex Station, Molecular Devices, LLC). The measurement conditions involved Ex of 367 nm, Em of 455 nm, and cut off of 420 nm on the CDG detector side (blue channel) and Ex of 470 nm, Em of 540 nm, and cut off of 495 nm on the 2-NBDG detector side (green channel). The measurement was conducted at Bottom Read, Averaging 3, and Photomultiplier sensitivity high. Well Scan Mode was used as a measurement method. The Well Scan Mode each independently measures 9 observation regions (diameter: 1.5 mm) divided from one well.

Further, CB (final concentration: 10 μM) was preliminarily administered to wells for the measurement of the effect of the glucose transport inhibitor cytochalasin B (CB) from 2 minutes before the administration of CDG, and KRB was added to the other wells. CDG and 2-NBDG were administered at 37° C. for 5 minutes.

After the completion of the administration, the operation of diluting the fluorescent solution in each well using 300 of a KRB solution for 30 seconds was repeated at the predetermined number of times. The number of repetitions was determined such that fluorescence intensity exhibited by well A on the third column and well H on the fifth column selected as a control group was at the same level as the fluorescence intensity of the cell-free blank wells. Complete washout was confirmed in each run of the experiment. In the case of CDG and 2-NBDG, this washout process required 8 minutes. Therefore, fluorescence measurement was carried out 9 minutes after the administration.

According to this method, even if cells having disrupted membrane integrity have temporarily taken CDG and 2-NBDG therein after contact with these compounds, the compounds are already drained to the outside of the cells and washed out at the time of measurement. Therefore, their contribution to increase in fluorescence intensity in the whole observation area was judged as being ignorable.

Figure 2:
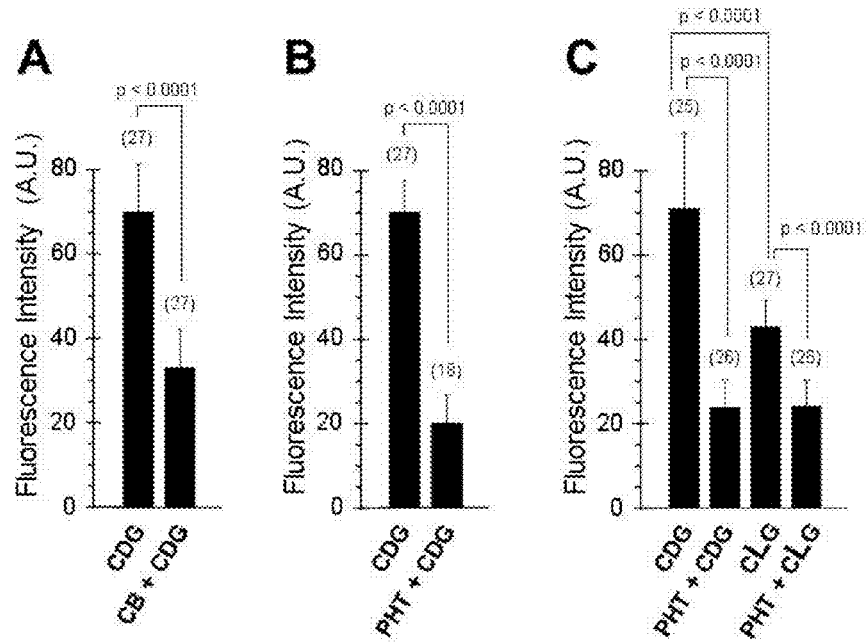
FIG. 2 shows results of confirming the uptake of CDG (100 μM) into mouse insulinoma cells (MIN6), and the influence of a glucose transport inhibitor on the uptake.

The effect of the glucose transport inhibitor on change in fluorescence intensity caused by the application of the D-glucose derivative (CDG) to the MIN6 cells at culture day 13 was confirmed by use of the method described above. Increase in the fluorescence intensity of the cells was measured in the presence and absence of CB (10 μM). The results are shown in FIG. 2A.

In the presence of CB, the fluorescence intensity was largely attenuated as compared with the absence of the inhibitor, suggesting that GLUT-mediated uptake contributes not a little to the cellular uptake of CDG. The numeral within the parentheses denotes the number of effective observation regions. Two similar experiments were independently conducted and both produced similar results. The fluorescence intensity was decreased to 47.3% and 42.9%, respectively, on average in the presence of CB relative to the absence of CB.

The unpaired t-test or the ANOVA and Bonferroni-Dunn test was used in the statistics (the same holds true for the description below).

Example 12: Influence of Phloretin (PHT) on Increase in Fluorescence Intensity Caused by Administration of CDG to MIN6 Cell Increase in fluorescence intensity caused by the administration of CDG to the MIN6 cells at culture day 13, and the influence of PHT functioning as a GLUT inhibitor and a water channel inhibitor thereon were confirmed in the same way as in Example 11. The results are shown in FIG. 2B.

PHT (final concentration: 150 μM) was preliminarily administered to wells for the measurement of the effect of PHT from 1 minute before the administration of CDG, and KRB was added to the other wells. CDG and 2-NBDG were administered at 37° C. for 5 minutes.

In the presence of PHT, the fluorescence intensity was remarkably attenuated as compared with the absence of the inhibitor. Two similar experiments were independently conducted and both produced similar results. The fluorescence intensity was decreased to 28.5% and 28.8%, respectively, on average in the presence of PHT relative to the absence of PHT. The degree of this inhibitory effect of PHT was stronger than the inhibitory effect of CB shown in FIG. 2A, suggesting the possibility that a pathway other than GLUT is also involved, together with GLUT, in the cellular uptake of CDG.

Example 13: Influence of Phloretin (PHT) on Increase in Fluorescence Intensity Caused by Administration of CDG or CLG to MIN6 Cell Increase in fluorescence intensity caused by the administration of CDG or CLG to the MIN6 cells at culture day 15, and the inhibitory effect of PHT thereon were compared on the same dish.

MIN6 cells on one 96-well dish were targeted where there were PHT-containing wells and PHT-free wells to which CDG and CLG were alternately administered. The administration solutions were concurrently administered using an 8-channel pipette. The dish was left standing for 5 minutes, and then, washout was also performed concurrently for the wells. Change in fluorescence intensity was measured on each observation region. The results are shown in FIG. 2C.

As a result of the experiment, increase in fluorescence intensity caused by the administration of the D-glucose derivative CDG was significantly inhibited by PHT serving as a GLUT inhibitor and a water channel inhibitor, as in the results of Example 12. Also, PHT significantly inhibited the uptake of the L-glucose derivative CLG.

It is to be noted that the fluorescence intensity was still increased not a little by the administration of CDG even in the presence of PHT, and the degree of this increase was almost the same as the degree of the increase in fluorescence intensity by CLG.

Furthermore, the increase in fluorescence intensity caused by the administration of the L-glucose derivative CLG was significantly smaller than the increase in fluorescence intensity caused by the administration of the D-glucose derivative CDG. This quantitatively demonstrated that the uptake of the blue fluorescent glucose derivatives CDG and CLG into mouse insulinoma MIN6 cells exhibits D/L stereoselectivity.

A previous case of quantitatively comparing fluorescent glucose derivatives taken into cells while exhibiting D/L stereoselectivity is the report of the present inventors as to the administration of the green glucose derivatives 2-NBDG and 2-NBDLG to MIN6 cells. In this case, the cellular uptake of the L-glucose derivative 2-NBDLG is always smaller than the cellular uptake of the D-glucose derivative 2-NBDG (see WO2012/133688 (Patent Literature 4)). D form-dominant uptake was also found in the combination of the blue D-glucose derivative CDG and the blue L-glucose derivative CLG of the present invention, suggesting the possibility of reflecting difference in the three-dimensional structure of glucose.

Comparative Example: Influence of Cytochalasin B (CB) or Phloretin (PHT) on Increase in Fluorescence Intensity Caused by Administration of Green Fluorescent D-Glucose Derivative 2-NBDG to MIN6 Cell The inhibitory effect of CB (10 μM) or PHT (150 μM) on increase in fluorescence intensity caused by the administration of the green fluorescent D-glucose derivative 2-NBDG was confirmed. On the same day as the experiment of Example 11, the same MIN6 cell series at 13 days after the start of culture was used, and the green fluorescent D-glucose derivative 2-NBDG was administered thereto to examine the inhibitory effect of CB (10 μM) or PHT (150 μM) on increase in fluorescence intensity.

Figure 3:
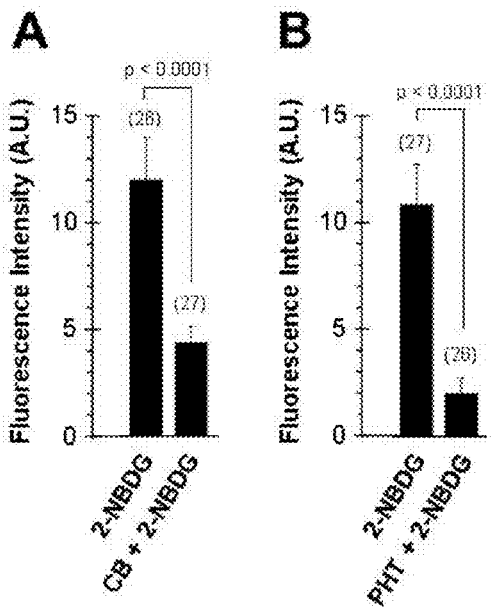
FIG. 3 shows results of examining the uptake of a green fluorescent D-glucose derivative 2-NBDG into mouse insulinoma cells (MIN6), and the inhibitory effect of CB or PHT on the uptake.

Specifically, a KRB solution containing 200 μM 2-NBDG was administered to the cells, which were then left standing for 5 minute, followed by washout. Increase in the fluorescence intensity of the cells between before and after the administration was measured. Each observation region was measured three times at an excitation light wavelength of 470 nm, a fluorescence acquisition wavelength of 540 nm, and a cutoff filter of 495 nm, and a mean thereof was calculated. The results are shown in FIG. 3.

The uptake of 2-NBDG into the MIN6 cells was significantly inhibited by CB and more strongly inhibited by PHT, like the previous report of the inventors (WO2012/133688 (Patent Literature 4)). Two experiments independently carried out both produced similar results. The fluorescence intensity was decreased to 30.8% and 36.4%, respectively, on average in the presence of CB relative to the absence of CB. The fluorescence intensity was decreased to 18.6% and 15.7%, respectively, on average in the presence of PHT relative to the absence of PHT. These results are similar to the inhibitory effects of CB and PHT on increase in fluorescence intensity caused by the administration of CDG as seen in FIGS. 2A and 2B. However, the uptake of 2-NBDG was remarkably attenuated in the presence of PHT, whereas the fluorescence intensity remained not a little even in the presence of PHT by the administration of CDG.

In this way, the comparison between 2-NBDG and CDG can offer information on the influence of difference in fluorescent group bound to D-glucose on cellular uptake, and important hints about transport pathways.

Figure 4:
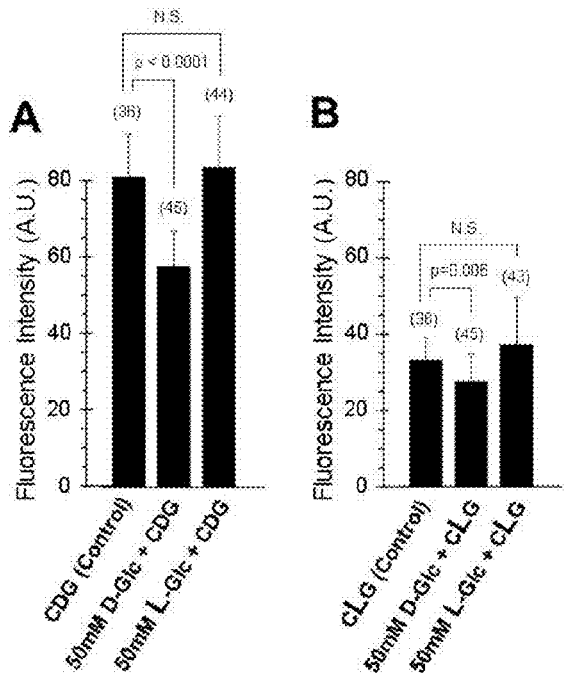
FIG. 4 shows results of confirming the uptake of CDG or CLG into mouse insulinoma cells (MIN6), and the influence of excessive D-glucose or L-glucose thereon.

Example 14: Influence of Excessive D-Glucose or Excessive L-Glucose on Increase in Fluorescence Intensity Caused by Administration of CDG to MIN6 Cell Whether or not increase in fluorescence intensity caused by the administration of the blue fluorescent D-glucose derivative CDG (100 μM) to the mouse insulinoma cells MIN6 at culture day 13 was inhibited by a large excess of D-glucose or L-glucose was examined. The blue fluorescent L-glucose derivative CLG was similarly analyzed as a control. The results are shown in FIG. 4. However, the following conditions were changed.

(Experimental method)

(1) Preparation of KRB Solution Dedicated to Excessive Glucose Administration Group Although the usual KRB solution contains 129 mM NaCl and 5.6 mM D-glucose, the osmotic pressure of a control solution (non-excessive glucose administration group solution) for this experiment was adjusted to 270 mOsm by substituting a portion of NaCl with choline-Cl, in order to equalize charge and osmotic pressure between the control solution and a KRB solution for excessive glucose administration. Also, the KRB solution for excessive glucose administration was allowed to contain NaCl and glucose according to the composition given below. In this respect, choline-Cl was added thereto in order to equalize osmotic pressure between this solution and the control solution (non-excessive glucose administration group solution).

100 mM NaCl and 5.6 mM D-glucose (non-excessive glucose administration group solution)

100 mM NaCl and 50 mM D-glucose (50 mM excessive D-glucose administration group solution)

100 mM NaCl, 50 mM L-glucose, and 5.6 mM D-glucose (50 mM excessive L-glucose administration group solution)

These dedicated KRB solutions were also used as a solution for preparing CDG and CLG solutions in this Example.

(2) Fluorescence Measurement

CDG and CLG were placed on different plates for the experiment. A CDG solution (or a CLG solution) prepared using each dedicated KRB solution was administered thereto using an 8-channel pipette (37° C., 5 min). Before the administration, replacement with each dedicated KRB solution was carried out in advance, and the autofluorescence of each well was measured with a fluorescence microplate reader. The time from the start of the replacement to immediately before the administration was approximately 28 minutes.

After the completion of the administration, first, the fluorescent solution in each well was temporarily diluted using 200 µL of the dedicated KRB solution and then diluted using 300 µL of the usual KRB solution.

The cellular uptake of D-glucose via GLUT present in the cell membrane requires that D-glucose should bind to a D-glucose-binding site in the GLUT protein. Specifically, the cellular uptake is considered to occur under the mechanism where: D-glucose binds to a D-glucose-binding site in the GLUT protein initially in an outward-open state in the cell membrane, and this binding alters the three-dimensional structure of GLUT to an inward-open state; subsequently, D-glucose is released from the binding site in GLUT and eventually transported into the cell from the exterior because the D-glucose faces the interior of the cell. In this respect, if a large excess of D-glucose is present in the solution, D-glucose occupies D-glucose-binding sites in GLUT. Thus, the transport rate into the cell does not exceed the fixed level and reaches a plateau.

Here, provided that the increase in fluorescence intensity caused by the administration of the blue fluorescent D-glucose derivative CDG to the MING cells is attributed to the GLUT-mediated cellular uptake of CDG as predicted from the results of FIG. 2A, it is considered that CDG binds to a D-glucose-binding site in GLUT prior to passage through GLUT. Thus, in this respect, if a large excess of D-glucose is present in the solution, D-glucose occupies D-glucose-binding sites in GLUT. Thus, it is predicted that CDG cannot bind to the binding site and the transport of CDG into the cell is also inhibited (competitive inhibition).

The influence of the presence of 50 mM L-glucose was also studied as a control in evaluating the influence of the presence of a large excess (50 mM) of D-glucose on increase in fluorescence intensity.

As a result of the experiment, the increase in fluorescence intensity caused by the administration of CDG was significantly suppressed in the presence of 50 mM D-glucose as compared with the control in the absence of D-glucose, but was not suppressed by the addition of 50 mM L-glucose (FIG. 4A). On the other hand, the increase in fluorescence intensity caused by the administration of CLG was also slightly inhibited by 50 mM D-glucose (FIG. 4B). However, the statistical difference therebetween was very slight. In fact, although the significant difference in the ANOVA and Bonferroni-Dunn test used in this experiment is regarded as being significant at a P value of less than 0.0083, the actual numeric value was 0.0060, which merely fell below the significance level by a narrow margin. The increase in fluorescence intensity caused by the administration of CLG was not inhibited by 50 mM L-glucose.

Figure 5:
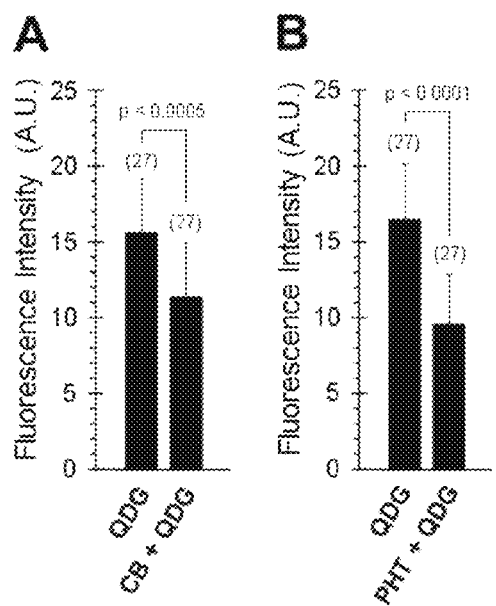
FIG. 5 shows results of confirming the uptake of QDG (100 μM) into mouse insulinoma cells (MIN6), and the influence of a glucose transport inhibitor on the uptake.

Example 15: Influence of Cytochalasin B (CB) or Phloretin (PHT) on Increase in Fluorescence Intensity Caused by Administration of QDG to MIN6 Cell Increase in fluorescence intensity caused by the administration of QDG and the influence of CB or PHT thereon were confirmed in the same way as in Examples 11 and 12 using QDG instead of CDG. The results are shown in FIG. 5.

(1) Preparation of QDG Solution

The whole amount of the 0.5 mg QDG vial was recovered using 0.71 mL in total of 10% dimethyl sulfoxide (DMSO) and dissolved by addition to 7.1 ml of KRB solution for image acquisition according to the method described in Non Patent Literature 2. The solution was applied at a final concentration of 100 µM to the cells.

As a result of the experiment, the increase in fluorescence intensity caused by the administration of QDG was signifi-cantly inhibited by CB (FIG. 5A) and more strongly inhibited in the presence of PHT (FIG. 5B). Each observation region was measured three times at an excitation light wavelength of 354 nm, a fluorescence acquisition wavelength of 435 nm, and a cutoff filter of 420 nm, and a mean of the results was calculated.

Example 16: Imaging of Tumor Cell Mass Consisting of Mouse Insulinoma Cells (MIN6) Using CDG/2-NBDLG/2-TRLG A fluorescent mixed solution containing 100 µM CDG, 100 µM 2-NBDLG, and 20 µM 2-TRLG (CDG/2-NBDLG/2-TRLG) was administered at 37° C. for 3 minutes to MIN6 cell masses (spheroids) at culture day 17, and fluorescent imaging was conducted.

(Experimental Method)

(1) Preparation of Mouse Insulinoma Cell (MIN6) Spheroid

10 µL of a culture solution containing MIN6 cells suspended at a density of $6 \times 10^4$ cells/mL was added dropwise onto each glass cover slip, and then, the glass cover slip was left standing for 40 minutes in an incubator for fixation to the glass surface. The cells were cultured by the addition of 3 mL of a culture solution (600 cells/slip). Spheroids were formed by continuing the culture for 15 to 17 days. Half the amount of the culture solution was replaced with a fresh one once every three days.

(1-1) Culture of MIN6 Cell

The MIN6 cells used were cells kindly provided by professor Junichi Miyazaki (Osaka University) and subcultured 6 to 10 times. Half the amount of the culture solution was replaced with a fresh one once every two days.

(1-2) Composition of Culture Solution Used in Culture of MIN6 Cell 13.4 g of high glucose-containing Dulbecco's modified Eagle's Medium (DMEM-HG) (Sigma-Aldrich, #D5648), 3.4 g of $NaHCO_3$, and 5 µL of 2-mercaptoethanol were dissolved in 1 L of ultrapure water, and the pH of the solution was adjusted to 7.30 to 7.35 in a $CO_2$ incubator of 37° C. The culture solution was supplemented with fetal bovine serum (Hyclone, Cat# SH30070.03) at a final concentration of 10% and penicillin-streptomycin at a final concentration of 0.5%.

(2) Preparation of CDG Solution and Mixed Solution with Additional Fluorescent Sugar Derivatives Preparation of CDG Solution The whole amount of the 0.5 mg CDG vial was recovered using 0.73 mL in total of 10% DMSO and dissolved by addition to 7.0 ml of a KRB solution for image acquisition according to the method described in Non Patent Literature 2.

Preparation of 2-NBDLG Solution

The whole amount of one 0.5 mg 2-NBDLG vial was dissolved in 7.3 mL of a KRB solution for image acquisition.

Preparation of 100 µM CDG+100 µM 2-NBDLG+20 µM 2-TRLG Mixed Solution

The CDG solution and the 2-NBDLG solution were mixed at a ratio of 1:1. The whole amount of the 0.2 mg 2-TRLG vial was recovered using 130 µL in total of DMSO and mixed with 13 ml of the CDG+2-NBDLG mixed solution according to the method described in Non Patent Literature 2. (final concentration: 100 µM CDG+100 µM 2-NBDLG+20 µM 2-TRLG mixed solution).

(2-1) KRB Solution for Image Acquisition

The KRB solution for image acquisition used was a solution having the following composition.

129.0 mM NaCl, 4.75 mM KCl, 1.19 mM $KH_2PO_4$, 1.19 mM $MgSO_4.7H_2O$, 1.0 mM $CaCl_2.2H_2O$, 5.02 mM $NaHCO_3$, 5.6 mM D-glucose, and 10 mM HEPES (the pH was adjusted to 7.35 with 1 M NaOH). 0.1 mM carbenoxolone (Sigma-Aldrich, #C4790) was added thereto for the purpose of inhibiting the entrance and exit of fluorescently labeled glucose by way of gap junction/hemichannel. This KRB solution for data acquisition was used for preparing the CDG solution and the mixed solution with the additional fluorescent sugar derivatives.

(3) Method for Observing MIN6 Cell Using Perfusion Chamber

The glass cover slip with the cultured MIN6 cells was transferred into the KRB solution for image acquisition in a perfusion chamber loaded on a stage of a fluorescence microscope, followed by measurement.

(3-1) Perfusion Chamber

A silicon plate of 1 mm thickness bored to have a streamline-shaped hole (10 mm wide×35 mm long) was placed via cover glass onto an aluminum heating control platform (Warner Instruments) having a round hole (diameter: 18 mm) for an objective lens at the bottom, and allowed to be in close contact with the cover glass.

The perfusion of the solution was carried out according to the method described in Non Patent Literature 2.

(4) Perfusate Feeding System to Perfusion Chamber

The KRB solution for image acquisition was warmed in advance in an aluminum syringe heater and supplied to the perfusion chamber through hydrostatic pressure. The perfusion rate was adjusted to 1.3±0.2 mL/min using a flow rate adjuster. Immediately before being introduced to the perfusion chamber, the solution was rewarmed via an inline heater so that the actually measured temperature of the perfusate in an observation region in the chamber was adjusted to 36±1° C. The CDG/2-NBDLG/2-TRLG mixed solution was able to be supplied in the same way as above and was switched with the KRB solution for image acquisition using an electromagnetic valve capable of controlling the opening and closing of the channel. The solution was removed using a vacuum pump capable of controlling suction pressure.

(5) Image Acquisition Condition

The fluorescence microscope used was NIKON ECLIPS-Ti, and images were acquired with a CCD camera Retiga 2000R.

CDG, 2-NBDLG, and 2-TRLG were each detected using the following filter cassette.
CDG (Blue Channel):
  Excitation 360/40 nm, Dichroic mirror 400 nm, Emission 460/50 nm.
2-NBDLG (Green Channel):
  Excitation 470/40 nm, Dichroic mirror 500 nm, Emission 545/55 nm.
2-TRLG (Red Channel):
  Excitation 567/15 nm, Dichroic mirror 593 nm, Emission 593 nm Long pass.

The objective lens used in this method was ×60 oil lens (Plan Fluor 60×/0.50-1.25 Oil). The images were acquired at 1600×1200 pixels and a depth of 12 bit.

Figure 6:
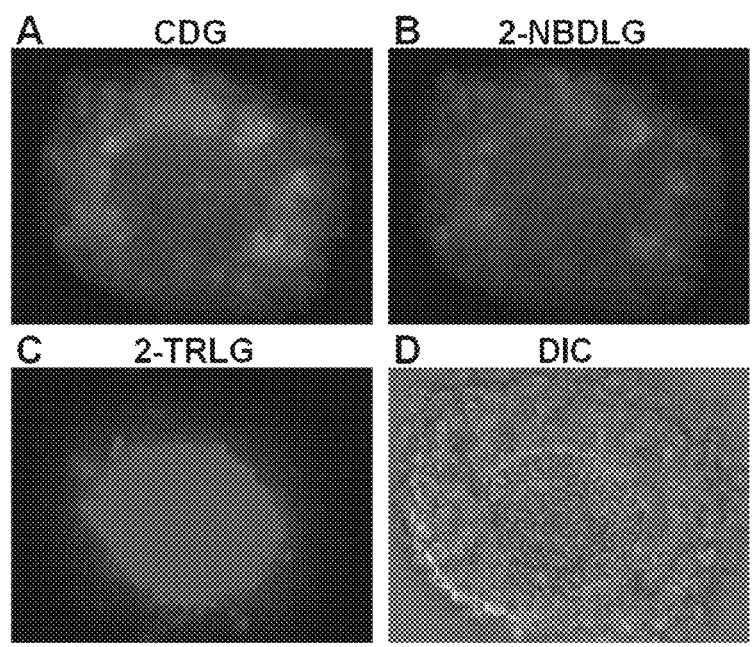
FIG. 6 shows fluorescence microscopic images which were taken 6 minutes after the start of washout of a CDG+2-NBDLG+2-TRLG mixed solution which had been administered for 3-minute to MIN6 cell masses that formed spheroids.
Figure 7:
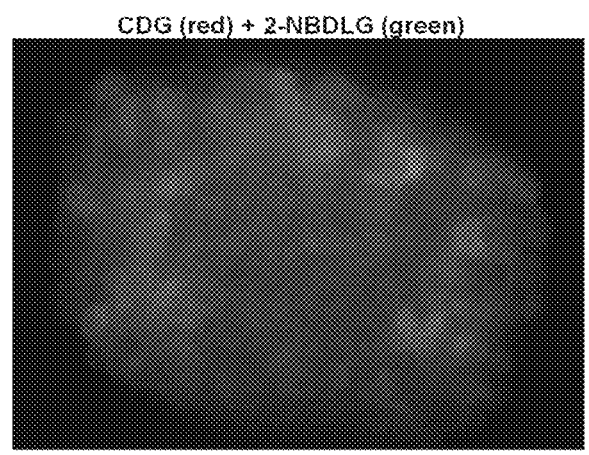
FIG. 7 is a superimposed image of FIGS. 6A and 6B. However, the uptake of CDG is expressed in red color instead of blue color in order to facilitate visualizing the localization of CDG and 2-NBDLG.

The results of administering the 100 μM CDG+100 μM 2-NBDLG+20 μM 2-TRLG mixed solution for 3 minutes to the MIN6 cell masses that formed spheroids are shown in FIGS. 6 and 7. FIG. 6 shows fluorescence microscopic images taken 6 minutes after the start of washout of the mixed solution. FIGS. 6A, 6B, and 6C show blue fluorescence-emitting CDG, green fluorescence-emitting 2-NBDLG, and red fluorescence-emitting 2-TRLG, respectively, taken into cells. FIG. 6D is a differential interference contrast (DIC) image. The central portion of the spheroid showed the strong uptake of 2-TRLG, and the cell membrane permeability was enhanced as also described in the previous report of the inventors (WO2012/133688 (Patent Literature 4)). Thus, the uptake of CDG or 2-NBDLG exhibited by the cells present in this region seems to be mainly based on nonspecific uptake ascribable to the enhanced membrane permeability. By contrast, in a doughnut-like region surrounding the central portion of the spheroid, only a portion of the cells exhibited such uptake of 2-TRLG, and the uptake of CDG and 2-NBDLG in this region was not uniform.

FIG. 7 is a superimposed image of FIGS. 6A and 6B. The uptake of CDG is expressed in red color instead of blue color in order to facilitate visualizing the localization of CDG and 2-NBDLG. There existed nearly red cells that exhibited the relatively strong cellular uptake of CDG, nearly green cells that exhibited the relatively strong cellular uptake of 2-NBDLG, cells expressed in yellow color as a result of the uptake of both CDG and 2-NBDLG, and the like. The results described above indicate the possibility that the presence of cells that take less 2-NBDLG therein, but take CDG therein can be detected by the concurrent administration of CDG and 2-NBDLG to cell masses.

In addition, 2-NBDLG was strongly taken into the cytoplasm to thereby yield an image as if denucleated, whereas CDG was not only taken into the cytoplasm but unexpectedly taken into the nucleus. This was also verified by the presence of cells whose nucleus was stained red by reflecting the uptake of CDG and whose cytoplasm was stained yellow by reflecting the uptake of CDG and 2-NBDLG in FIG. 7.

Example 17: Imaging of Tumor Cell Mass Consisting of Mouse Insulinoma Cells (MIN6) Using CLG/2-NBDLG/2-TRLG Fluorescent imaging was conducted in the same way as in Example 16 except that a CLG/2-NBDLG/2-TRLG mixed solution was used instead of the CDG/2-NBDLG/2-TRLG mixed solution for MIN6 cell masses at culture day 15.

Figure 8:
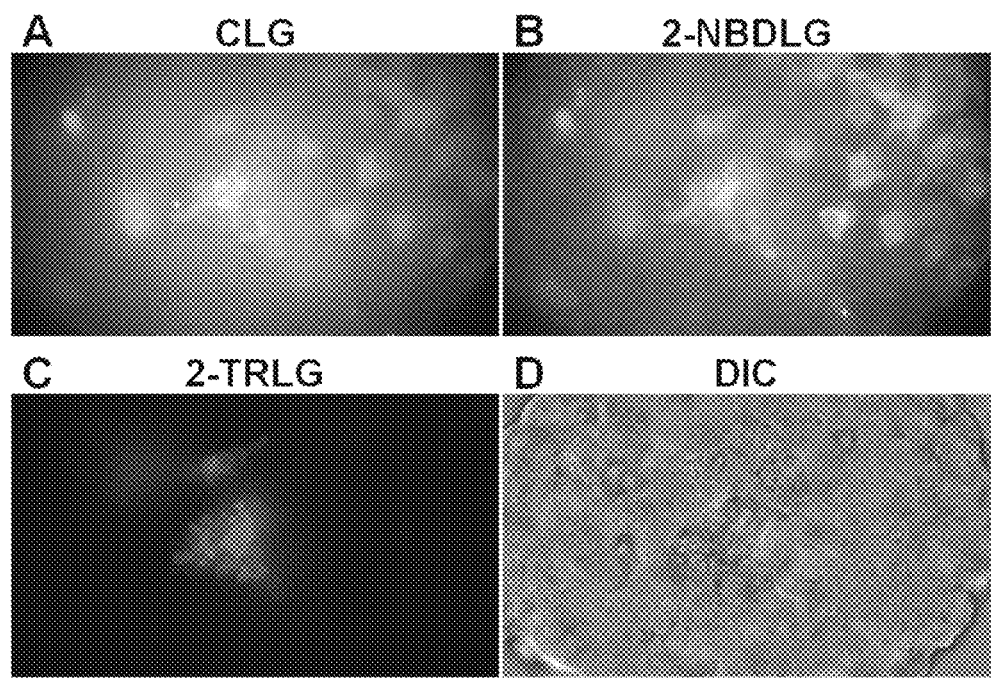
FIG. 8 shows fluorescence microscopic images which were taken 6 minutes after the start of washout of a CLG+2-NBDLG+2-TRLG mixed solution which had been administered for 3-minute to MIN6 cell masses that formed spheroids.

The results are shown in FIG. 8. FIG. 8 shows fluorescence microscopic images taken 6 minutes after the start of washout of the 100 μM CLG+100 μM 2-NBDLG+20 μM 2-TRLG mixed solution after 3-minute administration of the mixed solution to MIN6 cell masses that formed spheroids. FIGS. 8A, 8B, and 8C show blue fluorescence-emitting CLG, green fluorescence-emitting 2-NBDLG, and red fluorescence-emitting 2-TRLG, respectively, taken into cancer cells. FIG. 8D is a differential interference contrast (DIC) image. Unlike the case of CDG, all the cells that strongly took CLG therein also exhibited the uptake of 2-NBDLG. Like CDG, CLG was also strongly taken not only into the cytoplasm but into the nucleus.

Example 18: Application of CLG to Acutely Isolated Normal Neuronal Cell (Experimental Method)
(1) Preparation of CLG Solution and Mixed Solution with Additional Fluorescent Sugar Derivative
Preparation of CLG Solution
The whole amount of the 0.5 mg CLG vial was recovered using 0.73 mL in total of 10% DMSO and dissolved (100 μM) by addition to 14.79 ml of a HEPES solution for image acquisition according to the method described in Non Patent Literature 2.

Preparation of 100 μM CLG+20 μM 2-TRLG Mixed Solution

The whole amount of the 0.2 mg 2-TRLG vial was recovered using 130 μL in total of DMSO and dissolved in 13 mL of the CLG solution according to the method described in Non Patent Literature 2 (final concentration: 100 μM CLG+20 μM 2-TRLG mixed solution).

(1-1) HEPES Solution for Image Acquisition

A solution having the following composition was used for fluorescence image acquisition.

150 mM NaCl, 5 mM KCl, 1 mM $MgCl_2$, 2 mM $CaCl_2$, and 10 mM HEPES (the pH of the solution was adjusted to 7.4 with a 1 M tris(2-amino-2-hydroxymethyl-1,3-propanediol) solution). The concentration of glucose was set to 10 mM. 0.1 mM carbenoxolone (Sigma-Aldrich, #C4790) was added thereto for the purpose of inhibiting the entrance and exit of fluorescently labeled glucose by way of gap junction/hemichannel. This HEPES solution for image acquisition was used for preparing the CLG solution and the mixed solution with the additional fluorescent sugar derivative.

(2) Observation of Neuronal Cell Using Perfusion Chamber

Neuronal cells of the substantia nigra pars reticulate of the midbrain of a 21-day-old mouse were acutely isolated according to the method described in the previous reports of the inventors (WO2010/16587 (Patent Literature 2)) and (WO2012/133688 (Patent Literature 4)) and attached to each glass cover slip coated with poly-L-lysine. Then, the glass cover slip was transferred into the HEPES solution for image acquisition in a perfusion chamber loaded on a stage of a fluorescence microscope, followed by observation.

(2-1) Perfusion Chamber

A silicon plate of 1 mm thickness bored to have a streamline-shaped hole (10 mm wide×35 mm long) was placed via cover glass onto an aluminum heating control platform (Warner Instruments) having a round hole (diameter: 18 mm) for an objective lens at the bottom, and allowed to be in close contact with the cover glass.

The perfusion of the solution was carried out according to the method described in Non Patent Literature 2.

(3) Perfusate Feeding System to Perfusion Chamber

The HEPES solution for image acquisition was warmed in advance in an aluminum syringe heater and supplied to the perfusion chamber through hydrostatic pressure. The perfusion rate was adjusted to 1.3±0.2 mL/min using a flow rate adjuster. Immediately before being introduced to the perfusion chamber, the solution was rewarmed via an inline heater so that the actually measured temperature of the perfusate in an observation region in the chamber was adjusted to 32.5±1° C. The CLG/2-TRLG mixed solution was able to be supplied in the same way as above and was switched with the HEPES solution for image acquisition using an electromagnetic valve capable of controlling the opening and closing of the channel. The solution was removed using a vacuum pump capable of controlling suction pressure.

(4) Image Acquisition Condition

The fluorescence microscope used was NIKON ECLIPS-Ti, and images were acquired with a CCD camera Retiga 2000R.

CLG and 2-TRLG were each detected using the following filter cassette.

CLG (Blue Channel):
Excitation 360/40 nm, Dichroic mirror 400 nm, Emission 460/50 nm.

2-TRLG (Red Channel):
Excitation 567/15 nm, Dichroic mirror 593 nm, Emission 593 nm Long pass.

The objective lens used in this method was ×20 dry lens (Nikon Plan S Fluor). The images were acquired at 1600× 1200 pixels.

Figure 9:
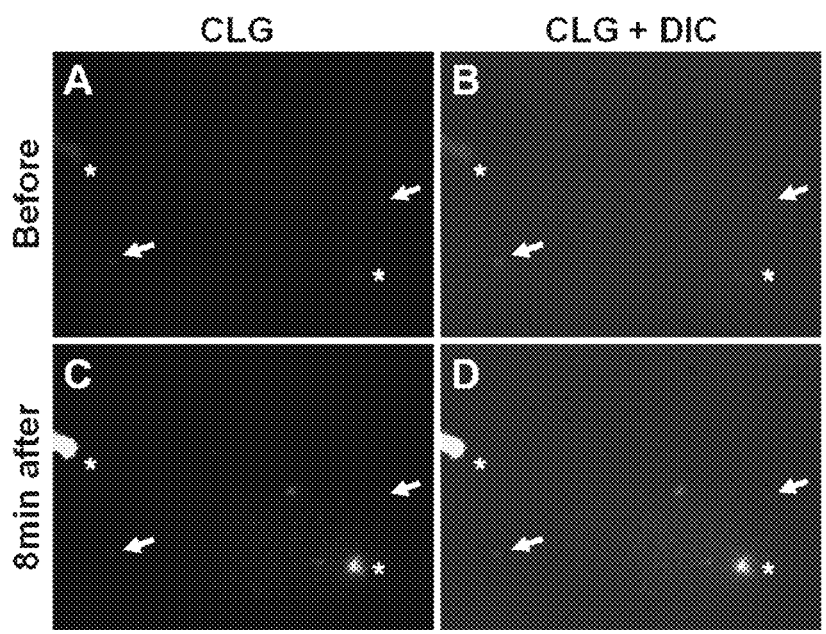
FIG. 9 shows fluorescence emitted by cells which was observed in a blue fluorescence wavelength region suitable for the observation of CLG before administration of a CLG+2-TRLG mixed solution to acutely isolated normal neuronal cells and 8 minutes after the start of washout following 3-minute administration of the mixed solution.
Figure 10:
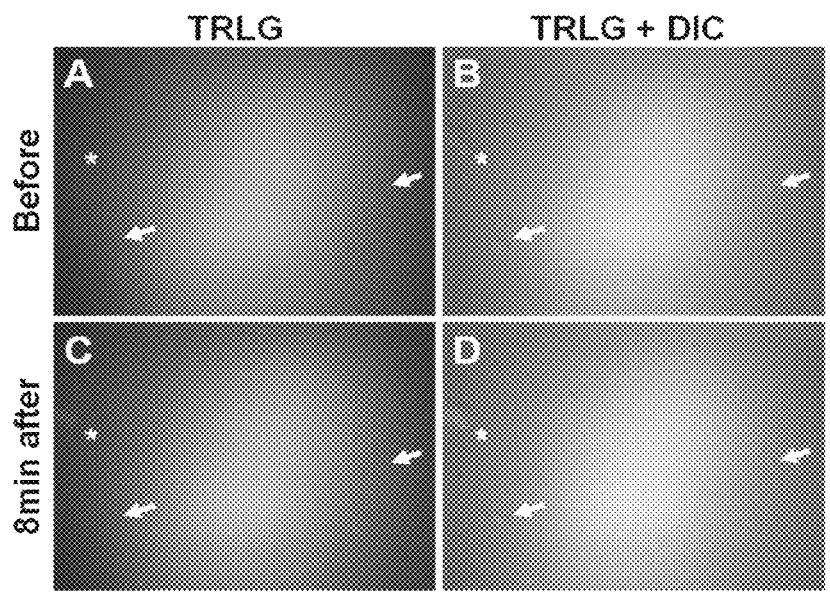
FIG. 10 shows fluorescence microscopic images showing the change in fluorescence intensity exhibited by the cells between before and after the administration of the CLG+2-TRLG mixed solution in FIG. 9, as observed in a red fluorescence wavelength region suitable for the observation of 2-TRLG.

The results are shown in FIGS. 9 and 10. FIG. 9 shows the case where change in fluorescence intensity exhibited by cells between before and after 3-minute administration of the CLG+2-TRLG mixed solution to acutely isolated normal neuronal cells (arrow) was observed in the wavelength region of blue fluorescence (blue channel) emitted by CLG. The process of background subtraction was conducted both before and after the administration. FIG. 9A shows the observed autofluorescence exhibited by the normal neuronal cells (arrow) before the administration of the mixed solution. FIG. 9B shows a differential interference contrast (DIC) image superimposed on the image of FIG. 9A for further understanding. As is evident, the normal neuronal cells slightly emitted autofluorescence before the administration of the mixed solution. * depicts the debris of killed cells. The debris on the left side of the image exhibited relatively strong autofluorescence. FIG. 9C is a fluorescence microscopic image taken 8 minutes after the start of washout of the mixed solution. FIG. 9D is a DIC image superimposed on the image of FIG. 9C. As seen from the figure, blue fluorescence-emitting CLG was strongly taken into the cell debris (*) in a nonspecific manner, whereas such uptake was not observed in the normal neuronal cells (arrow).

FIG. 10 shows that change in fluorescence between before and after the administration of the mixed solution in FIG. 9, as observed at the same time as in the wavelength region of red fluorescence (red channel) emitted by 2-TRLG. FIG. 10A shows an autofluorescence image taken before the administration of the mixed solution. FIG. 10B shows a differential interference contrast (DIC) image superimposed on the image of FIG. 10A in order to facilitate visualizing the positions of cells. The autofluorescence of the cells was very small in the red fluorescence wavelength region. Intense red color at the central portion of the image resulted from the leakage of a portion of irradiation light to the detector side through a fluorescence filter because the red fluorescence was photographed with sensitivity enhanced for the purpose of detecting weak fluorescence (see Dichroic mirror and Emission wavelengths of the red channel). Here, the image is shown as it is without shading correction.

As is evident from FIG. 10C and FIG. 10D which is a DIC image superimposed on the image of FIG. 10C, red fluorescence-emitting 2-TRLG was taken into the cell debris (*) in a nonspecific manner, but was not taken into the normal neuronal cells (arrow). In short, nonspecific enhancement in cell membrane permeability that brings about the entry of 2-TRLG into the normal neuronal cells indicated by arrows in this experiment was not detected, suggesting that the membrane integrity of these cells was maintained.

On the other hand, as shown in Example 17, the L-glucose derivative CLG was strongly taken into the spheroid of the mouse insulinoma cells (MING), which are cancer cells.

Example 19: Application of CDG to Acutely Isolated Normal Neuronal Cell

This experiment was conducted in the same way as the experimental method described in Example 18 except that CDG was used instead of CLG to prepare a 100 μM CDG+20 μM 2-TRLG mixed solution (concentrations were final concentrations) and the neuronal cells of the substantia nigra pars reticulate of the midbrain were prepared from a 14-day-old mouse.

Figure 11:
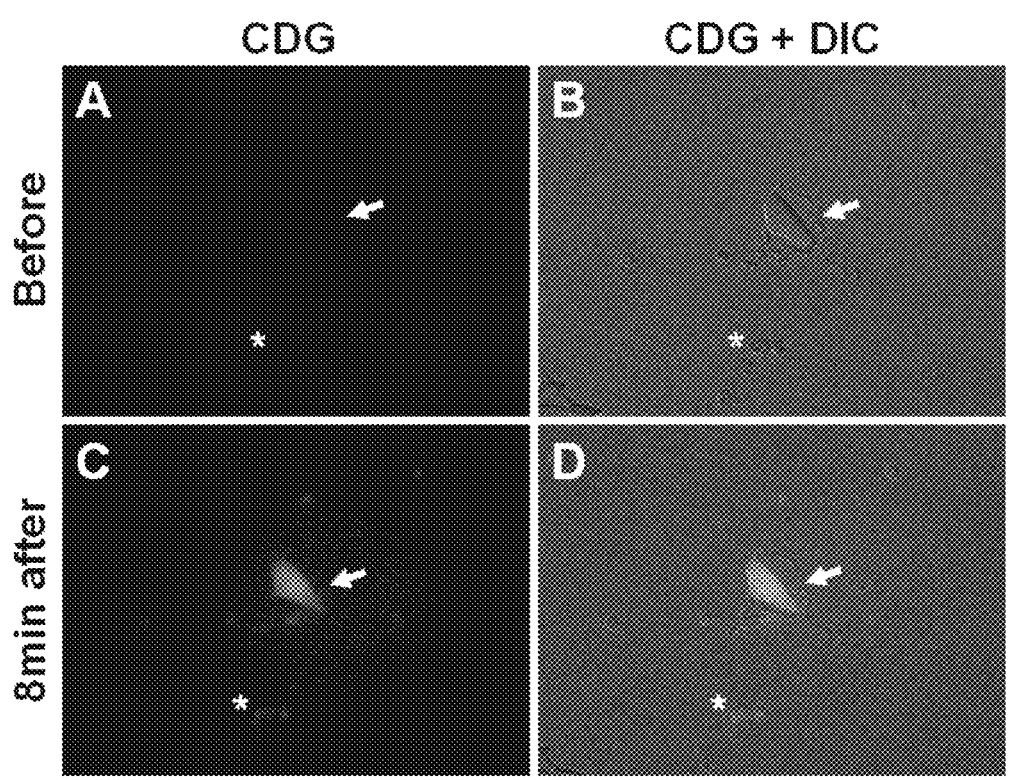
FIG. 11 shows results of change in fluorescence intensity exhibited by acutely isolated normal neuronal cells (arrow) between before and after 3-minute administration of a CDG+2-TRLG mixed solution to the cells, as observed in the wavelength region (blue channel) of blue fluorescence emitted by CDG.
Figure 12:
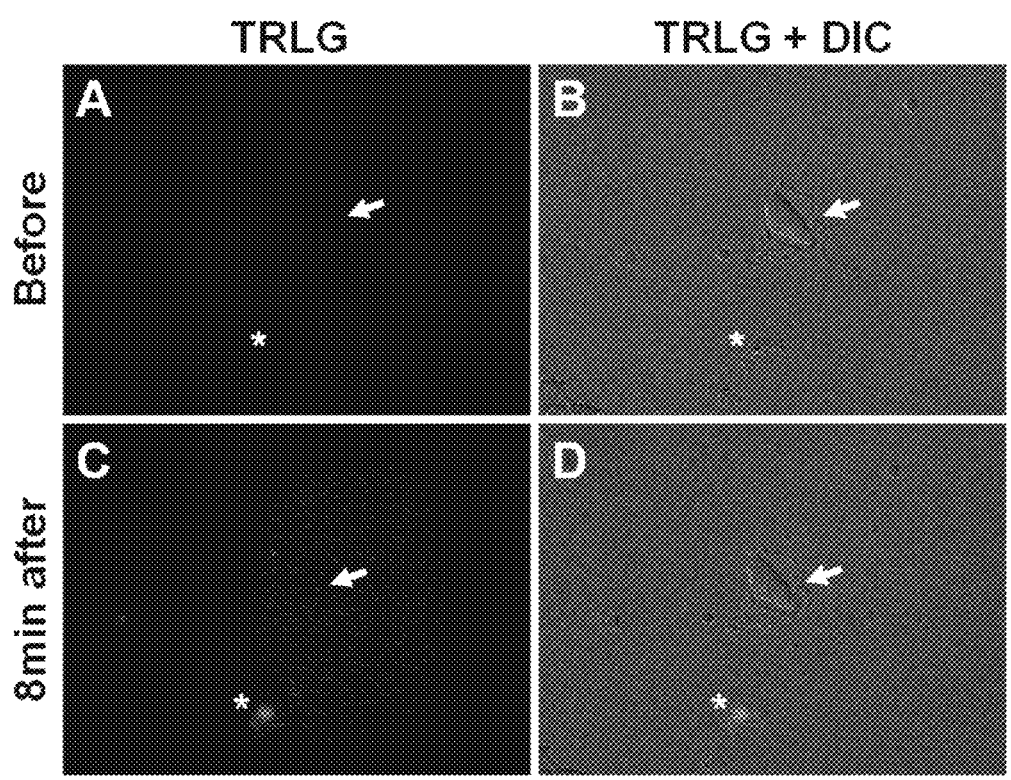
FIG. 12 shows results of change in fluorescence between before and after the administration of the mixed solution in FIG. 11, as simultaneously observed in the wavelength region (red channel) of red fluorescence emitted by 2-TRLG.

The results are shown in FIGS. 11 and 12. FIG. 11 shows the case where change in fluorescence intensity exhibited by cells between before and after 3-minute administration of the CDG+2-TRLG mixed solution to acutely isolated normal neuronal cells (arrow) was observed in the wavelength region of blue fluorescence (blue channel) emitted by CDG. The process of background subtraction was conducted both before and after the administration. FIG. 11A shows the observed autofluorescence exhibited by the normal neuronal cells (arrow) before the administration of the mixed solution. FIG. 11B shows a differential interference contrast (DIC) image superimposed on the image of FIG. 11A for further understanding. * depicts the debris of killed cells. FIG. 11C is a fluorescence microscopic image taken 8 minutes after the start of washout of the mixed solution. FIG. 11D is a DIC image superimposed on the image of FIG. 11C. As seen from the figure, blue fluorescence-emitting CDG was taken into the normal neuronal cells (arrow). On the other hand, such uptake was not observed in the cell debris (*).

FIG. 12 shows that change in fluorescence between before and after the administration of the mixed solution in FIG. 11, as observed at the same time in the wavelength region of red fluorescence (red channel) emitted by 2-TRLG. FIG. 12A shows an autofluorescence image taken before the administration of the mixed solution. FIG. 12B shows a differential interference contrast (DIC) image superimposed on the image of FIG. 12A in order to facilitate visualizing the positions of cells. The autofluorescence of the cells was very small in the red fluorescence wavelength region.

As is evident from FIG. 12C and FIG. 12D which is a DIC image superimposed on the image of FIG. 12C, red fluorescence-emitting 2-TRLG was taken into the cell debris (*) in a nonspecific manner, but was not taken into the normal neuronal cells (arrow). In short, nonspecific enhancement in cell membrane permeability that brings about the entry of 2-TRLG into the normal neuronal cells indicated by arrows in this experiment was not detected, suggesting that the membrane integrity was maintained.

The detailed description above is given merely for illustrating the objects and subjects of the present invention and is not intended to limit the scope of the attached claims. It is obvious to those skilled in the art from the instruction described herein that various changes and modification can be made in the described embodiments without departing from the scope of the attached claims.

INDUSTRIAL APPLICABILITY

The present invention provides a novel glucose derivative. The present invention also provides an imaging agent and an imaging method for a cell using the glucose derivative.

The invention claimed is:

1. A glucose derivative which is a compound represented by the following formula (1):

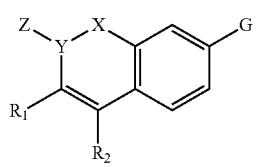

(1)

wherein X—Y—Z represents O—C=O, NH—C=O, $NR_3$—C=O, or N=C—$OR_4$, wherein $R_3$ represents $C_1$-$C_5$ alkyl, and $R_4$ represents $C_1$-$C_5$ alkyl;

$R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl; and G represents a group selected from the following formulas (G1) to (G4):

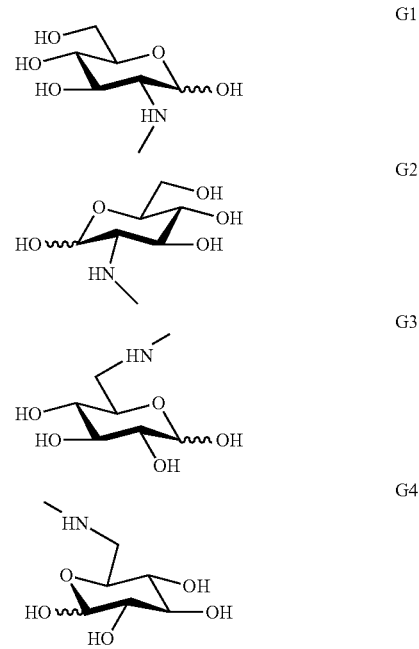

or a salt thereof.

2. The glucose derivative according to claim 1, which is a compound represented by the following formula (2):

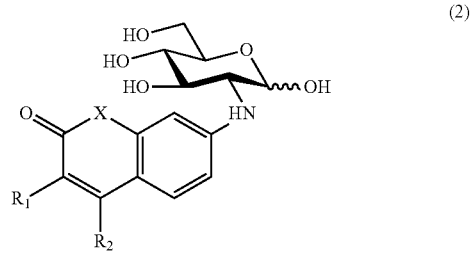

(2)

wherein X represents O, NH, or $NR_3$, wherein $R_3$ represents $C_1$-$C_5$ alkyl; and $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl, or a salt thereof.

3. The glucose derivative according to claim 1, which is a compound represented by the following formula (3):

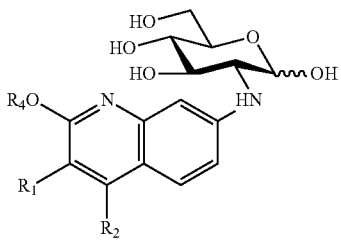

wherein $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl; and $R_4$ represents $C_1$-$C_5$ alkyl, or a salt thereof.

4. The glucose derivative according to claim 1, which is a compound represented by the following formula (4):

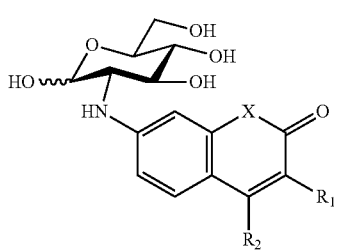

wherein X represents O, NH, or $NR_3$, wherein $R_3$ represents $C_1$-$C_5$ alkyl; and
$R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl,
or a salt thereof.

5. The glucose derivative according to claim 1, which is a compound represented by the following formula (5):

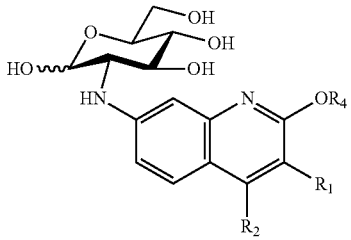

wherein $R_1$ and $R_2$ each independently represent a group selected from the group consisting of hydrogen, halogen, $C_1$-$C_5$ alkyl, $C_2$-$C_5$ alkenyl, $C_2$-$C_5$ alkynyl, $C_1$-$C_5$ haloalkyl, $C_1$-$C_5$ alkylamino, cycloalkyl, phenyl, pyridyl, thiophenyl, pyrrolyl, and furanyl; and $R_4$ represents $C_1$-$C_5$ alkyl, or a salt thereof.

6. The glucose derivative according to claim 1, which is selected from the group consisting of the following compounds:
2-deoxy-2-(2-oxo-2H-chromen-7-yl)amino-D-glucose (CDG), 2,4-dideoxy-2-(2-oxo-2H-chromen-7-yl) amino-4-fluoro-D-glucose (4-F-CDG), 2,6-dideoxy-2-(2-oxo-2H-chromen-7-yl)amino-6-fluoro-D-glucose (6-F-CDG), 2-deoxy-2-(2-oxo-1,2-dihydroquinolin-7-yl)amino-D-glucose (QDG), 2-deoxy-2-(2-oxo-2H-3-methyl-chromen-7-yl)amino-D-glucose (3-MCDG), 2-deoxy-2-(2-oxo-2H-4-methyl-chromen-7-yl)amino-D-glucose (4-MCDG), 2-deoxy-2-(2-oxo-2H-3-trifluoromethyl-chromen-7-yl)amino-D-glucose (3-TFM-CDG), 2-deoxy-2-(2-oxo-2H-4-trifluoromethyl-chromen-7-yl)amino-D-glucose (4-TFMCDG), 2-deoxy-2-(2-oxo-1,2-dihydro-3-methyl-quinolin-7-yl)amino-D-glucose (3-MQDG), 2-deoxy-2-(2-oxo-1,2-dihydro-4-methyl-quinolin-7-yl)amino-D-glucose (4-MQDG), 2-deoxy-2-(2-oxo-1,2-dihydro-3-trifluoromethyl-quinolin-7-yl)amino-D-glucose (3-TFMQDG), 2-deoxy-2-(2-oxo-1,2-dihydro-4-trifluoromethyl-quinolin-7-yl)amino-D-glucose (4-TFMQDG), 2-deoxy-2-(2-oxo-2H-chromen-7-yl)amino-L-glucose (CLG), 2,4-dideoxy-2-(2-oxo-2H-chromen-7-yl) amino-4-fluoro-L-glucose (4-F-CLG), 2,6-dideoxy-2-(2-oxo-2H-chromen-7-yl)amino-6-fluoro-L-glucose (6-F-CLG), 2-deoxy-2-(2-oxo-1,2-dihydroquinolin-7-yl)amino-L-glucose (QLG), 2-deoxy-2-(2-oxo-2H-3-methyl-chromen-7-yl)amino-L-glucose (3-MCLG), 2-deoxy-2-(2-oxo-2H-4-methyl-chromen-7-yl)amino-L-glucose (4-MCLG), 2-deoxy-2-(2-oxo-2H-3-trifluoromethyl-chromen-7-yl)amino-L-glucose (3-TFM-CLG), 2-deoxy-2-(2-oxo-2H-4-trifluoromethyl-chromen-7-yl)amino-L-glucose (4-TFMCLG), 2-deoxy-2-(2-oxo-1,2-dihydro-3-methyl-quinolin-7-yl)amino-L-glucose (3-MQLG), 2-deoxy-2-(2-oxo-1,2-dihydro-4-methyl-quinolin-7-yl)amino-L-glucose (4-MQLG), 2-deoxy-2-(2-oxo-1,2-dihydro-3-trifluoromethyl-quinolin-7-yl)amino-L-glucose (3-TFMQLG), and 2-deoxy-2-(2-oxo-1,2-dihydro-4-trifluoromethyl-quinolin-7-yl)amino-L-glucose (4-TFMQLG).

7. A radiolabeled glucose derivative comprising a glucose derivative according to claim 1, wherein a hydroxy group at any one of the 2-, 4-, and 6-positions of the glucose is substituted by $^{18}F$.

8. The glucose derivative according to claim 1 which is in a radiolabeled form selected from
2-deoxy-2-(2-oxo-2H-3-[$^{11}C$]methyl-chromen-7-yl) amino-D-glucose (3-[$^{11}C$]MCDG), 2-deoxy-2-(2-oxo-2H-4-[$^{11}C$]methyl-chromen-7-yl)amino-D-glucose (4-[$^{11}C$]MCDG), 2-deoxy-2-(2-oxo-2H-3-[$^{18}F$] fluorodifluoromethyl-chromen-7-yl)amino-D-glucose (3-[$^{18}F$]TFMCDG), 2-deoxy-2-(2-oxo-2H-4-[$^{18}F$]fluorodifluoromethyl-chromen-7-yl)amino-D-glucose (4-[$^{18}F$]TFMCDG), 2-deoxy-2-(2-oxo-1,2-dihydro-3-[$^{11}C$]methyl-quinolin-7-yl)amino-D-glucose (3-[$^{11}C$] MQDG), 2-deoxy-2-(2-oxo-1,2-dihydro-4-[$^{11}C$] methyl-quinolin-7-yl)amino-D-glucose (4-[$^{11}C$] MQDG), 2-deoxy-2-(2-oxo-1,2-dihydro-3-[$^{18}F$] fluorodifluoromethyl-quinolin-7-yl)amino-D-glucose (3-[$^{18}F$]TFMQDG), 2-deoxy-2-(2-oxo-1,2-dihydro-4-[$^{18}F$]fluorodifluoromethyl-quinolin-7-yl)amino-D-glucose (4-[$^{18}F$]TFMQDG), 2-deoxy-2-(2-oxo-2H-3-[$^{11}C$]methyl-chromen-7-yl)amino-L-glucose (3-[$^{11}C$] MCLG), 2-deoxy-2-(2-oxo-2H-4-[$^{11}C$]methyl-chromen-7-yl)amino-L-glucose (4-[$^{11}C$]MCLG), 2-deoxy-2-(2-oxo-2H-3-[$^{18}F$]fluorodifluoromethyl-chromen-7-yl)amino-L-glucose (3-[$^{18}F$]TFMCLG), 2-deoxy-2-(2-oxo-2H-4-[$^{18}F$]fluorodifluoromethyl-chromen-7-yl)amino-L-glucose (4-[$^{18}F$]TFMCLG), 2-deoxy-2-(2-oxo-1,2-dihydro-3-[$^{11}C$]methyl-quinolin-7-yl)amino-L-glucose (3-[$^{11}$C]MQLG), 2-deoxy-2-(2-oxo-1,2-dihydro-4-[$^{11}$C]methyl-quinolin-7-yl)amino-L-glucose (4-[$^{11}$C]MQLG), 2-deoxy-2-(2-oxo-1,2-dihydro-3-[$^{18}$F]fluorodifluoromethyl-quinolin-7-yl)amino-L-glucose (3-[$^{18}$F]TFMQLG), and 2-deoxy-2-(2-oxo-1,2-dihydro-4-[$^{18}$F]fluorodifluoromethyl-quinolin-7-yl)amino-L-glucose (4-[$^{18}$F]TFMQLG).

9. A composition for imaging a target cell, comprising a glucose derivative according to claim 1.

10. A method for imaging a target cell, comprising the following steps:
 a. contacting a composition containing a glucose derivative according to claim 1 with the target cell; and
 b. detecting fluorescence emitted by the glucose derivative present within the target cell.

11. The imaging method according to claim 10, wherein the composition in the step a further comprises an additional fluorescently labeled glucose derivative, and the step b is the step of detecting at least one of the glucose derivatives present within the target cell.

* * * * *